US008445537B2

(12) United States Patent
Tomkinson et al.

(10) Patent No.: US 8,445,537 B2
(45) Date of Patent: May 21, 2013

(54) COMPOUNDS THAT INHIBIT HUMAN DNA LIGASES AND METHODS OF TREATING CANCER

(75) Inventors: Alan E. Tomkinson, Glenwood, MD (US); Xi Chen, Baltimore, MD (US); Barbara Dziegielewska, Baltimore, MD (US); Alexander D. Mackerell, Baltimore, MD (US); Shijun Zhong, Ellicott City, MD (US); Gerald M. Wilson, Middle River, MD (US)

(73) Assignee: STC.UNM, Albuquerque, NM (US)

( * ) Notice: Subject to any disclaimer, the term of this patent is extended or adjusted under 35 U.S.C. 154(b) by 590 days.

(21) Appl. No.: 12/576,410

(22) Filed: Oct. 9, 2009

(65) Prior Publication Data
US 2010/0099683 A1    Apr. 22, 2010

Related U.S. Application Data

(63) Continuation-in-part of application No. PCT/US2008/059931, filed on Apr. 10, 2008.

(60) Provisional application No. 60/911,000, filed on Apr. 10, 2007.

(51) Int. Cl.
*A61K 31/16* (2006.01)
*A61K 31/13* (2006.01)

(52) U.S. Cl.
USPC .......................................... 514/615; 514/638

(58) Field of Classification Search
None
See application file for complete search history.

(56) References Cited

PUBLICATIONS

Wei et al. Molecular and Cellular Biology, Jun. 1995, pp. 3206-3216.*
O'Driscoll et al. Molecular Cell, 2001, vol. 8, pp. 1175-1185.*
Ding, J., Miao, Z. H., Meng, L. H., and Geng, M. Y. (2006) *Trends Pharmacol Sci* 27(6), 338-344.
Madhusudan, S., and Hickson, I. D. (2005) *Trends Mol Med* 11(11), 503-511.
Madhusudan, S., and Middleton, M. R. (2005) *Cancer Treat Rev* 31(8), 603-617.
Bryant, H. E., Schultz, N., Thomas, H. D., Parker, K. M., Flower, D., Lopez, E., Kyle, S., Meuth, M., Curtin, N. J., and Helleday, T. (2005) *Nature* 434(7035), 913-917.
Farmer, H., McCabe, N., Lord, C. J., Tutt, A. N., Johnson, D. A., Richardson, T. B., Santarosa, M., Dillon, K. J., Hickson, I., Knights, C., Martin, N. M., Jackson, S. P., Smith, G. C., and Ashworth, A. (2005) *Nature* 434(7035), 917-921.
Tomkinson, A. E., Vijayakumar, S., Pascal, J. M., and Ellenberger, T. (2006) *Chem Rev* 106(2), 687-699.
Barnes, D. E., Tomkinson, A. E., Lehmann, A. R., Webster, A. D., and Lindahl, T. (1992) *Cell* 69(3), 495-503.

Lehmann, A. R., Willis, A. E., Broughton, B. C., James, M. R., Steingrimsdottir, H., Harcourt, S. A., Arlett, C. F., and Lindahl, T. (1988) *Cancer Res* 48(22), 6343-6347.
Teo, I. A., Broughton, B. C., Day, R. S., James, M. R., Karran, P., Mayne, L. V., and Lehmann, A. R. (1983) *Carcinogenesis* 4(5), 559-564.
Sun, D., Urrabaz, R., Nguyen, M., Marty, J., Stringer, S., Cruz, E., Medina-Gundrum, L., and Weitman, S. (2001) *Clin Cancer Res* 7(12), 4143-4148.
Caldecott, K. W., McKeown, C. K., Tucker, J. D., Ljungquist, S., and Thompson, L. H. (1994) *Mol Cell Biol* 14(1), 68-76.
Caldecott, K. W., Tucker, J. D., Stanker, L. H., and Thompson, L. H. (1995) *Nucleic Acids Res* 23(23), 4836-4843.
Lakshmipathy, U., and Campbell, C. (1999) *Mol Cell Biol* 19(5), 3869-3876.
Lakshmipathy, U., and Campbell, C. (2001) *Nucleic Acids Res* 29(3), 668-676.
Frosina, G., Fortini, P., Rossi, O., Carrozzino, F., Raspaglio, G., Cox, L. S., Lane, D. P., Abbondandolo, A., and Dogliotti, E. (1996) *J Biol Chem* 271(16), 9573-9578.
Levin, D. S., McKenna, A. E., Motycka, T. A., Matsumoto, Y., and Tomkinson, A. E. (2000) *Curr Biol* 10(15), 919-922.
Adachi, N., Ishino, T., Ishii, Y., Takeda, S., and Koyama, H. (2001) *Proc Natl Acad Sci U S A* 98(21), 12109-12113.
Pascal, J. M., O'Brien, P. J., Tomkinson, A. E., and Ellenberger, T. (2004) *Nature* 432(7016), 473-478.
Sun, D., and Urrabaz, R. (2004) *J Biochem Biophys Methods* 59(1), 49-59.
Tan, G. T., Lee, S., Lee, I. S., Chen, J., Leitner, P., Besterman, J. M., Kinghorn, A. D., and Pezzuto, J. M. (1996) *Biochem J* 314 ( Pt 3), 993-1000.
Hancock, C. N., Macias, A., Lee, E. K., Yu, S. Y., Mackerell, A. D., Jr., and Shapiro, P. (2005) *J Med Chem* 48(14), 4586-4595.
Chen, X., Pascal, J., Vijayakumar, S., Wilson, G. M., Ellenberger, T., and Tomkinson, A. E. (2006) *Methods Enzymol* 409, 39-52.
Gallmeier, E., Hucl, T., Brody, J. R., Dezentje, D. A., Tahir, K., Kasparkova, J., Brabec, V., Bachman, K. E., and Kern, S. E. (2007) *Cancer Res* 67(5), 2169-2177.
Chen, L., Trujillo, K., Sung, P., and Tomkinson, A. E. (2000) *J Biol Chem* 275(34), 26196-26205.
Ahel, I., Rass, U., El-Khamisy, S. F., Katyal, S., Clements, P. M., McKinnon, P. J., Caldecott, K. W., and West, S. C. (2006) *Nature* 443(7112), 713-716.
Baumann, P., and West, S. C. (1998) *Proc Natl Acad Sci U S A* 95(24), 14066-14070.

(Continued)

*Primary Examiner* — James D Anderson
(74) *Attorney, Agent, or Firm* — Henry D. Coleman; R. Neil Sudol

(57) ABSTRACT

Methods for treating cancer using compounds that inhibit human DNA ligases. Methods for using compounds that inhibit human DNA ligases to provide insights into the reaction mechanisms of human DNA ligases, for example to identify the human DNA ligase involved in different DNA repair pathways. Screening methods for compounds that inhibit human DNA ligases.

16 Claims, 19 Drawing Sheets

PUBLICATIONS

Zheng, L.; Dai, H., Qiu, J., Huang, Q., and Shen, B. (2007) *Mol Cell Biol* 27(8), 3176-3186.

Mackey, Z. B.; Niedergang, C.; Murcia, J. M.; Leppard, J.; Au, K.; Chen, J.; de Murcia, G.; Tomkinson, A. E., DNA ligase III is recruited to DNA strand breaks by a zinc finger motif homologous to that of poly(ADP-ribose) polymerase. Identification of two functionally distinct DNA binding regions within DNA ligase III. *J. Biol. Chem.* 1999, 274, (31), 21679-87.

Srivastava, S. K.; Dube, D.; Tewari, N.; Dwivedi, N.; Tripathi, R. P.; Ramachandran, R., Mycobacterium tuberculosis NAD+-dependent DNA ligase is selectively inhibited by glycosylamines compared with human DNA ligase I. *Nucleic Acids Res.* 2005, 33, (22), 7090-101.

Wang W, Bambara RA. Human Bloom protein stimulates flap endonuclease 1 activity by resolving DNA secondary structure. J Biol Chem 2005;280:5391-9.

Di Virgilio M, Gautier J. Repair of double-strand breaks by non-homologous end joining in the absence of Mre11. J Cell Biol 2005;171:765-71.

Chen L, Trujillo K, Ramos W, Sung P, Tomkinson AE. Promotion of Dn14-catalyzed DNA end-joining by the Rad50/Mre11/Xrs2 and Hdf1/Hdf2 complexes. Mol Cell 2001;8:1105-15.

Ewing TJ, Makino S, Skillman AG, Kuntz ID. Dock 4.0: search strategies for automated molecular docking of flexible molecule databases. J Comput Aided Mol Des 2001;15:411-28.

Huang N, Nagarsekar A, Xia G, Hayashi J, MacKerell AD, Jr. Identification of non-phosphate-containing small molecular weight inhibitors of the tyrosine kinase p56 Lck SH2 domain via in silico screening against the pY+3 binding site. J Med Chem 2004;47:3502-11.

Kuntz ID, Blaney JM, Oatley SJ, Langridge R, Ferrin TE. A geometric approach to macromolecule-ligand interactions. J Mol Biol 1982;161:269-88.

Markowitz J, Chen I, Gitti R, et al. Identification and characterization of small molecule inhibitors of the calcium-dependent S100B-p53 tumor suppressor interaction. J Med Chem 2004;47:5085-93.

Berman, H. M.; Westbrook, J.; Feng, Z.; Gilliland, G.; Bhat, T. N.; Weissig, H.; Shindyalov, I. N.; Bourne, P. E., The Protein Data Bank. Nucleic Acids Res. 2000, 28, (1), 235-42.

Brooks, B. R.; Bruccoleri, R. E.; Olafson, B. D.; States, D. J.; Swaminathan, S.; Karplus, M., CHARMM: A program for macromolecular energy, minimization, and dynamics calculations. J. Comput. Chem. 1983, 4, (2), 187-217.

MacKerrel, A. D., Jr.; Bashford, D.; Bellott, M.; Dunbrack, R. L.; Evanseck, J. D.; Field, M. Fischer, S.; Gao, J.; Guo, H.; Ha, S.; Joseph-McCarthy, D.; Kuchnir, L.; Kuczera, Lau, F. T. K.; Mattos, C.; Michnick, S.; Ngo, T.; Nguyen, D. T.; Prodhom, B.; Reiher, W. E.; Roux, B.; Schlenkrich, M.; Smith, J. C.; Stote, R.; Straub, J.; Watanabe, M.; Wiorkiewicz-Kuczera, J.; Yin, D.; Karplus, M., All-atom empirical potential for molecular modeling and dynamics studies of proteins. J. Phys. Chem. B 1998, 102, (18), 3586-3616.

Mackerell, A. D., Jr., Empirical force fields for biological macromolecules: overview and issues. J. Comput. Chem. 2004, 25, (13), 1584-604.

Brooks, C. L., III; Karplus, M., Deformable Stochastic Boundaries in Molecular Dynamics. J. Chem. Phys. 1983, 79, (12), 6312-6325.

Snyman, J. A., *Practical Mathematical Optimization: An Introduction to Basic Optimization Theory and Classical and New Gradient-Based Algorithms*. Springer-Verlag: New York, 2005; p. 257.

Beglov, D.; Roux, B., Dominant Salvation Effects from the Primary Shell of Hydration—Approximation for Molecular-Dynamics Simulations. Biopolymers 1995, 35, (2), 171-178.

Beglov, D.; Roux, B., Finite Representation of an Infinite Bulk System—Solvent Boundary Potential for Computer-Simulations. J. Chem. Phys. 1994, 100, (12), 9050-9063.

Steinbach, P. J.; Brooks, B. R., New Spherical-Cutoff Methods of Long-Range Forces in Macromolecular Simulations. *J. Comp. Chem.* 1994, 15, 667-683.

Swope, W. C.; Andersen, H. C.; Berens, P. H.; Wilson, K. R., A computer simulation method for the calculation of equilibrium constants for the formation of physical clusters of molecules: Application to small water clusters. *J. Chem. Phys.* 1982, 76, (1), 637-649.

Ryckaert, J. P.; Ciccotti, G.; Berendsen, H. J. C., Numerical Integration of the Cartesian Equations of Motion of a System with Constraints: Molecular Dynamics of n-alkanes. J. Comp. Phys. 1977, 23, 327-341.

Kelley, L. A.; Gardner, S. P.; Sutcliffe, M. J., An automated approach for clustering an ensemble of NMR-derived protein structures into conformationally related subfamilies. Protein Eng. 1996, 9, (11), 1063-5.

Connolly, M., Analytical molecular surface calculation. J. Appl. Cryst. 1983, 16, 548-558.

Connolly, M. L., Solvent-accessible surfaces of proteins and nucleic acids. Science 1983, 221, (4612), 709-13.

Ferrin, T. E.; Huang, C. C.; Jarvis, L. E.; Langridge, R., The MIDAS display system. J. Mol. Graphics 1988, 6, 13-27.

Pettersen, E. F.; Goddard, T. D.; Huang, C. C.; Couch, G. S.; Greenblatt, D. M.; Meng, E. C.; Ferrin, T. E., UCSF Chimera—a visualization system for exploratory research and analysis. J. Comput. Chem. 2004, 25, (13), 1605-12.

Halgren, T. A., MMFF VI. MMFF94s option for energy minimization studies. *J. Comp. Chem.* 1999, 20, (7), 720-729.

Halgren, T. A., MMFF VII. Characterization of MMFF94, MMFF94s, and other widely available force fields for conformational energies and for intermolecular-interaction energies and geometries. *J. Comp. Chem.* 1999, 20, (7), 730-748.

Chambers, C. C.; Hawkins, G. D.; Cramer, C. J.; Truhlar, D. G., Model for aqueous solvation based on class IV atomic charges and first solvation shell effects. *J. Phys. Chem.* 1996, 100, 16385-16398.

Li, J.; Zhu, T.; Cramer, C. J.; Truhlar, D. G., New class IV charges model for extracting accurate partial charges from wave functions. *J. Phys. Chem. A* 1998, 102, 1820-1831.

Sirois, S.; Hatzakis, G.; Wei, D.; Du, Q.; Chou, K.-C., Assessment of chemical libraries for their druggability. *Comp. Biol. Chem.* 2005, 29, 55-67.

Hancock, C. N.; Macias, A.; Lee, E. K.; Yu, S. Y.; MacKerell, A. D., Jr.; Shapiro, P., Identification of novel extracellular signal-regulated kinase docking domain inhibitors. *J. Med. Chem.* 2005, 48, (14), 4586-4595.

Huang, N.; Nagarsekar, A.; Xia, G.; Hayashi, J.; MacKerell, A. D., Jr., Identification of non-phosphate-containing small molecular weight inhibitors of the tyrosine kinase p56 Lck SH2 domain via in silico screening against the pY+3 binding site. *J. Med. Chem.* 2004, 47, (14), 3502-11.

A. R.; Kuntz, I. D., Conformational analysis of flexible ligands in macromolecular receptor sites. *J. Comput. Chem.* 1992, 13, 730-748.

Tanimoto, T., *IBM Internal Report*, Nov. 1957.

Godden, J. W.; Xue, L.; Bajorath, J., Combinatorial preferences affect molecular similarity/diversity calculations using binary fingerprints and Tanimoto coefficients. *J. Chem. Inf. Comput. Sci.* 2000, 40, (1), 163-6.

Durant, J. L.; Leland, B. A.; Henry, D. R.; Nourse, J. G., Reoptimization of MDL keys for use in drug discovery. *J. Chem. Inf. Comput. Sci.* 2002, 42, (6), 1273-80.

Willett, P.; Barnard, J. M.; Downs, G. M., Chemical similarity searching. *J. Chem. Inf. Comput. Sci.* 1998, 38, (6), 983-996.

Pan, Y.; Huang, N.; Cho, S.; MacKerell, A. D., Jr., Consideration of Molecular Weight During Compound Selection in Virtual Target-Based Database Screening. *J. Chem. Inf Comp. Sci.* 2003, 43, 267-272.

Carlson, H. A., Protein flexibility and drug design: how to hit a moving target. Curr. Opin. Chem. Biol. 2002, 6, 447-452.

Carlson, H. A.; McCammon, J. A., Accommodating Protein Flexibility in Computational Drug Design. Mol. Pharmacol. 2000, 57, 213-218.

Oprea, T. I.; Davis, A. M.; Teague, S. J.; Leeson, P. D., Is There a Difference between Leads and Drugs? A Historical Perspective. *J. Chem. Inf. Comput. Sci.* 2001, 41, 1308-1315.

Lipinski, C. A., Drug-like properties and the causes of poor solubility and poor permeability. *J. Pharmacol. Toxicol. Methods* 2000, 44, 235-249.

Lipinski, C. A.; Lombardo, F.; Dominy, B. W.; Feeney, P. J., Experimental and computational approaches to estimate solubility and permeability in drug discovery and development settings. *Adv. Drug Deliv. Rev.* 2001, 46, (1-3), 3-26.

Brown, R. D.; Martin, Y. C., An evaluation of structural descriptors and clustering methods for use in diversity selection. *SAR QSAR Environ. Res.* 1998, 8, (1-2), 23-39.

Chen, X.; Zhong, S.; Zhu, X.; Dziegielewska, B.; Ellenberger, E.; Wilson, G. M.; MacKerell, A. D., Jr..; Tomkinson, A. E., Rational Design of Human DNA Ligase Inhibitors that Target Cellular DNA Replication and Repair. *Cancer Res.* (Submitted, Dec. 2007).

* cited by examiner

Figure 1. Structures of 9 active compounds.
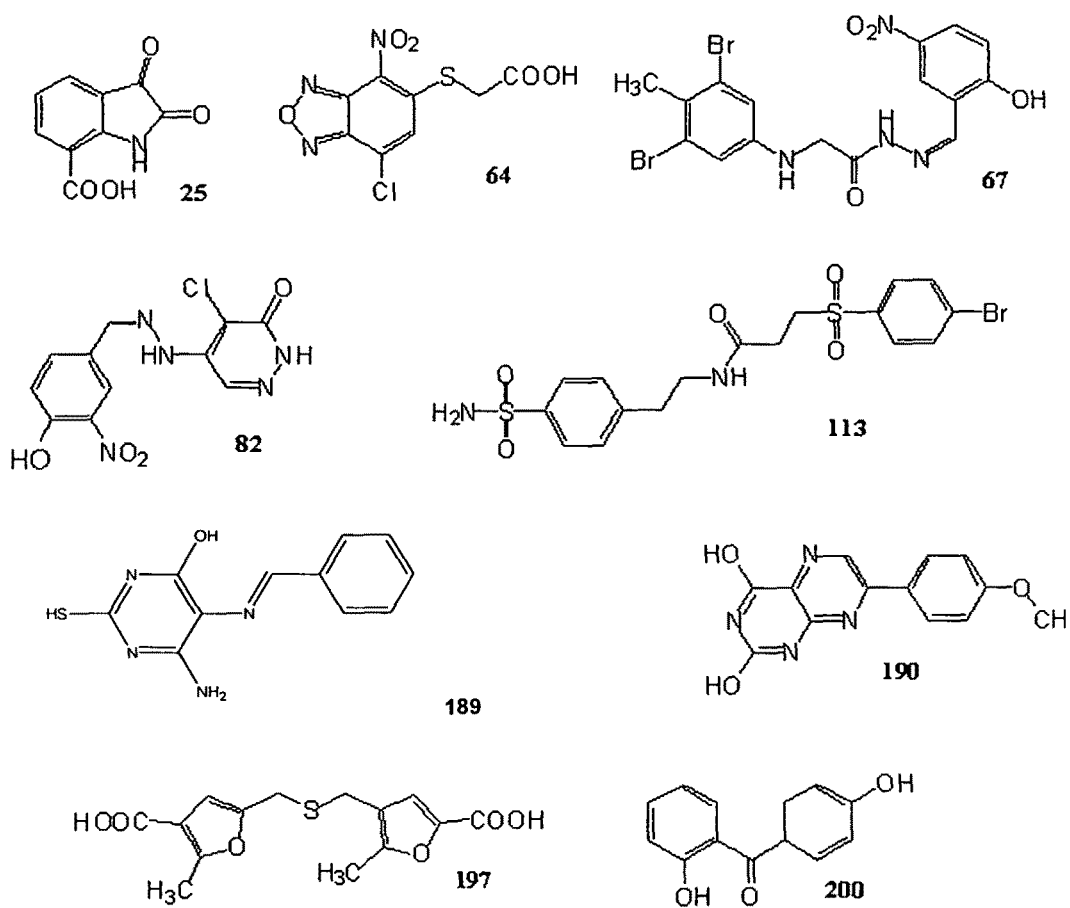

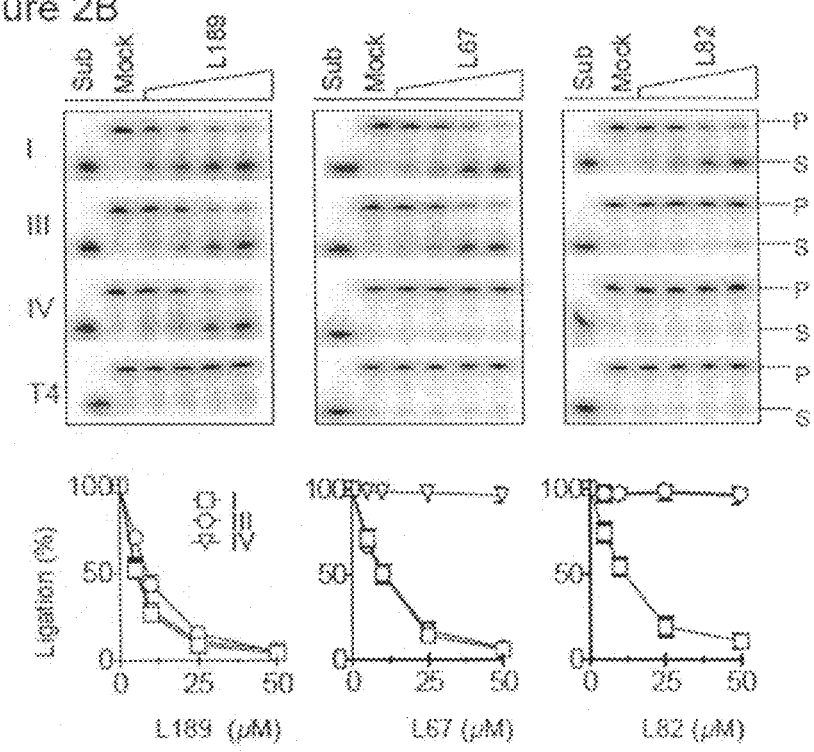

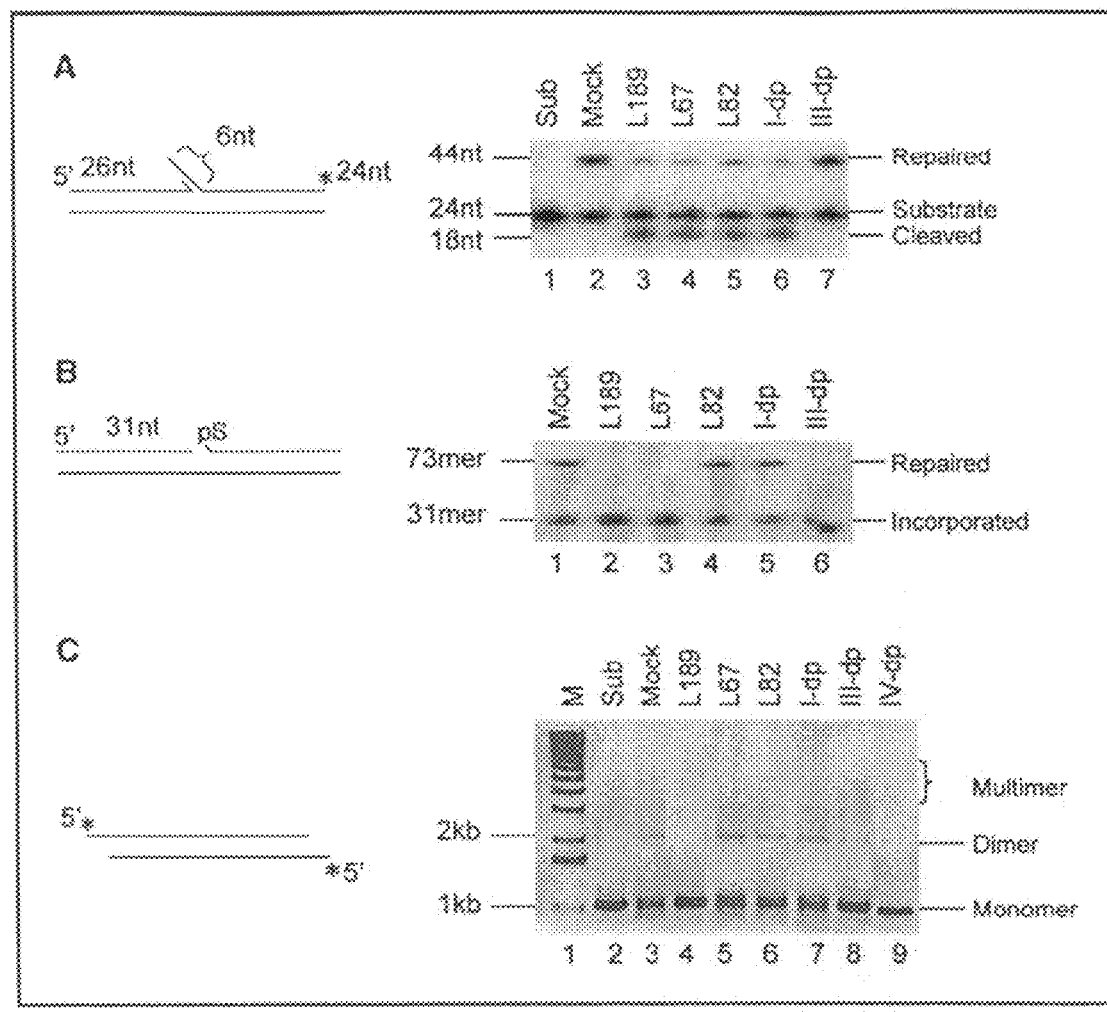

Growth inhibition induced by compounds 67 and 151

Compound 64 sensitizes cells to DNA damage

COMPOUNDS THAT INHIBIT HUMAN DNA LIGASES AND METHODS OF TREATING CANCER

CROSS REFERENCE TO RELATED APPLICATIONS

This application is a continuation-in-part of PCT/US2008/059931, filed Apr. 10, 2008, which claims the benefit of U.S. Provisional Application 60/911,000, filed Apr. 10, 2007, each of these applications being incorporated by reference in their entirety in this application.

STATEMENT REGARDING FEDERALLY SPONSORED RESEARCH OR DEVELOPMENT

This invention was made with the support of the U.S. government under Grant Numbers GM057479, GM047251, ES012512, CA092584 and CA102428 from National Institutes of Health (NIH). The U.S. government has certain rights in this invention.

NAMES OF PARTIES OF A JOINT RESEARCH AGREEMENT

Not Applicable

INCORPORATION BY REFERENCE OF MATERIAL SUBMITTED ON A COMPACT DISC

Not Applicable

BACKGROUND OF THE INVENTION

Despite many years of research, there still exists a compelling need to develop novel and more effective therapeutic strategies for human cancer. The use of many agents used in cancer treatment is limited because of their cytotoxic effects on normal tissues and cells. This is a particular concern for agents that kill cells by damaging DNA and/or inhibiting DNA replication. Moreover, it is becoming more and more evident that the simultaneous or sequential attack on different aspects of cancer cell metabolism by combinations of agents is more effective than the use of a single agent. This highlights the need to develop a wider variety of therapeutic agents that hit different molecular targets in cancer cells.

As mentioned above, therapeutic agents such as ionizing radiation and temozolomide, which damage DNA, have cytotoxic effects on normal tissues and cells as well as cancer cells. Despite the frequent use of agents that either damage DNA or inhibit DNA replication, there are relatively few available compounds that specifically target DNA repair and/or DNA replication-related proteins (1-3). Topoisomerase-I inhibitors, for example alter the capacity of a key DNA replication enzyme to proceed along an entire chromosome. Although cytotoxic, this class of compounds is currently being used to treat human cancer. There are also inhibitors of DNA damage response proteins, including the checkpoint kinase Chk1, poly(ADP) ribose polymerase, DNA dependent protein kinase, ATM kinase, MGMT and AP endonuclease (1-3) that are in preclinical or early clinical evaluation as cancer therapeutics. Applicants specifically contemplate that certain types of inhibitors of DNA repair pathways will have therapeutic utility because they will potentiate the cytotoxic effects of other treatments of cancer, for example, ionizing radiation and chemotherapeutic agents that damage DNA. This may permit specific targeting of tumors and/or the use of lower doses of DNA damaging agent, thereby reducing toxicity to normal tissues and cells. In addition, there is evidence that the DNA repair capabilities of cancer cells may be different than those of normal cells. For example, BRCA2-deficient cells established from individuals with an inherited predisposition to breast cancer are extremely sensitive to inhibitors of poly(ADP-ribose) polymerase because they are defective in homologous recombination (4,5). Thus, inhibitors of DNA repair proteins may specifically target cancer cells as compared to normal cell populations.

Under normal circumstances, the genome is propagated and maintained by the combination of a highly accurate DNA replication machinery and a network of DNA repair pathways. The increased incidence of cancer associated with DNA repair-deficient human syndromes illustrates the role of these pathways in protecting against deleterious genetic changes that contribute to cancer formation. There is growing interest in the identification of DNA repair inhibitors that will enhance the cytotoxicity of DNA-damaging agents because combinations of DNA-damaging agents and DNA repair inhibitors have the potential to concomitantly increase the killing of cancer cells and reduce damage to normal tissues and cells if either the damaging agent or the inhibitor could be selectively delivered to the cancer cells (2). Because DNA ligation is required during replication and is the last step of almost all DNA repair pathways, DNA ligase-deficient cell lines exhibit sensitivity to a wide range of DNA-damaging agents (6). Thus, DNA ligase inhibitors may have pleiotropic effects on cell proliferation and sensitivity to DNA damage.

DNA ligases catalyze the joining of interruptions in the phosphodiester backbone of double-stranded DNA, making them essential enzymes for DNA repair and replication. In addition, they are an indispensable reagent in molecular biology research for generating recombinant DNA. DNA ligases are members of the larger nucleotidyl transferase family that also includes RNA ligases and mRNA capping enzymes. In the first step of the ligation reaction, DNA ligases react with a nucleotide co-factor, either NAD+ or ATP, to form the covalent enzyme-AMP intermediate. Next the AMP moiety is transferred to the 5' phosphate termini in duplex DNA, forming the DNA adenylate intermediate. Finally, the non-adenylated enzyme catalyzes phosphodiester bond formation between the 3' hydroxyl and 5' phosphate termini.

BRIEF SUMMARY OF THE INVENTION

Because of their involvement in DNA replication and DNA repair, DNA ligase inhibitors are likely to be anti-proliferative and to potentiate the cytotoxicity of DNA damaging agents, properties that may have clinical utility in the treatment of cancer, in particular malignancies with an altered DNA damage response. DNA joining by a DNA ligase is required to link together Okazaki fragments during DNA replication and to complete almost all DNA repair pathways (6). Applicants' invention involves inhibitors of DNA ligases that: (i) inhibit cell growth and/or kill cells; (ii) potentiate the cytotoxic effects of many DNA damaging agents that introduce a wide variety of different types of DNA lesions, including agents such as ionizing radiation, topoisomerase inhibitors (irinotecan and topotecan), PARP inhibitors, 5-fluorouracil, mitomycin C, bleomycin, melphalan, cyclophosphamide, platinum compounds, cis-platinum and BCNU (Carmustine) and temozolomide that are currently being used to treat human cancer; and/or (iii) potentiate the cytotoxic effects of pro-apoptotic agents and inhibitors of signaling pathways that promote proliferation, for example a bcr-abl kinase inhbitor (imatinib (GLEEVAC)) that may be used to treat human cancer.

The combination therapy methods of the present invention are contemplated to be administered at the same time or at separate times to a subject in need thereof.

Applicants' invention includes methods for screening of individual chemical compounds, a synthetic chemical collection and/or a natural product library to identify compounds that inhibit human DNA ligase.

The human genome contains three genes, LIG1, LIG3 and LIG4, which encode ATP-dependent DNA ligases (6). These enzymes have unique cellular functions, but they also appear to have some functional redundancy. Although these enzymes have a conserved catalytic domain and use the same reaction mechanism, they are directed to participate in different DNA transactions by specific protein-protein interactions (6). DNA ligase I (hLigI) has a major role in the joining of Okazaki fragments during DNA replication and also in DNA excision repair. Based on the cellular phenotype of human DNA ligase I-deficient cells (7-9), specific inhibitors of DNA ligase I should inhibit cell growth and/or kill cells. Since cancer cells in general tend to be more proliferative than normal cells, it is conceivable that they will be more susceptible to the effects of DNA ligase I inhibitors. In support of this, it has been shown that human cancer lines grown either in vitro or as tumors in nude mice and human tumor specimens have elevated levels of DNA ligase I (10). In addition, human DNA ligase I-deficient cells are hypersensitive to DNA alkylating agents and an inhibitor of poly(ADP-ribose) polymerase (PARP), 3 aminobenzamide. (8-10). Applicants' invention involves DNA ligase I specific inhibitors that will preferentially kill rapidly proliferating cancer cells and potentiate the cytotoxic effects of DNA alkylating agents such as temozolomide and 1,3-bis (2-chloroethyl)-1-nitrosourea (BCNU) that are used clinically, and, when used in combination with PARP inhibitors (several of which are in clinical trials), will synergistically enhance cytotoxicity.

Several distinct DNA ligase polypeptides that function in nuclear DNA repair, mitochondrial DNA metabolism and germ cell development are encoded by the LIG3 gene (6). It appears that all cells express a single mRNA, DNA ligase III$\alpha$ mRNA that encodes mitochondrial and nuclear forms of DNA ligase III$\alpha$. In addition, there is an alternative splicing event in male germ cells that generates DNA ligase III$\beta$. Nuclear DNA ligase III$\alpha$ participates in the repair of DNA single strand breaks and the short patch subpathway of base excision repair. This appears to underlie the sensitivity of DNA ligase III-deficient cells to DNA alkylating agents and ionizing radiation (11,12). Applicants' invention also involves DNA ligase III inhibitors that will potentiate the cytotoxic effects of DNA alkylating agents such as temozolomide and BCNU, and ionizing radiation, all of which are used to treat human cancer. Furthermore, it has been shown that depletion of human DNA ligase III by RNAi disrupts mitochondrial function (13,14), raising the possibility that DNA ligase III inhibitors may cause cytotoxic effects via effects on mitochondrial function and may potentiate the effects of pro-apoptotic drugs. Since many tumors cells have alterations in energy metabolism, it is possible that they may be more susceptible to agents that target mitochondria. There is emerging evidence that DNA ligase I and DNA ligase III$\alpha$ participate in different subpathways of base and nucleotide excision repair and that these subpathways may be, at least in a part, functionally redundant (15,16). Applicants' invention also involves compounds that inhibit both DNA ligase I and DNA ligase III. These compounds will potentiate the cyto-toxicity of DNA damaging agents such as 5-fluorouracil, temozolomide, BCNU, platinum compounds and mitomycin C that introduce lesions that are removed by excision repair to a greater extent than compounds that are specific for either DNA ligase I or DNA ligase III.

The LIG4 gene product, hLigIV, completes the repair of DNA double strand breaks (DSBs) by nonhomologous end joining (NHEJ) and V(D)J recombination events that generate diversity in immunoglobulin and T-cell receptor loci during immune system development (6). Notably, DSBs are the major cytotoxic lesion introduced by ionizing radiation, which is the most commonly used modality in the treatment of human cancer. Furthermore, NHEJ is the major DSB repair pathway in human cells and inactivation of the LIG4 gene has a more severe effect than inactivation of genes encoding proteins that act earlier in the NHEJ pathway (17), suggesting that, once DSBs are committed to the NHEJ pathway, they cannot be recovered and repaired by pathways utilizing either DNA ligase I or DNA ligase III. Applicants' invention also involves DNA ligase IV inhibitors that will dramatically potentiate cell killing by ionizing radiation and radiomimetic drugs.

In the complex formed by hLigI on DNA with a non-ligatable nick, three hLigI domains encircle and interact with the nicked DNA duplex. (18) Two of these domains, an adenylation domain (AdD) and an OB-fold domain (OBD), are present in other DNA ligases and nucleotidyl transferases. In contrast, the DNA binding domain (DBD, residues Asp262 to Ser535) is restricted to eukaryotic ATP-dependent DNA ligases (6). Notably, the DBD is the predominant DNA binding activity within hLigI and stimulates joining in trans by a hLigI fragment containing the adenylation and OB-fold domains (18). Based on these properties, Applicants chose to focus on identifying compounds that bind to the DBD and inhibit hLigI activity by interfering with DNA binding.

Applicants' invention also includes the following.

Methods for using the inhibitors to delineate the molecular mechanisms of the DNA ligation reaction.

Methods for identifying the DNA ligase that completes different DNA repair pathways in cell extracts.

Methods for identifying the pathways involved in the repair of different DNA lesions using the ligase inhibitors in cell extract and cell culture assays.

Methods for treating cancer using compounds that inhibit human DNA ligases by inhibiting cell growth, killing tumorous cells and/or potentiate cell killing by DNA damaging agents.

Methods for treating cancer using compounds that inhibit human DNA ligase including treating epithelial-derived cancers, such as epithelia neoplams selected from the colon cancer, lung cancer, breast cancer, GI cancer, ovarian cancer and head and neck cancer.

Methods for treating cancer using compounds that inhibit human DNA ligase including treating hematological malignancies, such as hematological malignancy selected from the chronic and acute leukemias.

Methods for treating cancer using compounds that inhibit human DNA ligase including treating hematological malignancies, such as lymphomas.

The methods for treating cancer using compounds that inhibit human DNA ligase including treating skin cancer, melanoma, gliablastoma, neuroblastoma, sarcoma, colon cancer, breast cancer, cervical cancer, prostate cancer, pancreatic cancer, ovarian cancer, esophageal cancer, stomach cancer and lung cancer.

Identification and Characterization of Human DNA Ligase Inhibitors

One research focus has been to determine the cellular functions of the DNA ligases encoded by the human LIG1, LIG3 and LIG4 genes and to define the molecular mechanisms by which these enzymes are directed to participate in specific DNA transactions. Recently the structure of the catalytic domain of human DNA ligase I complexed with nicked DNA was determined (18). This was the first structure of a eukaryotic DNA ligase and the first structure of any DNA ligase complexed with DNA.

Attempts to identify human DNA ligase inhibitors by screening of chemical and natural product libraries have met with limited success. Previous attempts to identify DNA ligase inhibitors have involved in vitro screening of a chemical and a natural product library (19,20). Several compounds that inhibit DNA ligase I have been identified, but these compounds have not been extensively characterized in terms of their specificity and mechanism of action. A problem with screening of random chemical libraries using an in vitro DNA ligation assay is that it yields two classes of non-specific inhibitors; (i) molecules that bind to the DNA substrate; (ii) nucleotide analogs that inhibit not only ATP-dependent DNA ligases but also other nucleotide-dependent cellular enzymes. To circumvent these problems, Applicants used available structural information identifying the interfaces between DNA ligase I and nicked DNA (18) to design an in silico screening method for the identification of small molecules that disrupt the physical and functional interactions between DNA ligase and nicked DNA. In developing the screening methods, Applicants identified a binding pocket between residues His337, Arg449, and Gly453 that are located in the central region of the DBD and make direct contacts with the DNA substrate. Other residues comprising the binding site include Gly448, Arg451 and Ala455. (18, 21, 34-37) Based on amino acid sequence conservation, Applicants determined that it is likely that this binding pocket is relatively well conserved in human DNA ligases III and IV.

BRIEF DESCRIPTION OF THE SEVERAL VIEWS OF THE DRAWINGS

FIG. 1 shows the Structures of 9 of Applicants' inhibitors of human DNA ligases.

FIGS. 2A and 2B show the Specificity of Compounds 67, 82 and 189 as human DNA ligase inhibitors. FIG. 2A shows the IC50 values determined for Compounds 67, 82 and 189 using the fluorescence-based DNA joining assay for each of DNA ligases I, III and IV and T4 DNA ligase. FIG. 2B shows the effect of Compounds 67, 82 and 189 on DNA joining by human DNA ligases I, III and IV and T4 DNA ligase as determined using the radioactive gel-based assay.

FIG. 3A shows Human DNA ligases I, III and IV and T4 DNA ligase incubated with [$\alpha^{32}$P] ATP in the absence or presence of Compounds 67, 82 and 189 (100 μM). After separation by SDS-PAGE, the labeled ligase-AMP complex was detected by phosphorimaging. FIG. 3B shows labeled ligase-adenylate form of human DNA ligases I, III and IV and T4 DNA ligase incubated with a linear DNA substrate containing a single non-ligatable nick in the absence or presence of Compounds 67, 82 and 189 (100 μM). After separation by denaturing gel electrophoresis, the labeled DNA-AMP complex was detected by phosphorimaging. FIG. 3C shows non-adenylated human DNA ligases I, III and IV and T4 DNA ligase incubated with labeled DNA-AMP in the absence or presence of Compounds 67, 82 and 189 (100 μM). After separation by denaturing gel electrophoresis, labeled ligated DNA was detected by phosphorimaging.

FIGS. 4A, 4B and 4C show the effect of human DNA ligase inhibitors on replication and repair by human cell extracts. FIG. 4A shows a cell extract from the human cervical cancer cell line HeLa incubated with the indicated labeled flap substrate that mimics a common intermediate in DNA replication and long path base excision repair in the absence or presence of Compounds 67, 82, 184 and 189 (25 μM). After separation by denaturing gel electrophoresis, labeled fragments corresponding to the DNA substrate, cleaved product and fully repaired product were detected by phosphorimaging (28). FIG. 4B shows a HeLa cell incubated with labeled dTTP and the indicated linear substrate with an incised AP site that mimics an intermediate in short path base excision repair in the absence or presence of Compounds 67, 82 and 189 (25 μM). Lane 6, DNA ligase I was immunodepleted from the extract prior to the assay. Lane 7, DNA ligase III was immunodepleted from the extract prior to the assay. After separation by denaturing gel electrophoresis, labeled fragments corresponding to a single nucleotide insertion and fully repaired product were detected by phosphorimaging. FIG. 4C shows a HeLa extract incubated with a linear cohesive-ended 1 kb fragment with cohesive ends repair in the absence or presence of Compounds 67, 82 and 189 (25 μM). Lane 7, DNA ligase I was immunodepleted from the extract prior to the assay. Lane 8, DNA ligase III was immunodepleted from the extract prior to the assay. Lane 8, DNA ligases III and IV were immunodepleted from the extract prior to the assay. After separation by native agarose gel electrophoresis, the linear DNA substrate, re-circularized substrate and dimers trimers etc of the 1 kb substrate were detected by staining with ethidium bromide.

FIG. 5A shows different concentrations of Compounds 67 and 151 added to asynchronous subconfluent populations of HCT116 and MCF10A cells. FIG. 5B shows asynchronous subconfluent populations of HCT116 and MCF10A cells pre-treated with different concentrations of Compound 64 prior to the addition of 3 aminobenzamide (2 mM), MMS (100 μM) or cis-platinum (1 μM). After incubation for 5 days, cell growth was measured by the MTT assay (16).

FIG. 6A shows different concentrations of Compound 184 were added to asynchronous subconfluent populations of HCT116, MCF7 and MCF10A cells. Colonies were counted after two weeks. FIG. 6B shows different concentrations of Compound 151 were added to asynchronous subconfluent populations of HCT116 and MCF10A cells in the absence or presence of MMS (50 μM). Colonies were counted after two weeks. FIG. 6C shows different concentrations of Compound 189 were added to asynchronous subconfluent populations of HCT116 and MCF10A cells. After 1 hour, cultures were irradiated with 2 gray of ionizing radiation. Colonies were counted after two weeks. FIG. 6D shows different concentrations of Compound 67 were added to asynchronous subconfluent populations of HCT116, MCF7 and MCF10A cells. After 1 hour, cultures were irradiated with 2 gray of ionizing radiation. Different concentrations of Compound 67 were added to asynchronous subconfluent populations of HCT116 and MCF10A cells in the absence or presence of MMS (50 μM). Colonies were counted after two weeks.

DETAILED DESCRIPTION OF THE INVENTION

Figure 3A:
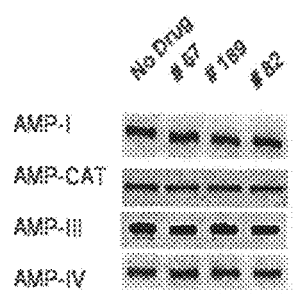
FIGS. 3A, 3B and 3C show the mechanism of action of human DNA ligase inhibitors.

Materials and Methods
Chemicals.
Compounds identified by CADD screening were purchased from ChemBridge, ChemDiv, MayBridge, MDD, Nanosyn, Specs, Timtec, and Tripos. 189 was from Specs, and 82 and 67 were from Chemdiv. Tenmillimolar stocks were prepared in DMSO and stored at −20° C. The molecular masses of three compounds 67, 82 and 189 were confirmed by mass spectrometry in the University of Maryland School of Pharmacy facility.

Proteins.
Recombinant human DNA ligase I was purified as described previously (22, 29). T4 DNA ligase was purchased from NEB.

DNA Joining Assays.
Candidate ligase inhibitors identified by CADD were assayed for their ability to inhibit hLigI and T4 DNA ligase using a high-throughput, fluorescence energy transfer-based DNA joining assay (22). Duplicate reactions (30 μL) containing 10 pmol of nicked DNA substrate and either 0.25 pmol of hLigI or 10 units of T4 DNA ligase were incubated in the presence or absence of 100 μmol/L of the putative inhibitor. DNA binding by the candidate DNA ligase inhibitors was measured by displacement of ethidium bromide from DNA as previously described (30).

A radioactive gel-based DNA ligation assay was performed as previously described (22). A 25-mer (5'-CGC CAG GGT TTT CCC AGT CAC GAC C-3') (SEQ ID NO: 1), and a 5'-[$^{32}$P] end-labeled 18-mer (5'-GTA AAA CGA CGG CCA GTG-3') (SEQ ID NO: 2) were annealed to a complementary 44-mer oligonucleotide, generating a linear duplex with a central nick. DNA joining reactions (30 μl) containing 0.5 pmol of labeled DNA substrate, and hLigI (0.02 pmol), hLigIIIβ (0.02 pmol), hLigIV/XRCC4 (0.1 pmol), or T4 DNA ligase (0.02 pmol) in ligation buffer were incubated in the absence or presence of ligase inhibitors at 25° C. for 30 min.

Assays for Steps 2 and 3 of the Ligation Reaction.
To analyze step 2 of the ligation reaction, labeled ligase-AMP intermediates (10 pmol (22)) were incubated overnight at 25° C. with an unlabeled nonligatable version (dideoxy residue at the 3'-terminus of the nick) of the DNA oligonucleotide substrate (10 pmol), either in the presence or absence of the ligase inhibitors (100 μmol/L).

To analyze step 3 of the ligation reaction, an adenylated labeled version of the 18-mer was prepared as described (24). The DNA substrate containing a preadenylated nick (0.5 pmol) and hLigI (0.05 pmol), hLigIIIβ (0.05 pmol), hLigIV/XRCC4 (0.1 pmol), or T4 DNA ligase (0.05 pmol) were incubated in ligation buffer without ATP, either in the presence or absence of the ligase inhibitors (100 μmol/L). Reactions were stopped by the addition of an equal volume of gel loading dye (95% formamide, 0.05% bromophenol blue, and 0.05% xylene cyanol). After heating at 95° C. for 5 min, DNA was separated by denaturing polyacrylamide gel electrophoresis. Labeled oligonucleotides were detected and quantitated in the dried gel by phosphorImager analysis (Molecular Dynamics).

Kinetic Analysis of Ligase Inhibitors.

To measure the initial rates of ligation, hLigI (0.05 pmol) was incubated with 0.5 to 100 pmol of the fluorescent, nicked DNA substrate and various concentrations of the ligase inhibitors. $K_i$ values were obtained from Lineweaver-Burk double reciprocal plots and curve-fitting using PRISM v3.03 (GraphPad).

Electrophoretic Mobility Shift Assay.

A labeled linear duplex with a nonligatable nick was incubated with hLig1 in ligation buffer (30 μL total volume) with or without ligase inhibitors for 120 min at 25° C. After the addition of an equal volume of native gel buffer [160 mmol/L Tris-HCl (pH 6.8), 20% glycerol, 1.4 mol/L 2-mercaptoethanol, and 0.05% bromophenol blue], samples were separated by electrophoresis through a 12% native polyacrylamide gel and detected in the dried gel by phosphorImager analysis.

Cell Extract Assay of DNA Replication and Repair.

Extracts were prepared from human cervical cancer HeLa cells as described previously (27, 31). For base excision repair (BER) assays, the extraction buffer contained 100 mmol/L of KCl, whereas for nonhomologous end-joining (NHEJ) assays, extraction buffer contained 400 mmol/L of KCl. Where indicated, DNA ligases were immunodepleted from the extracts as described (32) using protein A or G Sepharose beads (GE Healthcare) and anti-Lig1, anti-LigIII (GeneTex), or anti-LigIV (ABCAM) antibodies. Depletion was confirmed by immunoblotting.

A labeled 5'-flap substrate (0.1 pmol; (31)) was incubated with 20 μg of extract in the absence or presence of ligase inhibitors (100 μmol/L) at 25° C. for 5 min in ligation buffer (final volume, 50 μL). For short patch BER, a linear duplex containing a single uracil residue was preincised by treatment with uracil DNA glycosylase and APE1 (both from NEB) to generate a strand break with 3' hydroxyl and 5' deoxyribose phosphate termini. Reactions (50 μL) containing 0.3 pmol of the incised DNA substrate, 10 μCi of $[\alpha^{32}P]dTTP$, and 20 μg of extract either in the absence or presence of ligase inhibitors (100 μmol/L) were incubated at 25° C. for 2 min in ligation buffer. After separation by denaturing polyacrylamide gel electrophoresis, labeled oligonucleotides were detected in the dried gel by phosphorImager analysis (Molecular Dynamics).

To assay NHEJ (24), a 1 kb end-labeled BamHI fragment (0.1 pmol; (33)). and 20 μg of extract were incubated in ligation buffer (final volume, 20 μL), for 120 min at 25° C. either in the presence or absence of ligase inhibitors (100 μmol/L). DNA fragments were resolved by separation through a 0.8% agarose gel. Labeled DNA fragments were detected in the dried gel by phosphorImager analysis (Molecular Dynamics).

Cell culture assays. Normal human breast epithelial MCF10A cells were grown in DMEM/F-12 media (Gibco) with 20 μg/ml of EGF, 0.5 ug/ml of Hydrocortisone, 0.1 μg/ml of Cholera Toxin, 10 μg/ml of Insulin, 5% horse serum and 1% Pen/Strep. Human colon cancer HCT116 cells were grown in McCoy media (Gibco) with 10% FBS and 1% Pen/Strep. Human cervical cancer HeLa and breast cancer MCF7 cells were grown in low glucose medium (Gibco) containing 10% FBS and 1% Pen/Strep.

For survival assays, cells were plated in 6 well plates and grown either in the absence or presence of ligase inhibitors. Where indicated, either MMS (0-50 μM) was added to the medium or the cells were irradiated in a Cs-137 irradiator (0-2.5 Gy). After two weeks, colonies were stained with crystal violet (Sigma) and then counted.

FACS Analysis.

Cells ($1 \times 10^6$) were serum starved for 4 days prior stimulation with serum containing medium either with or without ligase inhibitors. At various time intervals, cells were trypsinized, washed with PBS and then fixed in 95% ethanol overnight at −20° C. After RNAse treatment and propidium iodide (Sigma) staining, the cell cycle distribution was determined by FACS in the Flow Cytometry Shared Service of the Marlene and Stewart Greenebaum Cancer Center.

Cell Proliferation Assays.

The ability of the compounds identified by CADD to inhibit proliferation of normal mammary epithelial MCF10A cells and colon carcinoma HCT116 cells was determined using a Biomek FX Laboratory Automation Workstation (Beckman Coulter, Inc., Fullerton, Calif.). On day 0, 20 μl of complete medium containing the appropriate number of cells (150-300) was plated per well of a 384-well tissue plate (Fisher Scientific, Hampton, N.H.) and incubated overnight at 37° C. with 5% CO2 and 90% humidity. Next day, day 1, compounds were prepared by serial dilution with complete medium to yield the concentration 100 μM, and 20 μl was added to each well containing 20 μl of medium and cells yielding the final concentration 50 μM in 40 μl volume. Plates were incubated for additional 3 days (days-2-5) until control cells (0.5% DMSO) reached ~70-80% confluency. On day 6, 40 μl of lysis/detection solution containing 1.2% Igepal CA-630 (Sigma) and a 1:1000 dilution of SYBR Green I nucleic acid stain (Molecular Probes, Eugene, Oreg.) was added to each well. Following an overnight incubation at 37° C., total fluorescence was measured using a Fluorostar Galaxy plate reader with a 485 nm excitation filter and 520 nm emission filter set (BMG Labtech, Inc., Durham, N.C.). Data was exported to a custom program that determined growth inhibition by dividing each individual fluorescence value by the average of fluorescence values obtained with cells treated with DMSO alone. Compounds that showed at least 40% growth inhibition compared with the DMSO-only controls inhibition of one or both of the cell lines were scored as "hits".

The activity of hits from the initial screen was further validated using the MTT assay. Briefly, MCF10A and HCT116 cells were seeded in 96 well plates at 300 and 1200 cells per well, respectively, and allowed to adhere overnight. The following day, serial dilutions of compounds in media were added to the cells in a final volume 200 μl. After incubation for 5 days, MTT reagent (3-(4,5-dimthylthiazol-2-yl)-2,5-diphenyltatrazolium) was added and incubation was continued for 4 h. Formazan crystals generated by reduction of the MTT reagent in mitochondria were solubilized with isopropanol prior to the measurement of absorbance at 560 nm wavelength in a plate reader.

Immunocytochemistry.

The effect of ligase inhibitors on the subcellular distribution of tubulin was examined by fluorescence microscopy. Cells grown on the chamber slides were washed with PBS, fixed and then permeabilized on ice for 10 min in 2% formaldehyde and 0.1% Triton X-100. After washing with PBS, cells were incubated for 15 min with 1% BSA (Sigma-Aldrich) and then incubated with tubulin antibody (Invitrogen) for 2 h. Cells were washed with PBS prior to incubation with the AF488 conjugated secondary antibody (Invitrogen) for 1 h. After washing with PBS, cover slips were mounted on the slides with mounting media containing DAPI (Invitrogen). Cells were observed under a fluorescence microscope (Nikon Eclipse 80i) using 60× oil immersion lenses. Images were processed using NIS-Elements BR2.30 software. Methods CADD Screening.

Figure 10:
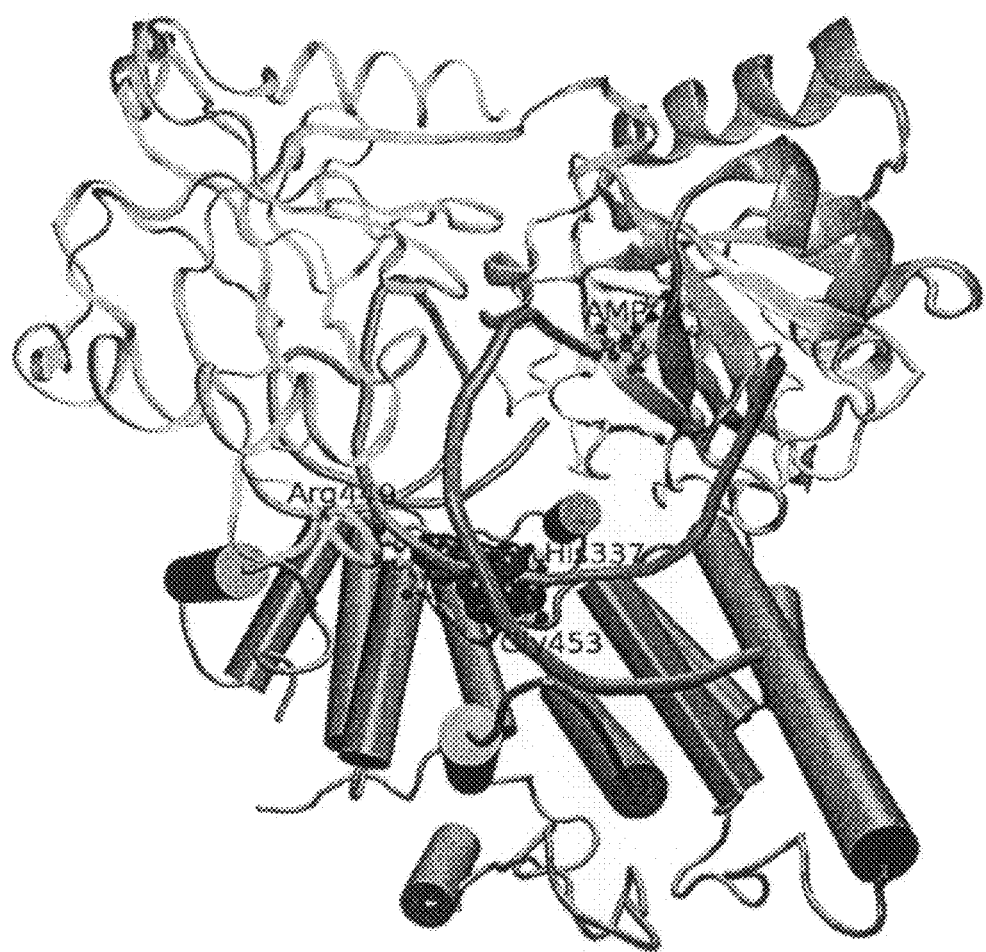
FIG. 10. The DNA substrate (thin tube) is encircled by three domains of human DNA Ligase I, i.e. the DNA binding domain (DBD) containing residues Asp262-Ser535 (connected large tubes-bottom), the adenylation domain (AdD) Pro536-Asp748 (wide ribbon-upper right), and the OB-fold domain (OBD) Tyr749-Ser901 (narrow ribbon-upper left). The AMP cofactor (in CPK representation) is located in AdD and the putative binding site on DBD is represented by red spheres and the three residues defining the binding pocket, His337, Arg449 and Gly453, are shown in CPK representation.

The in silico identification of compounds with a high probability of binding to and inhibiting DNA ligase involved the following steps:

Identification of a putative ligand binding site on the interface between the DBD and bound DNA (FIG. 10);

molecular dynamics (MD) simulations for the generation of multiple protein conformations to address the flexibility of the binding site in the screening process;

preliminary screening of compound set, secondary docking of compounds from the preliminary screen against the crystal structure and the MD generated structures, and final selection of compounds for experimental assay.

Protein Structure Preparation.

The crystal structure of hLigI, obtained from the protein database bank (38) (PDB, http://www.rcsb.org/) (PDB identifier 1x9n)6 was truncated, keeping only the DBD. Hydrogen atoms were then added followed by local energy minimization with the program CHARMM (39). The minimization involved 100 conjugate gradient (CONJ) steps with the positions of atoms identified in the crystallographic structure fixed at their experimental values. Calculations were performed using the CHARMM all-atom protein force field including the CMAP modification (40, 41) with default cutoffs for the non-bond interactions. The resulting DBD structure was used in the preliminary docking (see below).

To obtain multiple conformations of the protein for secondary docking, an MD simulation was performed for 5 ns on the DBD using stochastic boundary conditions (42). First, the structure was minimized for 200 Steepest Descent (43) (SD) steps in vacuum. The binding region was then solvated by overlaying the protein with a 35 Å water sphere centered on the geometric center of the three residues, His337, Arg449, and Gly453, defining the binding pocket (see below). Water molecules within 2.8 Å to any protein non-hydrogen atom were removed. A test equilibration MD simulation showed a tendency for the water to move towards the protein and away from the surface of the sphere associated with the deletion of water overlapping the protein. Therefore, the water ball was assigned a boundary potential of 30 Å for all remaining calculations. All atoms were divided into three radial shells, i.e. the central region, an edge region from 26 to 30 Å, and an outer region beyond 30 Å, which was comprised of only protein atoms. Atoms in the outer region were constrained to their energy-minimized positions, atoms in the edge region were harmonically restrained with a force constant of 5 kcal/mol/Å and the central region was not subject to any type of restraints. The density of the water sphere was maintained using a quartic potential via the Miscellaneous Mean Field Potential (MMFP) module (44, 45) in CHARMM. Parameters defining the potential were force 0.25, droff 28.5, and p1 2.25, which yields a local well of −0.31 kcal/mol at the edge of the sphere. Non-bond interaction lists were heuristically updated out to 14 Å with the electrostatic and Lennard Jones (LJ) interactions truncated at the range of 10 to 12 Å using force switching (46). Following a 500 step SD minimization the protein was subjected to a 5 ns MD simulation at 300 K using the velocity Verlet (VVER) (47) integrator, an integration time step of 2 fs, and SHAKE to constrain all covalent bonds involving hydrogen atoms (48). Coordinates were saved every 5 ps, yielding a total of 1000 conformations from which additional structures were selected for the secondary docking. Selection of conformations for docking was performed via clustering based on pairwise root-mean square differences of the position of residues defining the binding site, i.e. the residues Glu300-Arg305 on the loop between helixes 3 and 4 according to the helix order in 1x9n.pdb, Ser334-His337 at the end of helix 5, Pro341-Asp351 on the loop following the short helix 6, and residues Gly448-Glu456 on the loop between helixes 12 and 13. Clustering was performed with NMRCLUST (49) with representative structures from the four biggest clusters chosen and used in the secondary docking.

Identification of Putative Binding Site.

A putative DNA binding site within the DBD was identified using the sphere sets used in the program DOCK (36) in combination with residues implicated in DNA binding by x-ray crystallography.

Three residues focused on, His337, Arg449, and Gly453, that are located in the central region of the DBD and make direct contacts with the DNA substrate are shown in FIG. 10. Other residues comprising the binding site include Gly448, Arg451 and Ala455.

Generation of the sphere set used the minimized crystallographic structure, with the hydrogen atoms deleted, to compute the Connolly solvent accessible surface (50, 51) via the subroutine DMS which is implemented in the program MIDAS (52) (recently updated to Chimera (53). The solvent accessible surface was computed via DMS using the surface points of the probe sphere as required when hydrogen atoms are not present, with the density of points set to 0.5 as suggested for proteins. Second, spheres ranging from radii 1.2 Å to 4 Å, complementary to the protein surface were generated by the subroutine SPHGEN implemented in the package DOCK (36). Each sphere contacts, two protein surface points and lies on the normal of one of the two points. This procedure generates a very large number of spheres, which are filtered by selecting only the largest sphere associated with each surface atom. Next, spheres within 8 Å of all three reference residues, His337, Arg449, and Gly453, were selected and selected spheres on the periphery of the putative binding pocket manually deleted. This yielded the final sphere set shown in FIG. 10 which was used to direct the in silico database screening.

In Silico Compound Databases.

An in-house database of more than 4.3 million low-molecular weight compounds has been developed in the University of Maryland Computer-Aided Drug Design Center. This database is comprised of three types of files, i.e. 2D SD format files originally from the commercial vendors, 3D MOL2 format files for docking, and binary MDB format files for use in the program MOE (Chemical Computing Group Inc. Montreal, Canada). Compound preparation included removal of the smaller components in entries containing salts (e.g. counter ions), adding hydrogen atoms, assignment of the protonation state, geometry optimization using the MMFF94 (54, 55) force field level with either the SYBYL (Tripos Associates, St. Louis, Mo.) or MOE (Chemical Computing Group, Canada), and assignment of atomic partial charges based on CM2 charge model computed at the semi-empirical quantum chemical AM1 level using AMSOL (56, 57). Preliminarily screening used approximately 1,500,000 compounds from vendors chosen based on their reliability with respect to availability of compounds. Vendors include Chembridge (371,000), Chemdiv (750,000), Maybridge (60,000), MDD (33,000), Nanosyn (47,000), Specs (232,000), Timtec (165,000) and Tripos (80,000), where the values in parentheses represent the approximate number of compounds associated with each company. Recently, the compounds in the collections from these companies have been shown to typically have drug like characteristics (58).

Docking and Final Compound Selection.

Docking computations were performed using DOCK4.0 (34) with parameters previously used in our laboratory (37, 59, 60). Kollman partial atomic charges for the DBD were assigned using the program SYBYL. Database searching in DOCK is performed via a fragment-based build up procedure (61). In this approach one or more anchor fragments (e.g. rigid units, such as rings, with 5 or more atoms) are overlaid on the spheres in 200 orientations. The remainder of the ligand is then built layer by layer, with a rotation about each added bond in 10° increments to identify the most favorable orientation based on the total ligand-protein interaction energy. Thus, the docking procedure accounts for ligand flexibility while the protein is treated as rigid. From the preliminary docking using only a single conformation of the protein, the top 50,000 compounds were selected based on the normalized van der Waals attractive (Va) energy, as described below. These compounds are then subjected to a second round of docking where the crystallographic plus four additional conformations of the protein from the MD simulation (Table 1) were targeted to account for protein flexibility. The ligands were separately docked into each protein conformation, with the most favorable score from all five conformations assigned to rank that ligand. The score used in the second docking run is the total interaction energy including electrostatic and van der Waals interactions. In addition, the ligand was subjected to additional optimization by increasing the maximum anchor fragment orientations from 200 to 500, performing minimization of the anchor at each cycle of ligand buildup and minimizing the 5 inner layers upon addition of each layer of the ligand.

Table 1. The RMSD Values in Å Between Each Pair of the Five Conformations Used for Database Screening, Including the Crystal Structure (1x9n) and the Four MD Generated Conformations (C2-C5). Only Residues Related to the Binding Region are Used in the Calculation.

|      | 1 x 9n | C2   | C3   | C4   | C5 |
|------|--------|------|------|------|----|
| 1 x 9n | 0    |      |      |      |    |
| C2   | 2.18   | 0    |      |      |    |
| C3   | 2.29   | 1.82 | 0    |      |    |
| C4   | 2.23   | 1.65 | 1.42 | 0    |    |
| C5   | 2.45   | 2.15 | 1.74 | 1.43 | 0  |

Compound clustering was performed using the Tanimoto similarity index (62, 63) based on BIT_MACCS fingerprints (64) which is implemented in the MOE software package. The BIT_MACCS fingerprints are used to compute the pairwise Tanimoto similarity matrix S which contains the similarity metric between the molecular fingerprints of compounds i and j. The matrix element $S(i,j)$, i.e. the Tanimoto coefficient (Tc) is defined as $Tc=c(i,j)/u(i,j)$, where $c(i,j)$ is the number of common features in the fingerprints of molecule i and j, and $u(i,j)$ is the number of all features in the union of the fingerprints of molecule i and j (65). Two compounds are regarded as similar if $S(i,j)$ is equal to or greater than a predefined similarity threshold. Then, from matrix S, another binary matrix O is created where each matrix element $O(i,j)$ has the value 1 if $S(i,j)$ is equal to or greater than the predefined similarity threshold, or 0 otherwise. Two molecules i and j are then grouped into a cluster if the overlap between the two row vectors $O(i)$ and $O(j)$ is greater than or equal to a predefined overlap threshold. In the present work a similarity threshold of 70% and an overlap threshold of 40% were used.

Results

In Silico Database Screening.

A putative DNA binding pocket within the DBD of hLigI was chosen as the target for a multi-tiered in silico database screening procedure, based on regions of the DBD in direct contact with the DNA in the X-ray structure of hLigI complexed with nicked DNA (FIG. 10). In the first step of the screen to identify compounds with a high probability of binding to the DBD of hLigI, ligand posing of 1.5 million compounds was based on the total interaction energy between the ligands and the protein, with ligand ranking performed using the normalized van der Waals attractive (Va) energy. Use of the Va energy parameter selects for compounds with significant steric overlap with the binding pocket and avoids compounds with highly favorable electrostatic interactions that do not fit well into the pocket. In addition, normalization procedures correct for the tendency of compound selection based on interaction energies to bias towards high molecular weight (MW) compounds (66).

Figure 11:
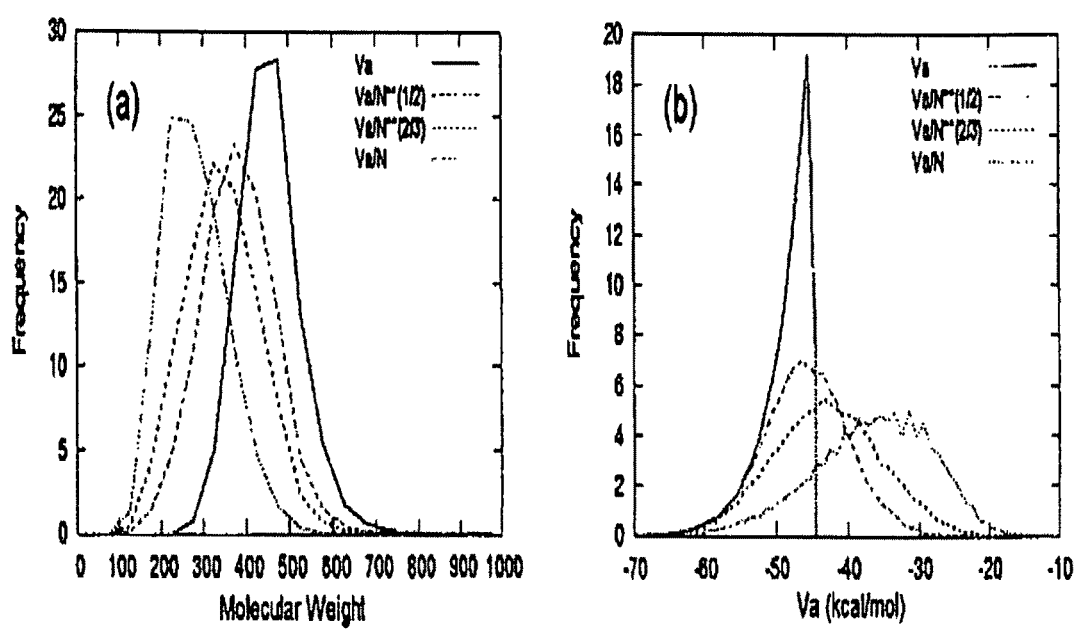
FIG. 11. Distributions of (a) the molecular weight and (b) the van der Waals attractive energy Va of the 50,000 compounds selected, via different normalizations by N the number of heavy atoms of the compound, from the preliminary screening. The normalization $Va/N^{2/3}$, as shown by the blue dotted line is used to select compounds.

Distributions of MW using different normalization procedures and the distributions of normalized scores are shown in FIGS. 11A and 11B, respectively. Based on N2/3 normalization, a total of 50,000 compounds with a molecular weight distribution centered around 300 Daltons were selected for further analysis.

Figure 12:
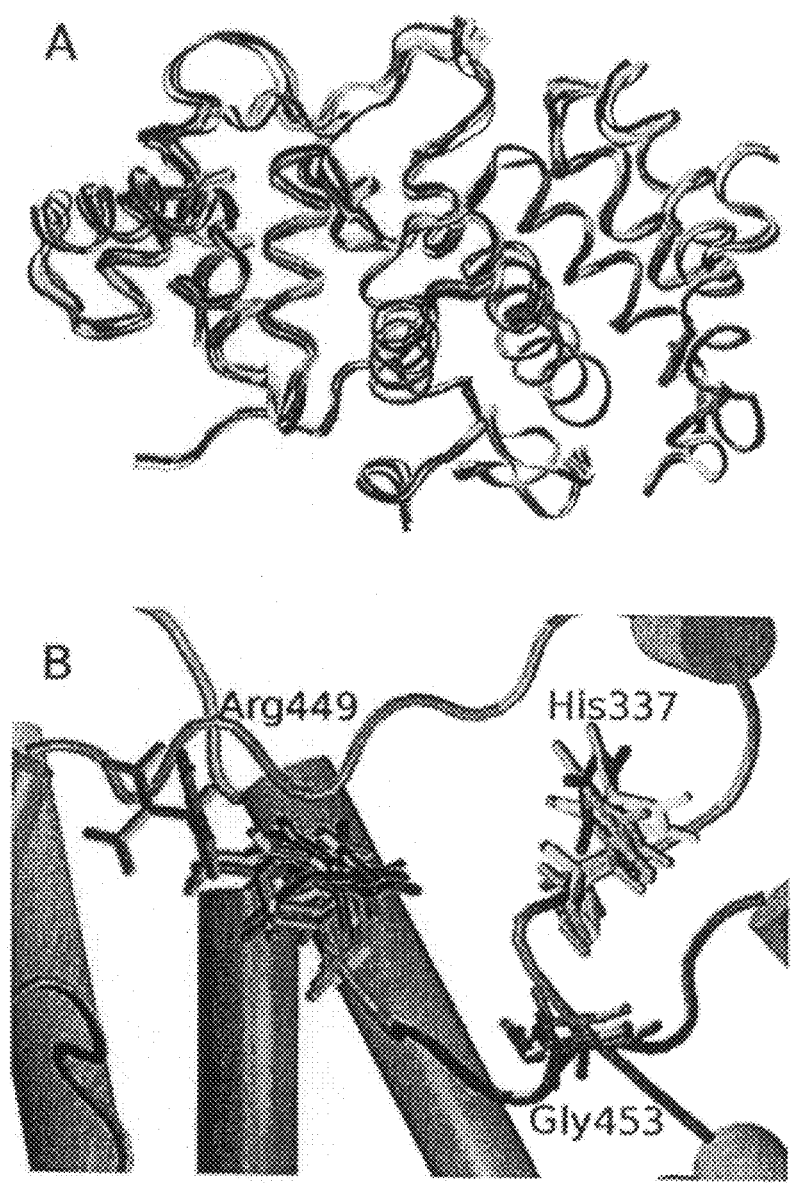
FIG. 12. (A) Alignment of the crystal structure and four conformations selected from the 20 ns MD simulation. (B) Orientations of three of the residues lining the binding site.

Secondary screening of the 50,000 compounds applied additional energy minimization during docking and partially addressed protein flexibility (67, 68) via the inclusion of four additional, structurally diverse conformations obtained from an MD simulation. Overall, the five conformations of the DBD are similar (FIG. 12A), indicating that significant structural changes in the protein did not occur during the MD simulation. However, a detailed comparison of the orientation of the residues lining the binding region shows that there is significant diversity across the five conformations. In FIG. 12B, the orientation of three residues, His337, Arg449, and Gly453, located in the central site of the binding region are shown. Table 1 gives the root mean square deviations (RMSD) of the residues in binding region, including residues Glu300-Arg305, Ser334-His337, Pro341-Asp351, and Gly448-Glu456. Differences in the RMSD values between the crystal structure and the four conformations from MD simulation range from 1.4 to 2.5 Å, indicating significant conformational variation in the binding pocket.

Figure 13:
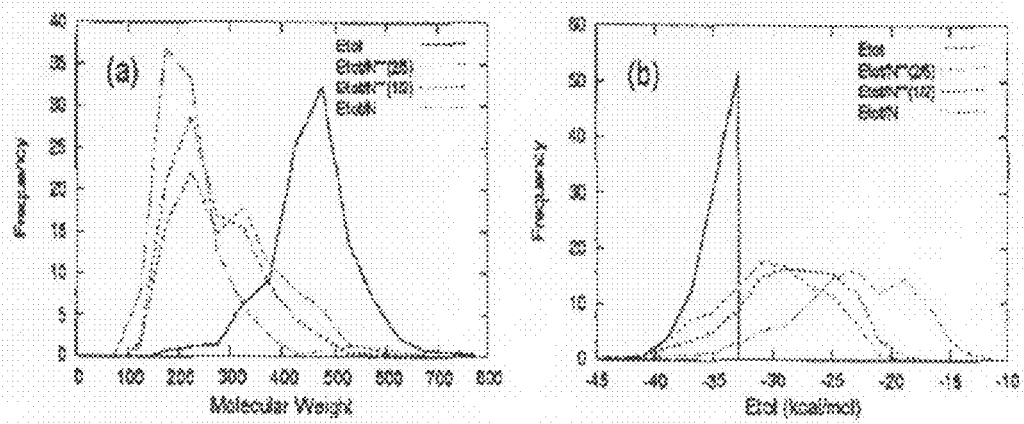
FIG. 13, Distributions of (a) the molecular weight and (b) the total interaction energy, Etot, of the 1000 compounds selected via different normalization schemes from the secondary docking.

Compounds were ranked based on the most favorable normalized total interaction energy of each ligand against the five protein conformations. At this stage the total interaction energy includes electrostatic interactions as well as steric considerations in the selection process. The MW and energy distributions for different powers of N normalization of the 1000 compounds with the most favorable normalized total interaction energies are shown in FIGS. 13A and 13B. These compounds were selected based on $E/(N^{**}(2/5))$ normalization, yielding a MW distribution consistent with compounds known to be pharmacologically active or used in lead compound optimization studies. (69, 70)

Figure 14:
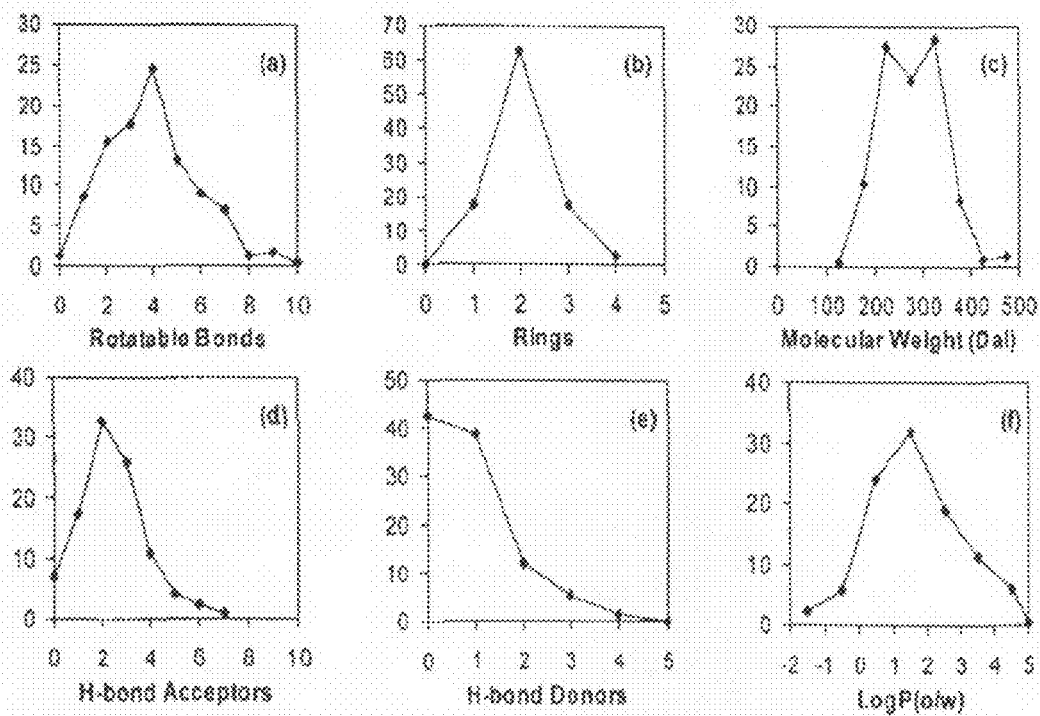
FIG. 14. Distributions of physical and molecular properties of the 233 selected compounds.
Figure 15:
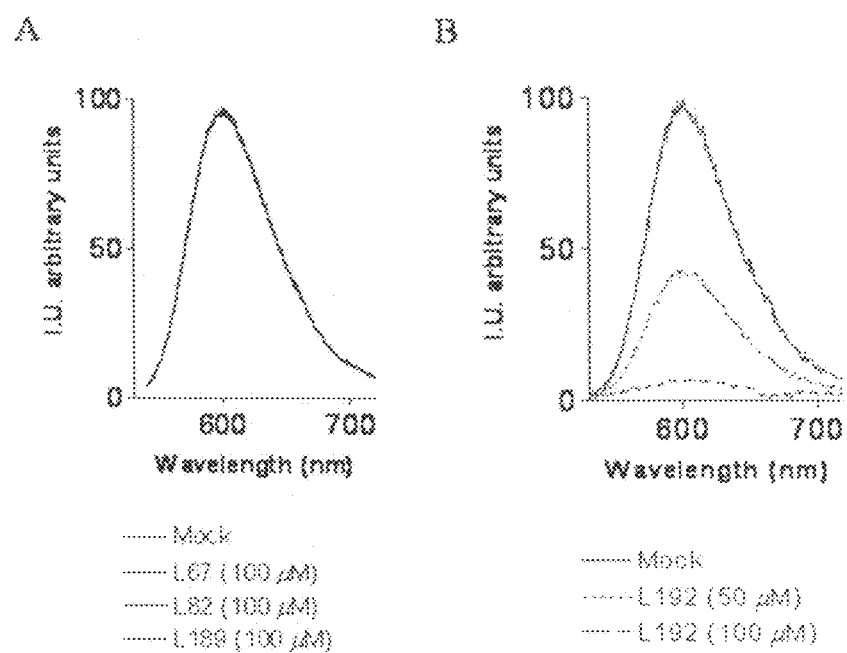
FIG. 15. Assessment of inhibitor and DNA interaction by EtBr replacement assay. There is no binding of 82, 67 and 189 with DNA (A). In contrast, EtBr is replaced to DNA binding by 192 in a concentration (0, 50, 100 μM) dependant manner (B).

Final selection of compounds for in vitro biochemical assays were chosen to maximize chemical diversity and based on their drug or lead-like compound properties (69, 70). Diversity was maximized by clustering the compounds based on chemical fingerprints using the Tanimoto similarity index. This yielded approximately 200 clusters of chemically similar compounds, with 1 or 2 compounds from each cluster selected based on drug- or lead-like compound properties as defined by Lipinski's rule of 5. (71) These rules include molecular weight (MW<500), adequate solubility expressed by the octanol/Water partition coefficient (−5<log P(o/w)<5), number of hydrogen bond acceptors (H-bond acceptors<10), number of hydrogen bond donors (H-bond donors<5), number of rotatable single bonds (Rotatable bonds<10), and number of rings (Ring<5). The final compounds typically also satisfy the slightly stricter rules of Oprea (69). However, for clusters in which the criteria were not met, compounds were still selected for experimental assay. From this process, 233 compounds were selected for experimental testing (Table 2). Distributions of the physical and molecular properties of the 233 compounds are presented in FIG. 14, showing them to indeed fulfill Lipinski's Rule of 5.

The method for screening compounds comprises testing the compound for the ability to inhibit human DNA ligases I, III and IV with a high throughput fluorescence-based ligation assay. In this assay, phosphodiester bond formation covalently links together two oligonucleotides, one of which is a fluorescent donor AF488 that is 11 nucleotides from the 3' terminus and the other contains a fluorescence acceptor and quencher, BHQ1 that is 15 nucleotides from the 5' terminus. When these oligonucleotides are present in separate duplexes and in the same nicked or intact duplex, there is no significant quenching of fluorescence because the donor and acceptor are too far apart. As single-strands neither the AF488 oligonucleotide nor the BHQ1 oligonucleotides have significant secondary structure. However, when these oligonucloetides are ligated together, the resultant single strand forms a stable hairpin structure, in which the AF488 and BHQ1 groups are very close together, resulting in efficient intra-molecular quenching of fluorescence. Thus, in the DNA joining assay, the DNA substrate is denatured after incubation with the DNA ligase and then renatured in the presence of a 20-fold excess of an oligonucleotide that is identical to the ligated strand containing the fluorescent door and acceptor except that it lacks these modifications. Using this assay, DNA joining, which results in reduced fluorescence at 518 nm, can be measured rapidly, quantitatively and with high-throughput using a fluorescence plate reader.

Experimental Assays.

192 out of the 233 compounds were screened for activity in high throughput in vitro DNA ligase assays and cell culture assays (Table 3). The screens, described in detail below, were carried out in parallel.

(1) In Vitro DNA Ligase Assay.

Applicants developed a novel high throughput fluorescence-based ligation assay by modifying the sequence of the oligos to optimize hairpin formation by the single strand ligated product of the high throughput fluorescence-based ligation assay of Chen et al (22). The ability of the 192 compounds to inhibit human DNA ligases was tested. Compound stock solutions, which were 10 mM in 0.5% DMSO, were diluted in 0.5% DMSO. Human DNA ligases I and III were assayed with a nicked DNA substrate whereas as the substrate for human DNA ligase IV was two oligonucleotide duplexes with short complementary single strand ends.

In the fluorescence-based high throughput ligation assay, 15 of the 192 compounds inhibited hLigI by >50%.

In addition, to identify compounds that may be non-specific inhibitors of DNA joining, the 192 compounds were also assayed for their ability to inhibit bacteriophage T4 DNA ligase, an enzyme that utilizes the same reaction mechanism as hLigI, has similar adenylation and OB-fold domains but lacks a DBD domain. (6) Although this is also an ATP-dependent DNA ligase, it lacks the domain containing the binding pocket targeted by the in silico screen. Compounds that inhibited T4 DNA ligase were eliminated as non-specific inhibitors that most likely bind to the DNA. The results of the screen are shown in Tables 4, 5, 5A and 6.

Of the 15 compounds that inhibited hLigI (25, 32, 64, 67, 82, 113, 123, 175, 180, 189, 190, 192, 197, 200 and 202) (Table 4), 6 were active against T4 DNA ligase by >50%. Thus, the in silico screen yielded 9 compounds that specifically inhibit hLigI, a hit rate of about 5%.

One mechanism by which a compound may non-specifically inhibit human DNA ligase is by binding to DNA rather than the ligase thereby interfering with the enzyme-substrate interaction. In accord with this idea, 192, which inhibits both hLigI and T4 DNA ligase (Table 4), reduced DNA binding of the DNA intercalating agent ethidium bromide (FIG. 6B) whereas three other compounds, 67, 82 and 189 that inhibit hLigI but not T4 DNA ligase (Table 4)), had no effect on DNA binding by ethidium bromide (FIG. 6A) indicating that 67, 82 and 189 do not bind DNA.

Because the DNA binding domains of human DNA ligases III and IV and closely related to the DNA binding domain of human DNA ligase that was used for the in silico screening, the 192 compounds identified by the in silico screening were also assayed for activity against human DNA ligases III and IV.

The in vitro screen identified compounds that are specific for each of one the human DNA ligases (DNA ligase I, DNA ligase III and DNA ligase IV) and identified compounds that inhibit two or more of the enzymes. The in vitro screen yielded three compounds that are specific for DNA ligase I (Compounds 1, 43, 82, 151, 184, 190), one compound that is specific for DNA ligase III (Compound 209), three compounds that are specific for DNA ligase IV (Compounds 93, 122, 215), four compounds that specifically inhibit DNA ligases I and III (Compound 25, 67, 200, 213), one compound that specifically inhibits both DNA ligases I and IV (Compound 113) and three compounds that inhibit all three human DNA ligases (Compound 64, 189, 197). See Table 5A for the In Vitro and In Vivo properties of the above grouped human DNA ligase inhibitors.

(ii) In Vivo Cell Culture Assays.

The 192 human DNA ligase inhibitors were screened in parallel for effects on proliferation and the ability to potentiate the effects of several DNA damaging agents using two cell human lines, a colon cancer line HCT116 and a normal breast epithelial cell line MCF10A using a Biomek FX Laboratory Automation Workstation as described (23). The DNA damaging agents used, methyl methanesulfonate (MMS), camptothecin, cis-platinum, 3 aminobenzamide and ionizing radiation, are representatives of classes of agents used to treat cancer. Briefly, HCT116 and MCF10A cells were plated in 96 well plates such that the cultures were about 80% confluent after 5 days incubation. Compounds were added to the cultures at either 15 μM or 50 μM 1 day after plating. After incubation for 3 days, cell lysed in a solution containing 1.2% Igepal CA-630 and SYBR green that stains DNA (1:1000, Molecular Probes, Eugene, Oreg.). Subsequently, fluorescence was measured per well. The studies with DNA damaging agents were performed as follows. Cells were pre-incubated with the compounds at 75 µM for 1 hour prior to the addition of camptothecin (2 nM), cis platinum (1 µM), 3 AB (2 mM) or MMS (100 µM) that resulted in dilution of the compound to a final concentration of 50 µM. For ionizing radiation, cells were pre-incubated with the compounds at 50 µM for 1 hour prior to exposure to 2 gray of ionizing radiation. Cultures were incubated for 3 days and then treated as above. The results of the in vivo cell culture assays are summarized in Table 6.

Among the 192 compounds, seven inhibit proliferation of one or both cell lines with an $IC_{50}$<20 µM (Compounds 16, 67, 78, 151, 165, 180, 195). At 50 µM 16 compounds inhibited proliferation of one or both cell lines by more than 40%. There was considerable overlap with the compounds identified as in vitro inhibitors of human DNA ligases. Notably, the nine of the in vitro inhibitors (compounds 43, 64, 67, 82, 151, 184, 189, 190, and 213) also inhibited cell proliferation.

In addition, three compounds act as radiosensitizers (Compounds 64, 151, 105), three compounds enhance the cytostatic effect of MMS (Compounds 67, 78, 151) and two compounds act synergistically with PARP inhibitors (Compound 64, 67).

Based on the combined results of the in vitro and in vivo screens, compounds 1, 25, 43, 64, 67, 78, 82, 93, 105, 113, 122, 151, 180, 184, 189, 197, 209, 213 and 215 were chosen for further analysis.

The specificity and inhibitory effects of a subset of these compounds were quantitated using the fluorescence-based ligation assay (22) and in gel-based assays (24).

The effect of Compounds 67, 82 and 189 on DNA joining by human DNA ligases I, III and IV and T4 DNA ligase was determined. The IC50 values determined for Compounds 67, 82 and 189 using the fluorescence-based DNA joining assay (22) are shown for each of the DNA ligases. See FIG. 2A. The effect of Compounds 67, 82 and 189 on DNA joining by human DNA ligases I, III and IV and T4 DNA ligase was determined using the radioactive gel-based assay (24). See FIG. 2B. Representative gels of DNA ligation assays. The results of three independent experiments are shown graphically. For clarity, the data for T4 DNA ligase, which was not significantly inhibited, has been omitted (hLigI, □; hLigIIIβ, ○; hLigIV/XRCC4, upsidedown triangle).

In addition, the mechanism of inhibition was determined. DNA ligases utilize a three step reaction to catalyze phosphodiester bond formation. In the first step, human DNA ligases interact with ATP to form a covalent enzyme-adenylate complex. When this intermediate reacts with a DNA nick, the AMP group is transferred to the 5' phosphate terminus of the nick, forming a DNA-adenylate intermediate. Finally, non-adenylated DNA ligase catalyzes phosphodiester bond formation in a reaction that is dependent upon the hydroxyl group at the 3' terminus of the nick and results in release of the AMP group (6).

Human DNA ligases I, III and IV and T4 DNA ligase were incubated with [$\alpha^{32}$P] ATP in the absence or presence of compounds 67, 82 and 189 (100 µM). After separation by SDS-PAGE, the labeled ligase-AMP complex was detected by phosphorimaging.

Compounds 67, 82 and 189 did not inhibit the first step of the ligation reaction, which is DNA independent (FIG. 3A).

Figure 3B:
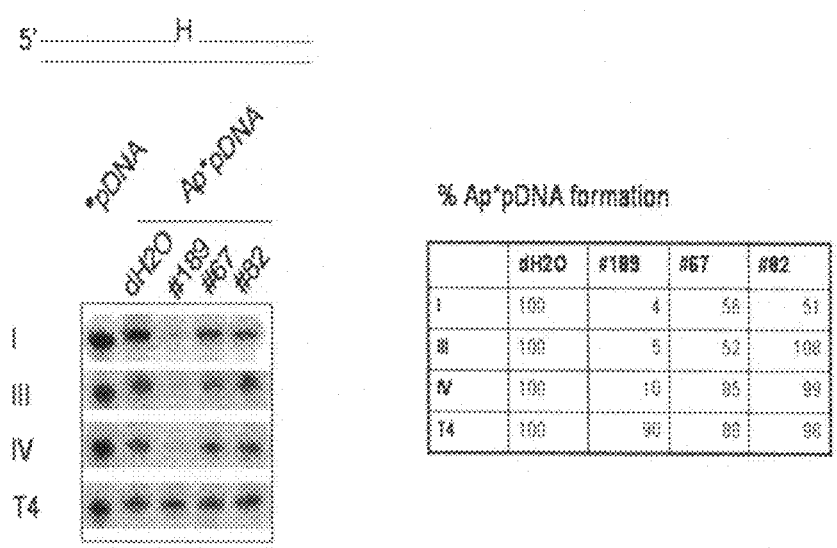
Figure 3C:
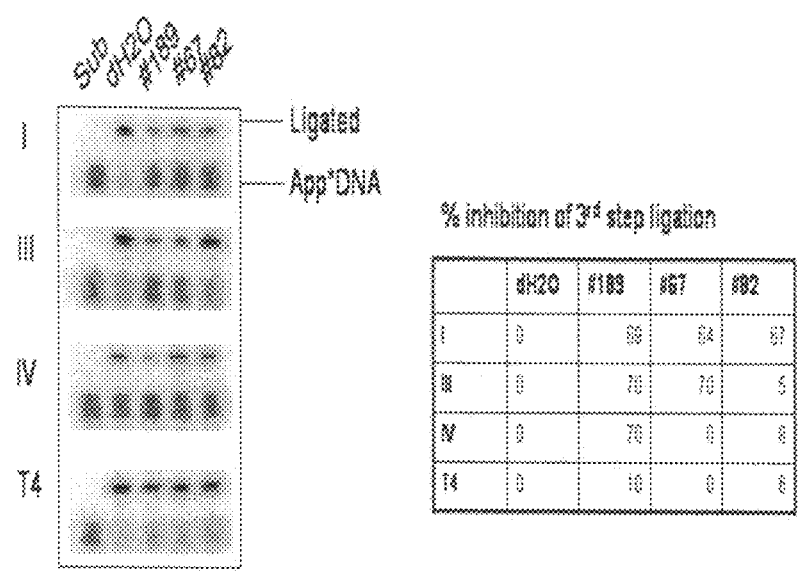

Since the final two steps of the ligation reaction involve interactions with DNA, we examined the effects of the ligase inhibitors on the second (FIG. 3B) (The labeled ligase-adenylate form of human DNA ligases I, III and IV and T4 DNA ligase were incubated with a linear DNA substrate containing a single non-ligatable nick in the absence or presence of compounds 67, 82 and 189 (100 µM). After separation by denaturing gel electrophoresis, the labeled DNA-AMP complex was detected by phosphorimaging (26)) and third steps (FIG. 3C) of the ligation reaction using established assays (25,26) (Non-adenylated human DNA ligases I, III and IV and T4 DNA ligase were incubated with labeled DNA-AMP in the absence or presence of compounds 67, 82 and 189 (100 µM). After separation by denaturing gel electrophoresis, labeled ligated DNA was detected by phosphorimaging (25)).

Based on these assays, we concluded that Compound 189 inhibits step 2 and Compounds 76 and 82 and inhibit step 3.

Next we used published cell extract assays (16,27,28) that measure different DNA replication and repair transactions to confirm the specificity of the DNA ligase inhibitors. FIG. 4A, the flap substrate (0.1 pmol) was incubated with cell extract (20 µg) in the absence (lane 2, Mock) or presence of 100 µmol/L of L189 (lane 3), L67 (lane 4), or L82 (lane 5). hLigI (lane 6, I-dp) and hLigIIIα (lane 7, III-dp) were immunodepleted from the cell extracts prior to incubation with the DNA substrate. Lane 1, DNA substrate alone (Sub). The positions of the DNA substrate (24-mer), cleaved product (18-mer), and fully repaired product (43-mer). The flap substrate shown in FIG. 4A corresponds to an intermediate generated on the lagging strand during DNA replication and in the long patch subpathway of base excision repair. Previously it has been shown that DNA ligase I completes these two DNA transactions after removal of the flap by FEN-1 (16,28). A cell extract from the human cervical cancer cell line HeLa was incubated with the indicated labeled flap substrate that mimics a common intermediate in DNA replication and long patch base excision repair in the absence or presence of Compounds 67, 82, 184 and 189 (25 µM). After separation by denaturing gel electrophoresis, labeled fragments corresponding to the DNA substrate, cleaved product and fully repaired product were detected by phosphorimaging (28). Compounds 67, 82, and 189, all of which inhibit DNA ligase I, inhibited the final ligation step of the repair reaction but had no effect on flap removal by FEN-1.

A natural AP site within a linear DNA molecule (FIG. 4B) is repaired primarily by short patch base excision repair that is completed by DNA ligase III (15). FIG. 4B, the linear DNA substrate with an incised AP site (0.3 pmol) was incubated with a cell extract (20 µg) and [a32P]dTTP in the absence (lane 1, Mock) or presence of 100 µmol/L of L189 (lane 2), L67 (lane 3), or L82 (lane 4). hLigI (lane 5, I-dp) and hLigIIIa (lane 6, III-dp) were immunodepleted from the cell extracts prior to incubation with the DNA substrate. The positions of the single nucleotide insertion reaction intermediate (31-mer, Incorporated) and the ligated product (73-mer, Repaired) are indicated. Thus, a HeLa cell was incubated with labeled dTTP and the indicated linear substrate with an incised AP site that mimics an intermediate in short path base excision repair in the absence or presence of Compounds 67, 82 and 189 (25 µM). Lane 6, DNA ligase I was immunodepleted from the extract prior to the assay. Lane 7, DNA ligase III was immunodepleted from the extract prior to the assay. After separation by denaturing gel electrophoresis, labeled fragments corresponding to a single nucleotide insertion and fully repaired product were detected by phosphorimaging (16). Accordingly, immunodepletion of DNA ligase III but not DNA ligase I inhibited the repair reaction (FIG. 4B). Compounds 67 and 189, each of which inhibits DNA ligase III, reduce repair of the natural AP site whereas Compound 82, which only inhibits DNA ligase I, has no effect (FIG. 4B).

Linear DNA molecules with short complementary single strand overhangs are repaired by non-homologous end joining that is completed by DNA ligase IV (27). A HeLa extract was incubated with a labeled linear cohesive-ended 1 kb fragment with cohesive ends repair in the absence or presence of Compounds 67, 82 and 189 (25 µM)). Lane 7, DNA ligase I was immunodepleted from the extract prior to the assay. Lane 8, DNA ligase III was immunodepleted from the extract prior to the assay. Lane 8, DNA ligase IV was immunodepleted from the extract prior to the assay. After separation by native agarose gel electrophoresis, the linear DNA substrate, re-circularized substrate and dimers trimers etc of the 1 kb substrate were detected by phosphorimaging (27). Accordingly, immunodepletion of DNA ligase IV but not DNA ligase I and III markedly inhibited the repair reaction (FIG. 4C) Compound 189, which inhibits DNA ligase IV, reduced joining of the linear DNA molecules whereas Compounds 67 and 82, which do not inhibit DNA ligase IV, had no effect (FIG. 4C). (Specifically, C, a 1 kb fragment with cohesive ends (0.1 pmol) was incubated with cell extract (20 µg) in the absence (lane 3, Mock) or presence of 100 µmol/L of L189 (lane 4), L67 (lane 5), or L82 (lane 6). hLigI (lane 7, I-dp), hLigIIIa (lane 8, III-dp), and hLigIV (lane 9, IV-dp) were immunodepleted from the cell extracts prior to incubation with the DNA substrate. Lane 1, molecular mass standard (M). Lane 2, DNA substrate alone (Sub). The positions of the DNA substrate and dimmers and multimers of the substrate are indicated.)

To extend the results of the in vivo cell culture screening assay, a subset of compounds were tested in larger cultures. Different concentrations of Compounds 67 and 151 were added to asynchronous subconfluent populations of HCT116 and MCF10A cells. Asynchronous subconfluent populations of HCT116 and MCF10A cells were pre-treated with different concentrations of compound 64 prior to the addition of 3 aminobenzamide (2 mM) MMS (100 µM) or cis-platinum (1 µM). After incubation for 5 days, cell growth was measured by the MTT assay (16).

Figure 5A:
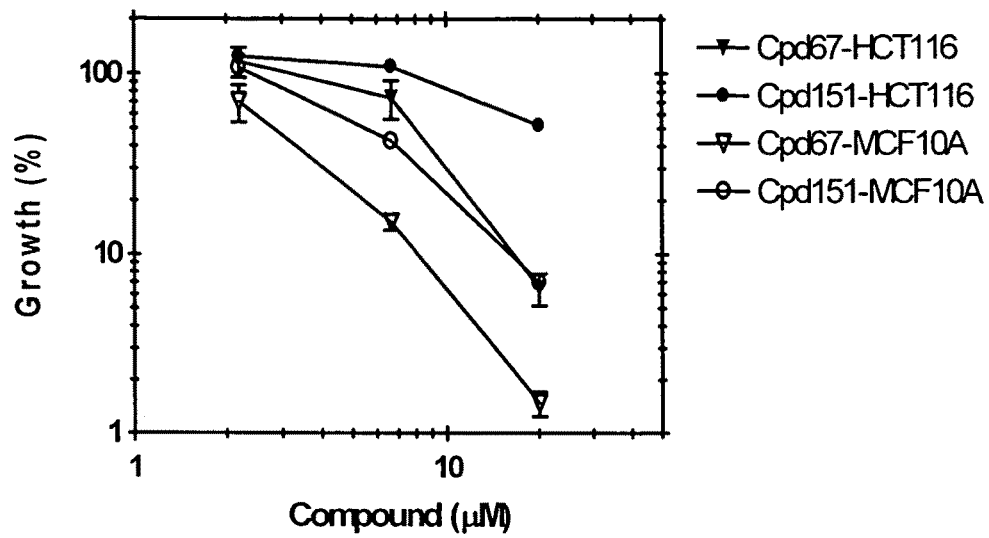
FIGS. 5A and 5B show the effect of DNA ligase inhibitors on cell growth in the absence or presence of DNA damage.
Figure 5B:
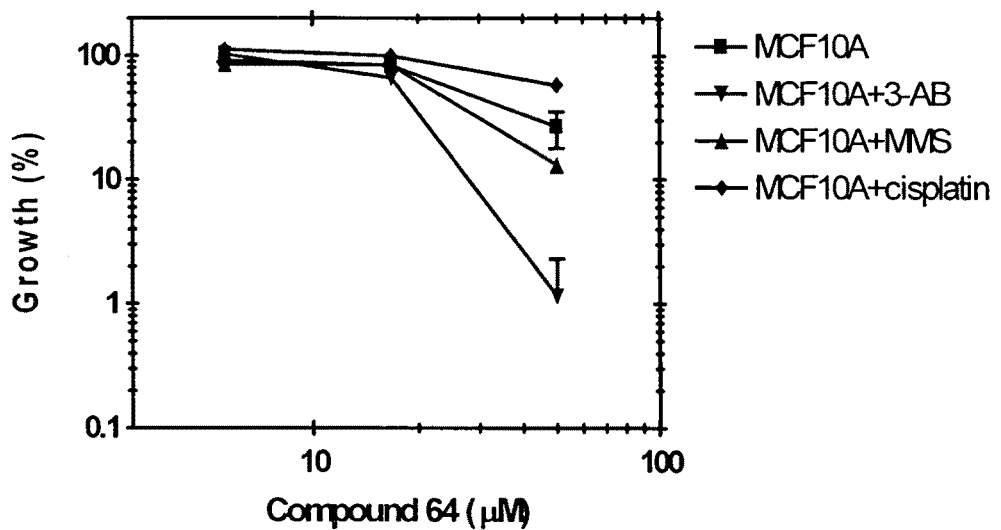

An example of the growth inhibitory effects of Compounds 67 and 151 on the MCF10A and HCT116 cell lines is shown in FIG. 5A. Compound 64 markedly potentiates the growth inhibitory effect of the PARP inhibitor, 3 aminobenzamide on MCF10A cells (FIG. 5B).

To confirm that the DNA ligase inhibitors directly kill cells and potentiate cell killing by DNA damaging agents, we performed colony forming assays.

Figure 6A:
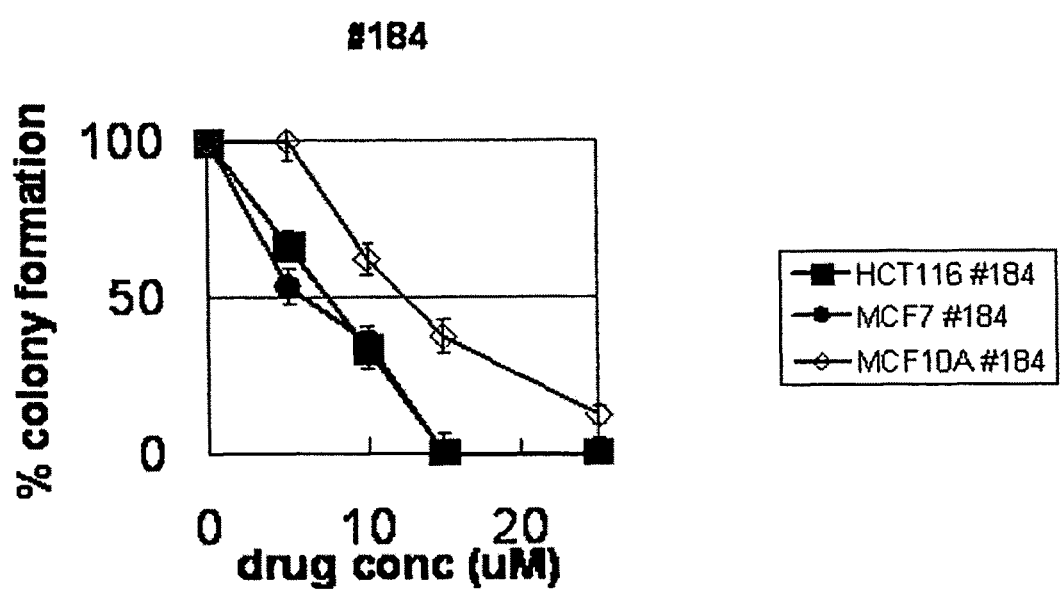
FIGS. 6A, 6B, 6C and 6D show the cytotoxicity of DNA ligase inhibitors in the absence or presence of DNA damage.

Different concentrations of Compound 184 were added to asynchronous subconfluent populations of HCT116, MCF7 and MCF10A cells. Colonies were counted after two weeks. (FIG. 6A).

Figure 6B:
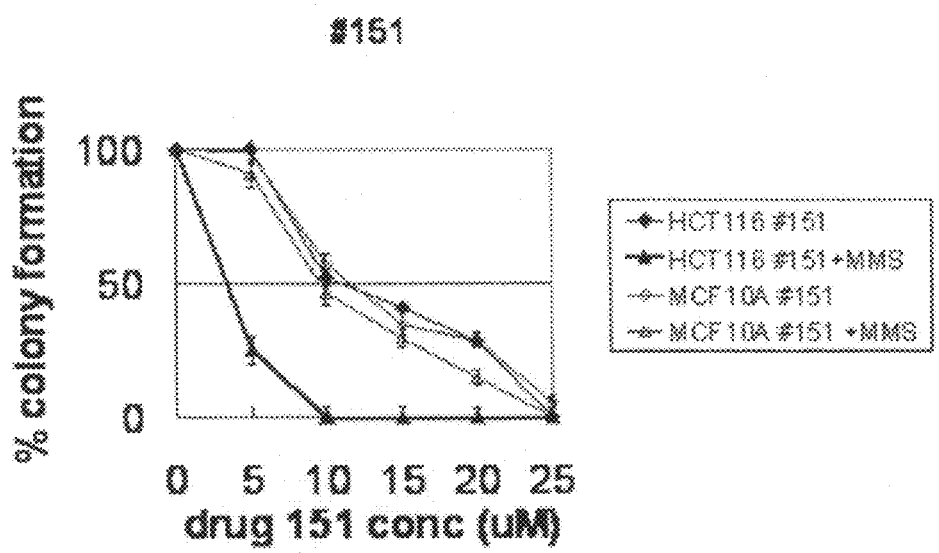

Different concentrations of Compound 151 were added to asynchronous subconfluent populations of HCT116 and MCF10A cells in the absence or presence of MMS (50 µM). Colonies were counted after two weeks. (FIG. 6B).

Figure 6C:
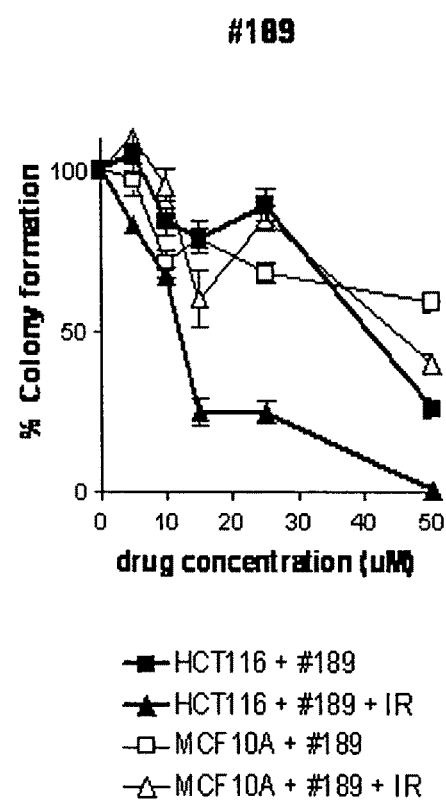

Different concentrations of Compound 189 were added to asynchronous subconfluent populations of HCT116 and MCF10A cells. After 1 hour, cultures were irradiated with 2 gray of ionizing radiation. Colonies were counted after two weeks. (FIG. 6C).

Figure 6D:
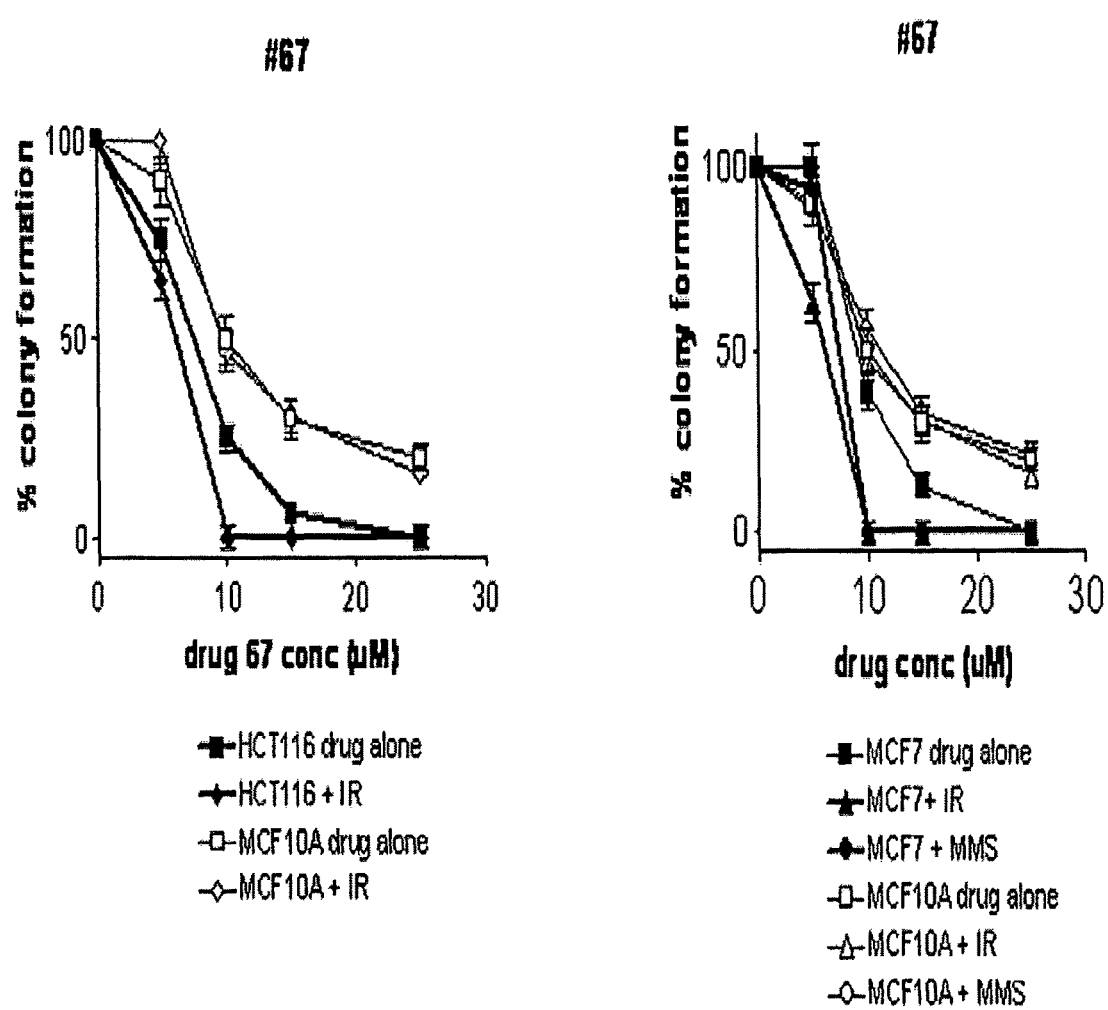

Different concentrations of Compound 67 were added to asynchronous subconfluent populations of HCT116, MCF7 and MCF10A cells. After 1 hour, cultures were irradiated with 2 gray of ionizing radiation. Different concentrations of Compound 67 were added to asynchronous subconfluent populations of HCT116 and MCF10A cells in the absence or presence of MMS (50 µM). Colonies were counted after two weeks. (FIG. 6D).

Compound 184 kills normal breast epithelial cells (MCF10A). It is also more effective at killing colon (HCT116) and breast cancer (MCF7) cell lines (FIG. 6A). Compound 151 markedly potentiates the killing of the colon cancer cell line HCT116 by MMS but has no significant effect on MMS cytotoxicity of the normal breast epithelial cell line MCF10A (FIG. 6B). Compound 189 markedly potentiates the killing of the colon cancer cell line HCT116 by ionizing radiation but has no significant effect on the MMS cytotoxicity of the normal breast epithelial cell line MCF10A (FIG. 6C). Compound 67 also potentiates the killing of the colon cancer cell line HCT116 by ionizing radiation but has no significant effect on the MMS cytotoxicity of the normal breast epithelial cell line MCF10A (FIG. 6D, left panel). Furthermore, Compound 67 potentiates the killing of the breast cancer cell line MCF7 by both MMS and ionizing radiation but has no significant effect on the MMS- and ionizing radiation-induced cytotoxicity the normal breast epithelial cell line MCF10A (FIG. 6D, right panel). Thus, DNA ligase inhibitors are cytotoxic, enhance the cytotoxicity of DNA damaging agents and are more cytotoxic to cancer cells than normal cells.

CADD Analysis of Active Compounds.

Figure 7:
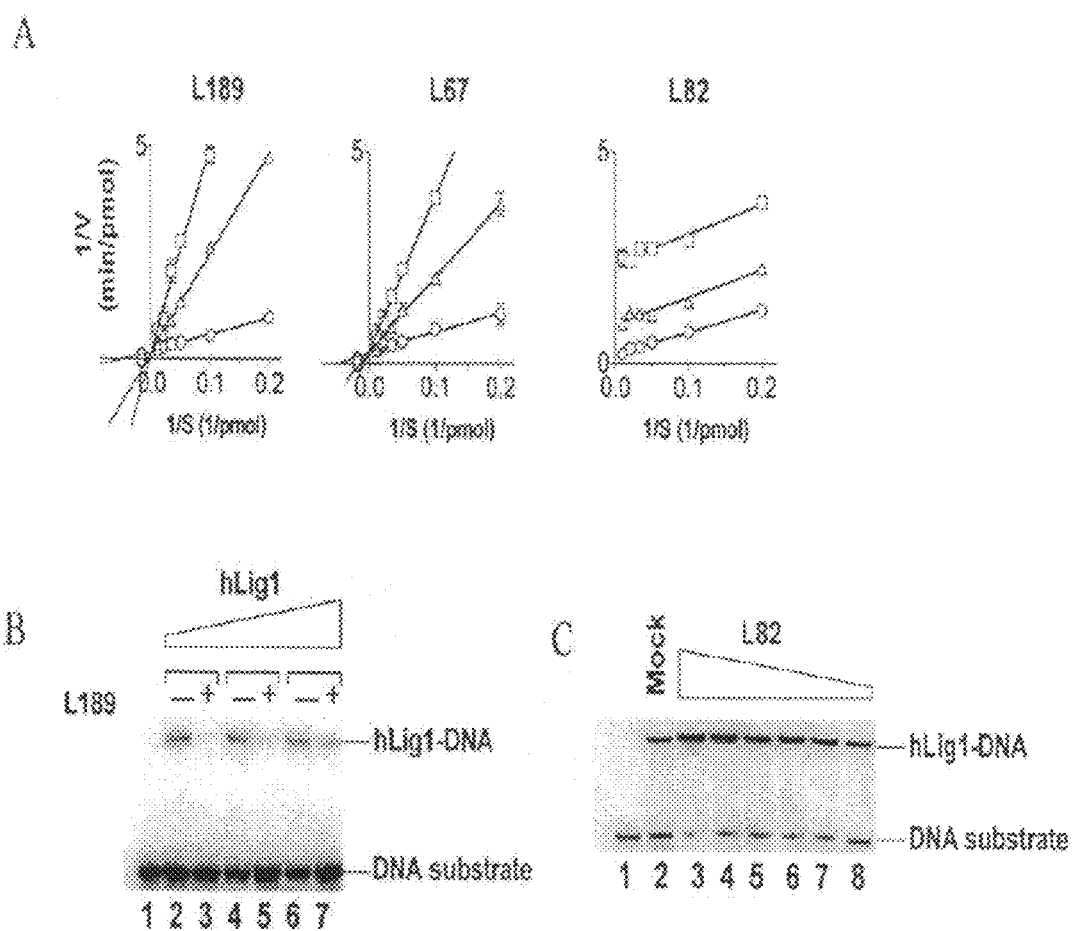
FIG. 7. Michaelis-Menten analysis of ligase inhibitors. Effect of ligase inhibitors on DNA-protein complex formation by hLigI. A, hLig1 (0.05 pmol) was incubated in the absence (o) and presence of L189 (left), L67 (middle), and L82 (right) at 25 μmol/L (open triangle) and 50 μmol/L (open square) with increasing amounts of a linear nicked DNA substrate. Lineweaver-Burk double reciprocal plots of initial reaction velocity (1/V) versus substrate concentration (1/S). B, a labeled linear substrate with a single nonligatable nick (1 pmol) was incubated with no addition (lane 1), 0.25 pmol of hLigI (lanes 2 and 3), 0.5 pmol of hLigI (lanes 4 and 5), and 1 pmol of hLigI (lanes 6 and 7) in the absence (−) or presence (+) of 100 μmol/L of L189. C, a labeled linear substrate with a single nonligatable nick (1 pmol) and hLigI (3 pmol) were incubated with either no addition (lane 2) or 100 pmol/L (lane 3), 60 μmol/L (lane 4), 50 μmol/L (lane 5), 30 μmol/L (lane 6), 20 μmol/L (lane 7), or 10 μmol/L (lane 8) of L82. Lane 1, 1 pmol of DNA substrate alone. The positions of the labeled DNA substrate and DNA-protein complexes are indicated.
Figure 8:
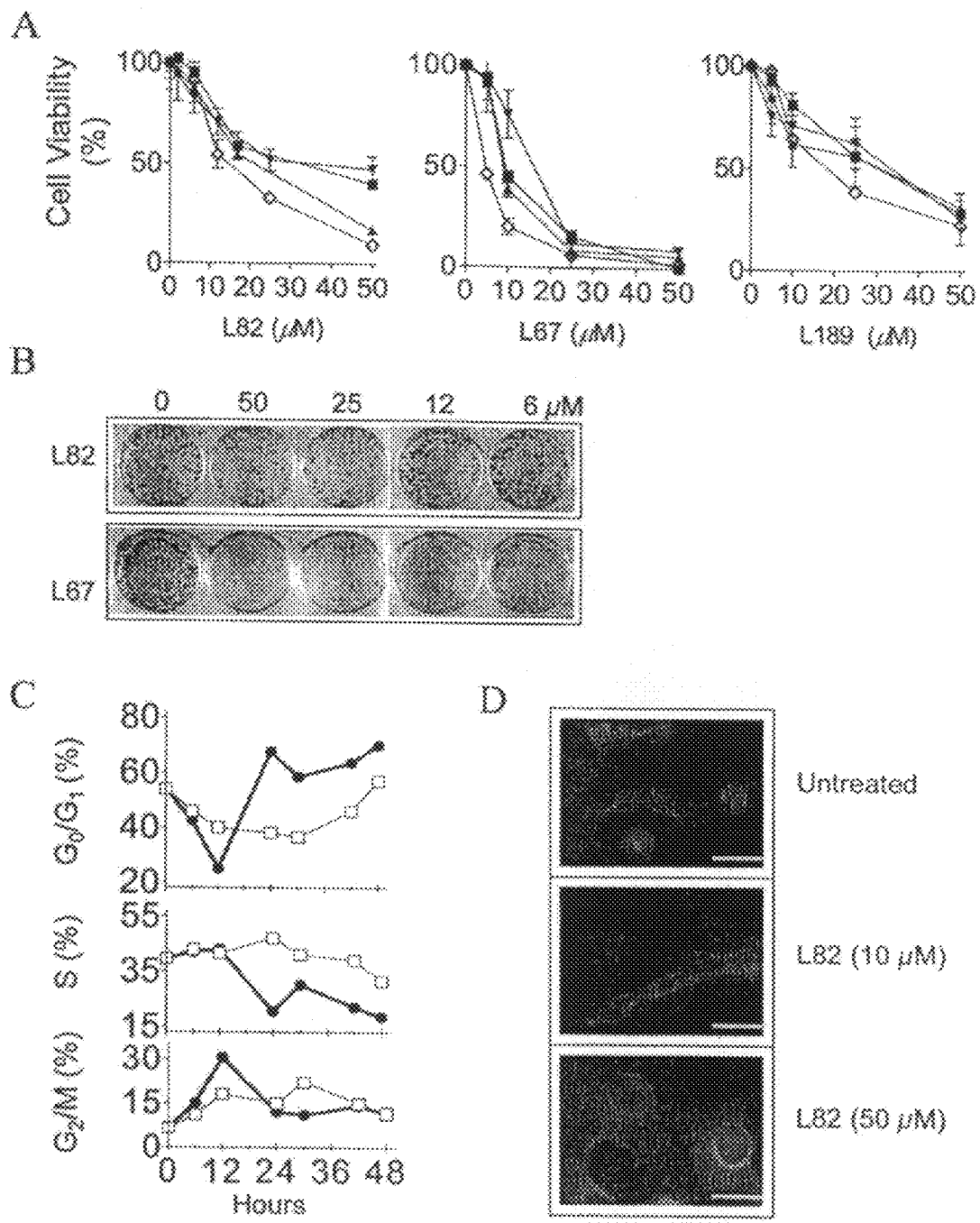
FIG. 8. Characterization of the cytostatic effect of L82. A, MCF 10A (■), MCF7 (◇), HCT116 (▲), and HeLa (upsidedown triangle) cells were plated in the absence or presence of L82 (left), L67 (middle), and L189 (right). After 6 days, cell viability was measured and is expressed as a percentage of the value obtained with untreated cells. B, MCF7 cells were plated out in the absence or presence of L82 (top) and L67 (bottom) at the indicated concentrations. After 2 weeks, colonies were stained with crystal violet. C, after serum starvation for 4 days, MCF 7 cells were returned to serum-containing media either without (■) or with 50 μmol/L of L82 (●). The cell cycle distribution at various time intervals was determined by fluorescence-activated cell sorting. D, asynchronous populations of MCF cells were either untreated (top) or treated with L82 at 10 μmol/L (middle) and 50 μmol/L (bottom). After 3 days, tubulin and DNA were visualized by fluorescence microscopy (bars, 0.5 mm).
Figure 9:
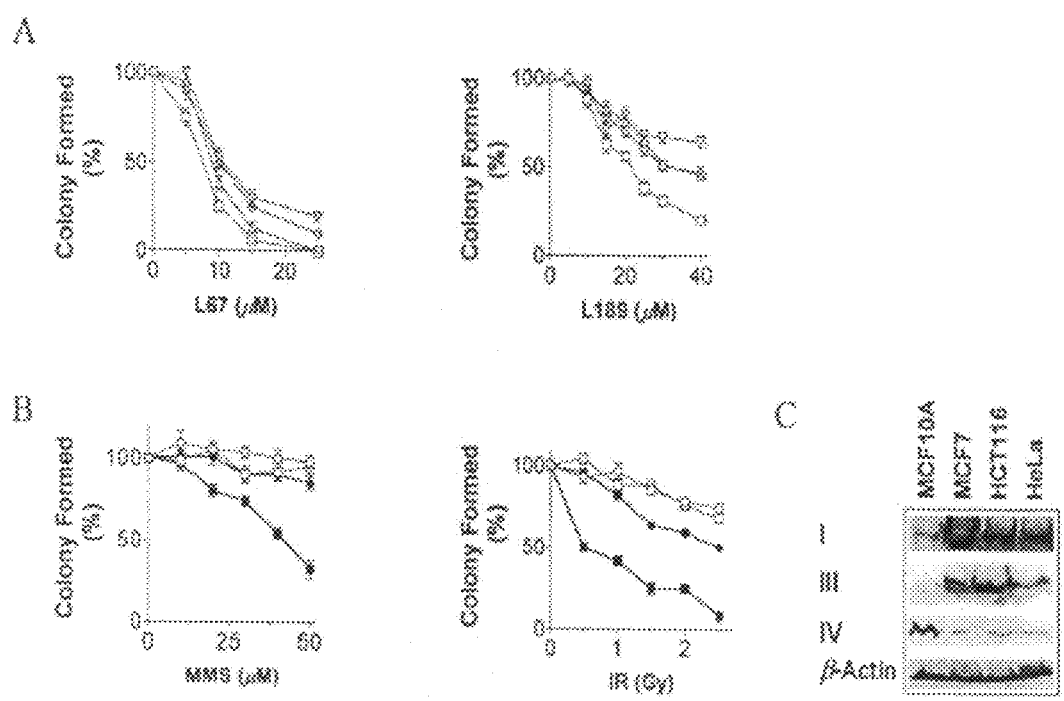
FIG. 9. L67 and L189 are cytotoxic and potentiate the cytotoxic effects of DNA-damaging agents: altered levels of DNA ligase in cancer cells. A, effect of L67 (left) and L189 (right) on the survival of MCF7 (Δ), HCT116 (□), HeLa (◇), and MCF10A (upsidedown triangle) cells. B, normal breast epithelial MCF10A cells (open symbols) and breast cancer MCF7 cells (filled symbols) in the absence (circles)) or presence of 3 μmol/L, of L67 (squares) were exposed to increasing concentrations of MMS (left). Normal breast epithelial MCF10A cells (open symbols) and colon cancer HCT116 cells (filled symbols) in the absence (circles) or presence of 20 μmol/L of L189 (squares) were exposed to increasing doses of ionizing radiation (right). C, hLigI (I), hLigIIIα (III), and hLigIV (IV) were detected in extracts (400 μg) of the indicated cell lines by immunoblotting. To control for extract loading, β-actin was also detected by immunoblotting.
Figure 16:
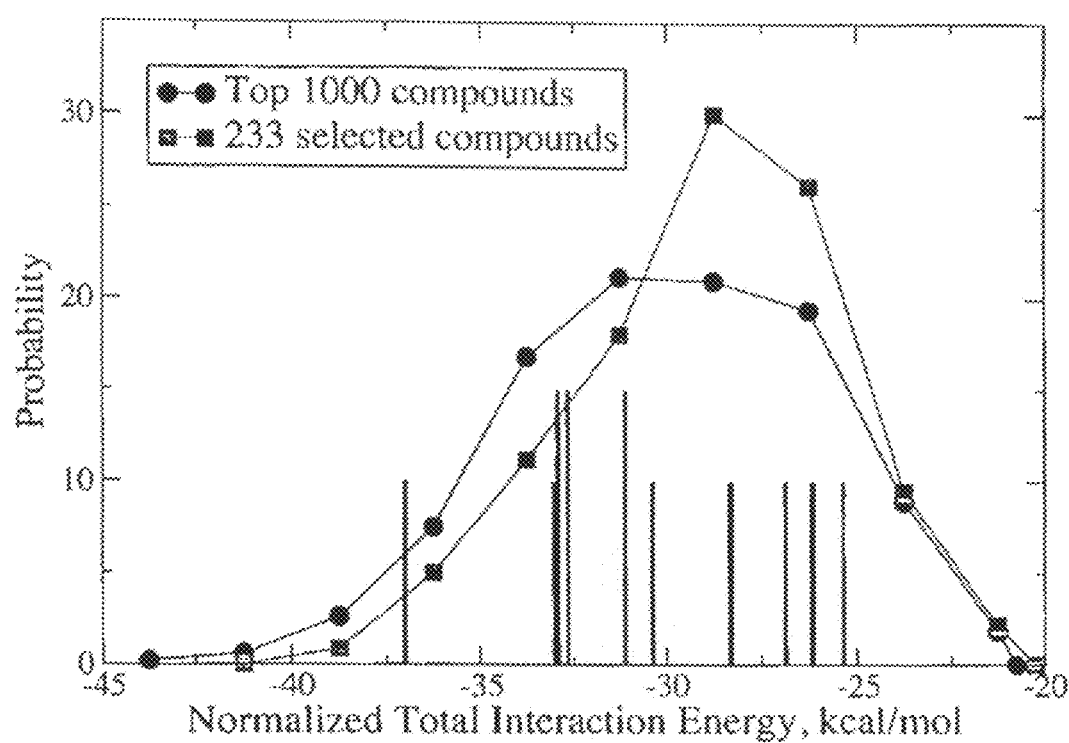
FIG. 16. The distribution of the $N^{2/5}$ normalized total energy scores for the top 1000 compounds (black circles), the selected 233 compounds (red squares) and the 10 compounds that specifically inhibit hLigI activity by >50% (spikes). The scores for the 3 characterized compounds are shown as longer spikes; the wider spikes are associated with two compounds having similar scores.

Structures of the 10 hLigI specific inhibitors are shown in FIG. 7. As may be seen, the structures are chemical diverse, as verified by the calculation of pairwise Tanimoto similarity indices between a number of active compounds (Table 7). The largest Tc value between two compounds is 69% and the majority of the values are less than 50%, indicating a low degree of similarity between compounds. Previous studies have indicated that a value of 85% or more is associated with compounds that will have similar biological activities (72). The inclusion of chemical diversity in compound selection has the desirable effect of identify structurally dissimilar compounds for drug optimization, thereby increasing the probability of identifying active compounds. This may be seen by analyzing the energy scores of the selected compounds. Presented in FIG. 16 are the distributions of the normalized total energy scores for the 1000 compounds from the secondary screen, for the 233 compounds selected from the top 1000 based on diversity and physical properties and of 9 active compounds (FIG. 1). Consideration of diversity and physical properties led to the selection of more compounds with less favorable interaction energies. Notably, many of the active compounds would not have been selected if the top 233 scoring compounds were selected based on interaction energies and so would not have been identified.

The importance of the inclusion of multiple conformations of the putative binding site from the MD simulation in the in silico screen may be determined by simply identifying the conformation from which 10 active compounds were selected. Of the 9 hLigI specific inhibitors, one (67) was based on the crystal conformation, none were based on MD conformation C2 (time point 2.015 ns of the simulation), two (82, 113) were based on MD conformation C3 (time point 2.335 ns of the simulation), three (25, 190, 197) were based on MD conformation C4 (time point 2.950 ns of the simulation) and three (64, 189, 200) on conformation C5 (time point 3.795 ns of the simulation). Thus, the inclusion of multiple conformations is leading to the identification of additional active compounds, emphasizing the utility of this component of the screening procedure.

The protein conformation is that from the crystallographic study with the orientation of the compounds extracted from the individual conformations following alignment of the protein conformations as shown in FIG. 12A. All the inhibitors occupy the targeted site, consistent with the docking methodology. However, they do sample different regions of the binding site. Such difference may contribute to differential selectivities of activity of the inhibitors for different ligases.

Three of the active compounds, 67, 82, and 189 have been subjected to more extensive biological characterization (73). Although all three compounds are predicted to bind in the putative binding site, they do exhibit some level of variability in the binding orientations. Interestingly, while all three compounds inhibit hLigI but not T4 DNA ligase (Table 4), their activity versus the other human DNA ligases differs significantly. While 82 inhibits only hLigI, 67 inhibits both hLigI and hLigIII and 189 inhibits all three human DNA ligases. Presumably, differences in the specificities of the inhibitors for the three human DNA ligases reflect a combination of differences in the binding modes of the structurally diverse inhibitors and differences in the molecular architecture of the targeted DNA binding pocket between the three human DNA ligases. Importantly, inhibitors with defined specificities for the different human DNA ligases will be invaluable reagents for elucidating the physiological roles of human DNA ligases.

Consistent with the inclusion of physical properties in the selection process, all the hLigI specific inhibitors fall into the drug-like range according to Lipinski's rule of five (Table 4) (71), while still spanning a range of physical properties.

From the in silico database Applicants have identified compounds of General Formulae I-XVI as also being DNA ligase inhibitor candidates.

General Formulae I and II are illustrative of compounds related to Compound 64. Compounds related to Compound 64 are shown in Table 8.

General Formulae IIA and IIIA are illustrative of compounds related to Compound 67. Compounds related to Compound 67 are shown in Table 9.

General Formulae III is illustrative of compounds related to Compound 78. Compounds related to Compound 78 are shown in Table 10.

General Formulae IV and V are illustrative of compounds related to Compound 113. Compounds related to Compound 113 are shown in Table 11.

General Formulae IX and X are illustrative of compounds related to Compound 151. Compounds related to Compound 151 are shown in Table 12.

General Formulae XI and XII are illustrative of compounds related to Compound 180. Compounds related to Compound 180 are shown in Table 13.

General Formulae XIII and XIV are illustrative of compounds related to Compound 189. Compounds related to Compound 189 are shown in Table 14.

General Formulae XV and XVI are illustrative of compounds related to Compound 197. Compounds related to Compound 197 are shown in Table 15.

(I)

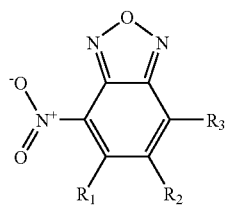

where $R_2$ is hydrogen,
$R_3$ is hydrogen, halogen, Cl,

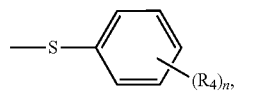

(where $R_4$ is halogen or Cl and $n$ is 0-5), or

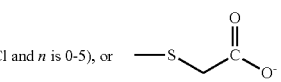

$R_1$ is

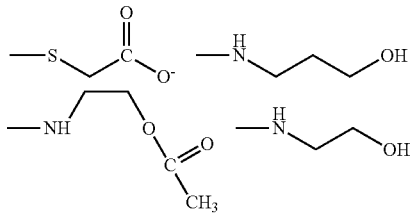

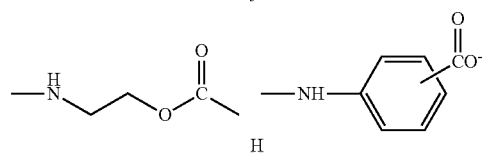

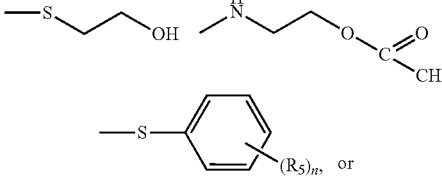

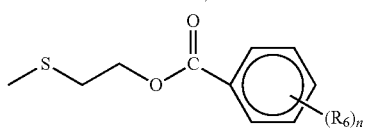

(where $R_5$ is halogen or F and $n$ is 0-5)

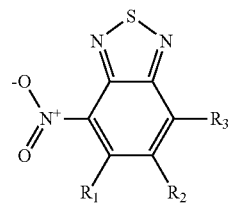

(where $R_6$ is halogen or F and $n$ is 0-5)

(II)

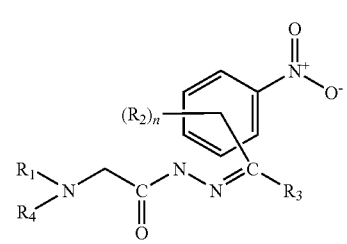

where $R_1$, $R_2$ and $R_3$ are the same as in formula (I)

(IIA)

$R_2$ are each the same or different and are selected from —OH, alkoxy, halogen, —CH$_3$, —OCH$_3$Cl, Br and F or two $R_2$s form a fused ring and n=0-3, preferably 0-2

$R_3$=H, alkyl, or —CH$_3$ $R_4$=H, alkyl, methyl or ethyl; or one of $R_3$ and one of $R_2$ form a fused ring

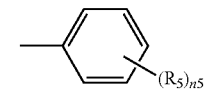

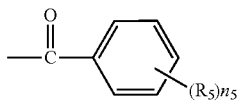

(where $R_5$ is halogen, alkyl, Br, Cl, or -CH$_3$ and $n_5$ is 0-5)

(where $R_5$ and is halogen, alkyl, Br, Cl, or -CH$_3$ and $n_5$ is 0-5)

or $R_1$ and $R_4$ form a fused ring.

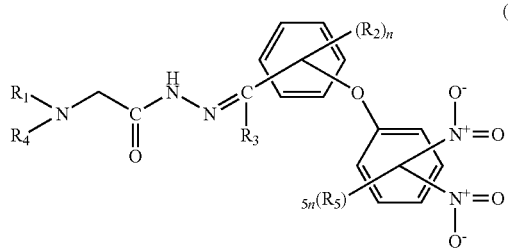
(IIIA)

Where $R_1$, $R_2$, $R_3$, $R_4$, and n are the same or in general formula (IIA)

$R_5$ and $n_5$ are same as $R_2$ and n in general formula (IIA).

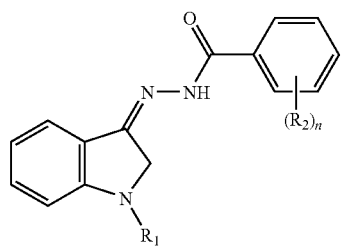
(III)

where $R_{10}$ is alkyl, alkylene, alkoxy, ethyl, methyl, alkyl substituted with aryl,

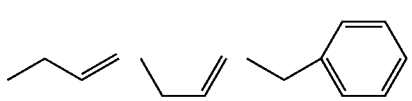

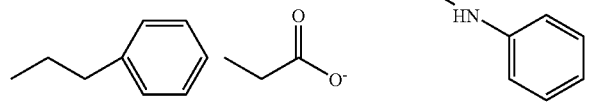

-continued

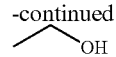

$R_2$ is O$^-$, halogen, alkyl, alkoxy, BR, Cl, —O—CH$_3$, —NH$_2$, —CH$_3$, and when n is greater than 2, two $R_2$s may form a fused ring, n is 1-5.

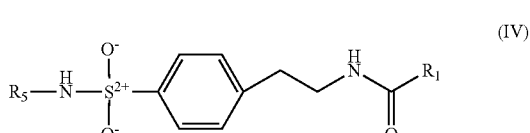
(IV)

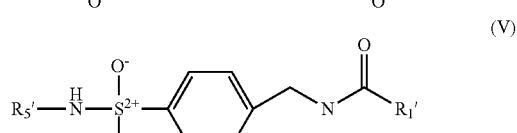
(V)

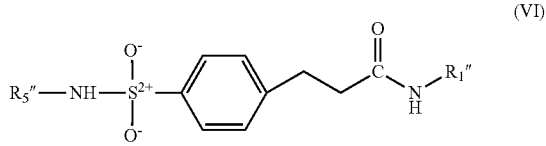
(VI)

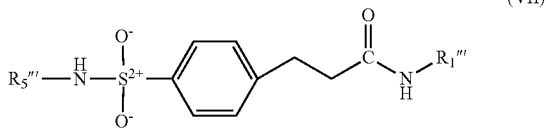
(VII)

wherein $R_5$, $R_{5'}$, $R_{5''}$ and $R_{5'''}$ are selected from H, aryl, and alkyl; and preferably H wherein $R_1$, $R_{1'}$, $R_{1''}$ and $R_{1'''}$ are selected from

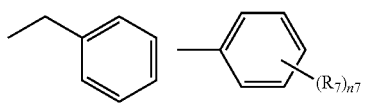

where each $R_7$ is independently selected from halogen, Cl, Br, F, alkyl, —CH$_3$, and $n_7$ is 0-5

where $R_8$ and $n_8$ are the sane as $R_7$ and $n_7$,

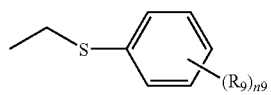

where $R_9$ and $n_9$ are the same as $R_7$ and $n_7$, alkyl 1-cycloalkyl,

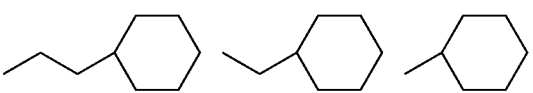

-continued

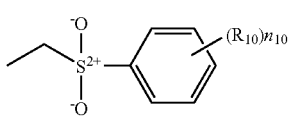

where R₁₀ and n₁₀ the same as R₇ and n₇, (VIII)

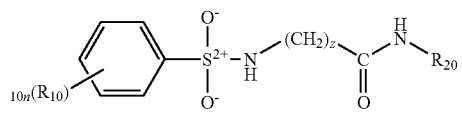

where z is 1, 2, 4 or 5,

R₁₀ is selected from halogen, Br and Cl,

R₂₀ is selected from alkylene, cycloalkyl, alkyl-aryl,

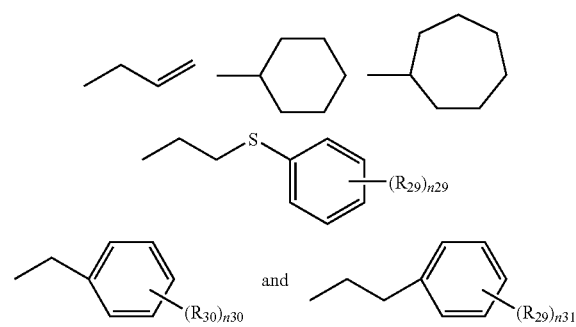

where R₂₉, R₃₀ and R₃₁ are selected from halogen, Cl, I, alkyl n₂₉, n₃₀ and n₃₁ are 0-5; preferably 0 or 1 n₁₀ is 0-5; preferably 0 or 1.

(IX)

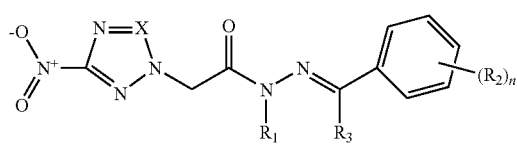

wherein

R₂ is selected from —OH, O—,

alkoxy, halogen, Cl, and —O—CH₃, n is 0-5, preferably 1 or 2,

R₃ is selected from H, alkyl, and —CH₃,

R₁ is selected from H, alkyl, and CH₃, and

X is selected from N and CH.

(X)

wherein

R₂ is selected from —OH, O—,

alkoxy, halogen, Cl, and —O—CH₃,

X₁ is selected from N and CR₃,

X₂ is selected from N and CR₄, wherein R₃ and R₄ are independently selected from H and

and at least one of X₁ or X₂ is

(XI)

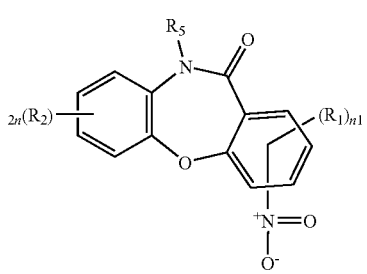

R₅ is selected from H, alkyl, methyl, halogen and Cl,

R₁ is selected from aryloxy, alkoxy,

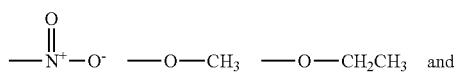

-continued

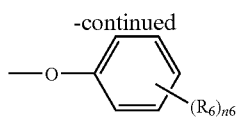

where $R_6$ is selected from alkyl, —$CH_3$, H, alkoxy, —$OCH_2$—$CH_3$, halogen, Cl, Br

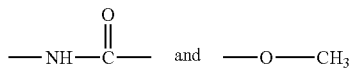

$n_6$ is 0-6;
$n_1$ is 0-3
$R_2$ is selected from H, alkyl, halogen, methyl, and Cl, and $n_2$ is 0 to 5.

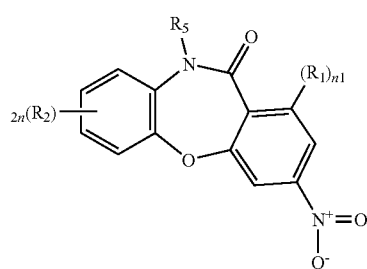

where $R_1$, $R_2$ and $n_2$ are same as defined in Formula (XI).

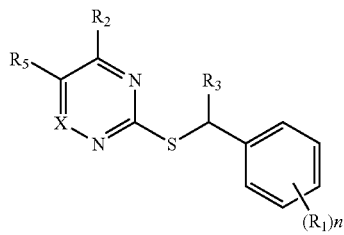

$R_1$ is selected from H, alkyl, methyl, —C≡N, halogen and Cl, or when n is greater than 2 two $R_1$s may form a fused ring n is 0-5,
$R_3$ is selected from H, alkyl and methyl,
$R_2$ is selected from —OH and —$NH_2$,
X is selected from N and $CR_4$, where $R_4$ is selected from —OH, N and H,
$R_5$ is selected from H, —OH, $NH_2$ and S

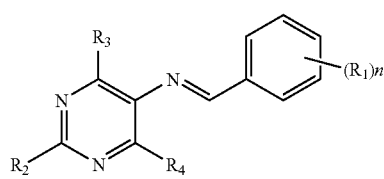

$R_1$ is selected from H, alkyl, methyl, —C≡N, halogen and Cl, or when n is greater than 2 two $R_1$s may form a fused ring n is 0-5,
$R_2$, $R_3$ and $R_4$ are independently selected from —O and —N.

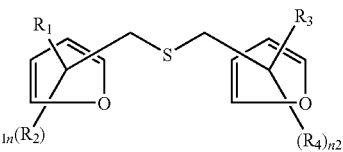

$R_1$ and $R_2$ are independently selected from

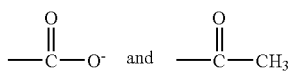

$R_2$ and $R_4$ are independently selected from alkyl, akyl, methyl and benzyl
$n_1$ and $n_2$ are independently selected from 0, 1, 2.

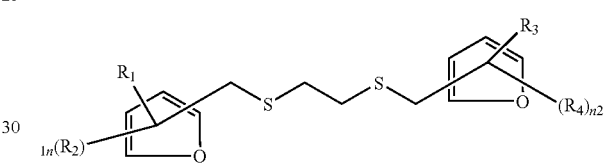

$R_1$ and $R_2$ are independently selected from

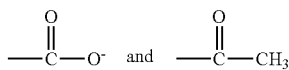

$R_2$ and $R_4$ are independently selected from alkyl, akyl, methyl and benzyl
$n_1$ and $n_2$ are independently selected from 0, 1, 2.

The DNA ligase inhibitors of the present invention may also be used as research tools in addition to therapeutics. As research tools, the DNA ligase inhibitors may be used to identify the DNA ligase involved in different DNA transactions either in cell culture and/or in cell extract based assays. Including the use of DNA ligase inhibitors to provide novel insights into the reaction mechanisms of human DNA ligases; the use of DNA ligase inhibitors in cell extract assays to identify the human DNA ligase involved in DNA repair pathways; and the use of DNA ligase inhibitors in cell culture assays to identify the human DNA ligase involved in different DNA repair pathways in vivo. For example, delineating DNA ligases participating and determining which of multiple pathways are being used.

The DNA ligase inhibitors of the present invention may be used to facilitate in vitro and in vivo studies delineating the cellular functions of these enzymes.

Most DNA damaging agents introduce more than one type of DNA lesion. In addition, a specific DNA lesion may be removed by more than one DNA repair pathway. Since the DNA ligase inhibitors of the present invention inhibit DNA repair pathways, the use of the inhibitors in a combination of extract and cell culture assays may be used to delineate the DNA repair pathways involved in the repair of DNA lesions introduced by a DNA damaging agent and the DNA repair pathways involved in the repair of a specific DNA lesion.

The DNA ligase inhibitors of the present invention may be used as research tools to promote the understanding of genome stability and DNA repair, such as Lagging strand DNA replication; Telomere replication; Rescue of stalled replication forks; Damage response signaling cascade; DSB repair; BER; poly-dependent long patch; PCNA-dependent long patch; Short patch; and NER: DNA double strand break repair by homology-dependent pathways and by the major and alternative non-homologous end-joining pathways.

The DNA ligase inhibitors of the present invention may also be used in drug development for clinical cancer treatment, such as anti-cell proliferation and Radio-sensitizers.

As used herein, "treat" means alter, apply, effect, improve, care for or deal with medically or surgically, ameliorate, cure, stop and/or prevent an undesired biological (pathogenic) process. The skilled artisan is aware that a treatment may or may not cure.

As used herein, the effective amount or "therapeutically effective amounts" of the compound of the present invention to be used are those amounts effective to produce beneficial results in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

A therapeutically effective amount of a compound of the present invention as a treatment varies depending upon the host treated and the particular mode of administration. The term "body weight" is applicable when an animal is being treated. When isolated cells are being treated, "body weight" as used herein means "total cell body weight". The term "total body weight" may be used to apply to both isolated cell and animal treatment. Those of skill in the art will recognize the utility of a variety of dosage range.

TABLE 2

| | ligase_1x9n_docking_233_compounds | COMP_NAME | IDNUMBER | stru | MolW | logP |
|---|---|---|---|---|---|---|
| 1 | | chembridge000828 | 5103856 | 2335 | 174 | 1.92 |
| 2 | | chembridge0004647 | 5133963 | 2335 | 238 | 0.724 |
| 3 | | chembridge004783 | 5135431 | 1x9n | 226 | −0.672 |
| 4 | | chembridge005314 | 5140822 | 1x9n | 198 | 0.552 |
| 5 | | chembridge009555 | 5185417 | 2335 | 281 | 2.54 |

TABLE 2-continued

| ligase_1x9n_docking_233_compounds | COMP_NAME | IDNUMBER | stru | MolW | logP |
|---|---|---|---|---|---|
| 6 | chembridge0119938 | 6635973 | 1x9n | 337 | 1.05 |
| 7 | chembridge0132951 | 5540113 | 2950 | 295 | 4.32 |
| 8 | chembridge0136123 | 5649818 | 2950 | 316 | −1.87 |
| 9 | chembridge0137192 | 5679271 | 2950 | 326 | 0.653 |
| 10 | chembridge0144275 | 5807168 | 1x9n | 322 | 2.65 |
| 11 | chembridge014881 | 5226945 | 2950 | 381 | 4.06 |
| 12 | chembridge015172 | 5227796 | 2950 | 232 | 1.72 |

TABLE 2-continued

| ligase_1x9n_docking_233_compounds | COMP_NAME | IDNUMBER | stru | MolW | logP |
|---|---|---|---|---|---|
| 13 | chembridge0171207 | 6102396 | 2335 | 433 | 2.3 |
| 14 | chembridge0171753 | 6106327 | 2950 | 235 | 0.925 |
| 15 | chembridge017857 | 5241412 | 1x9n | 377 | 1.54 |
| 16 | chembridge017892 | 5241504 | 2335 | 300 | 2.36 |
| 17 | chembridge0183353 | 6203744 | 2950 | 218 | 0.384 |

TABLE 2-continued

| ligase_1x9n_docking_233_compounds | COMP_NAME | IDNUMBER | stru | MolW | logP |
|---|---|---|---|---|---|
| 18 | chembridge0192792 | 6364469 | 2950 | 270 | 2.85 |
| 19 | chembridge0222418 | 6629596 | 2335 | 275 | −0.025 |
| 20 | chembridge0250465 | 5925673 | 2950 | 230 | 0.83 |
| 21 | chembridge0253645 | 6297813 | 2950 | 210 | −0.982 |
| 22 | chembridge0257297 | 6550468 | 2950 | 294 | 3.43 |
| 23 | chembridge0266747 | 6841883 | 2335 | 301 | 0.704 |

TABLE 2-continued

| ligase_1x9n_docking_233_compounds | COMP_NAME | IDNUMBER | stru | MolW | logP |
|---|---|---|---|---|---|
| 24 | chembridge0295137 | 7173063 | 1x9n | 356 | 1.02 |
| 25 | chembridge029819 | 5317419 | 2950 | 191 | 0.119 |
| 26 | chembridge0307818 | 7296187 | 2950 | 271 | 1.29 |
| 27 | chembridge0343539 | 7650920 | 2335 | 308 | 1.64 |
| 28 | chembridge0347904 | 7676009 | 1x9n | 344 | 2.26 |
| 29 | chembridge0352654 | 7699479 | 2335 | 383 | 4.76 |

TABLE 2-continued

| ligase_1x9n_docking_233_compounds | COMP_NAME | IDNUMBER | stru | MolW | logP |
|---|---|---|---|---|---|
| 30 | chembridge0355774 | 7724431 | 2950 | 318 | 1.63 |
| 31 | chembridge036048 | 5355751 | 2335 | 293 | 0.343 |
| 32 | chembridge0365296 | 7777402 | 2335 | 386 | 1.98 |
| 33 | chembridge0374491 | 7812749 | 2950 | 237 | 3.38 |
| 34 | chembridge0374541 | 7813065 | 2335 | 303 | 1.57 |
| 35 | chembridge0377382 | 7830700 | 2950 | 233 | 2.01 |

TABLE 2-continued
| ligase_1x9n_docking_233_compounds | | COMP_NAME | IDNUMBER | stru | MolW | logP |
|---|---|---|---|---|---|---|
| 36 | 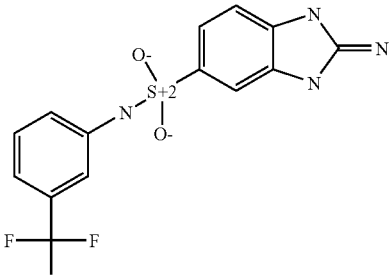 | chembridge0378150 | 7836125 | 2950 | 357 | 2.28 |
| 37 | 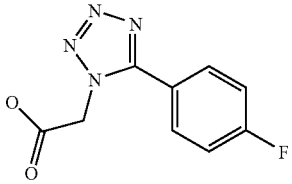 [SMILES: O=C(O)Cn1nnnc1-c1ccc(F)cc1] | chembridge0382972 | 7863038 | 2335 | 222 | 0.311 |
| 38 | 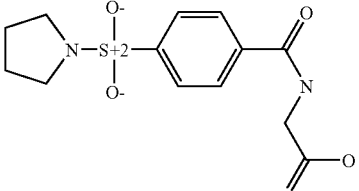 | chembridge0387746 | 7902307 | 2335 | 312 | −0.012 |
| 39 | 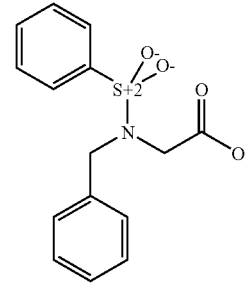 | chembridge063174 | 5608638 | 2950 | 305 | 1.95 |
| 40 | 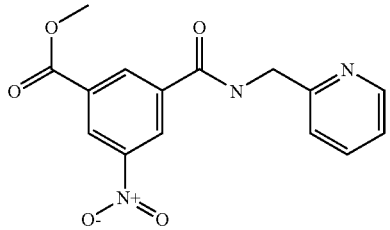 [SMILES: COC(=O)c1cc(C(=O)NCc2ccccn2)cc([N+](=O)[O-])c1] | chembridge080590 | 5742694 | 2335 | 315 | 1.71 |
| 41 | 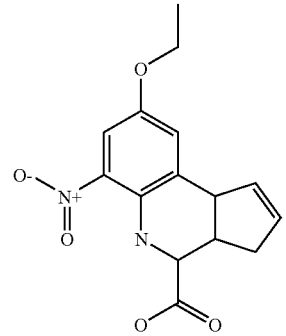 [SMILES: CCOc1cc2c(c([N+](=O)[O-])c1)NC(C(=O)O)C1CC=CC21] | chembridge085143 | 5790780 | 2335 | 304 | 1.91 |

TABLE 2-continued

| | ligase_1x9n_docking_233_compounds | COMP_NAME | IDNUMBER | stru | MolW | logP |
|---|---|---|---|---|---|---|
| 42 | | chembridge091964 | 5869880 | 2335 | 301 | 2.79 |
| 43 | | chembridge099119 | 6051018 | 1x9n | 335 | 4.36 |
| 44 | | chembridge102405 | 5356872 | 2950 | 312 | 1.5 |
| 45 | | chembridge103842 | 5154723 | 2335 | 329 | 3 |
| 46 | | chembridge104229 | 5210894 | 2335 | 339 | 1.61 |
| 47 | | chemdiv015291 | 3448-0483 | 2335 | 276 | 2.97 |

TABLE 2-continued
| ligase_1x9n_docking_233_compounds | | COMP_NAME | IDNUMBER | stru | MolW | logP |
|---|---|---|---|---|---|---|
| 48 | 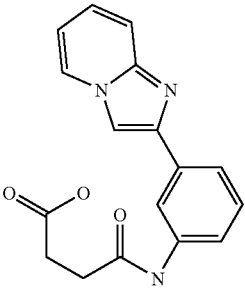 [SMILES: O=C(O)CCC(=O)Nc1cccc(-c2cn3ccccc3n2)c1] | chemdiv016239 | 3464-8119 | 2335 | 309 | 1.56 |
| 49 | 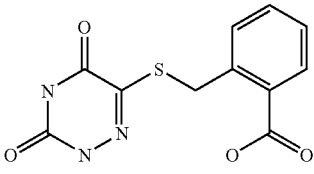 [SMILES: O=C(O)c1ccccc1CSc1n[nH]c(=O)[nH]c1=O] | chemdiv018608 | 2279-5355 | 2950 | 279 | 1.5 |
| 50 | 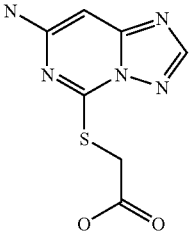 [SMILES: Nc1cc2ncnn2c(SCC(=O)O)n1] | chemdiv0202765 | 000A-0636 | 2335 | 225 | −0.669 |
| 51 | 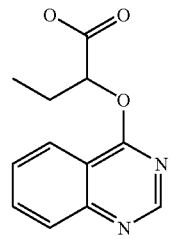 [SMILES: CCC(Oc1ncnc2ccccc12)C(=O)O] | chemdiv0223644 | 4300-0817 | 2335 | 231 | 1.6 |
| 52 | 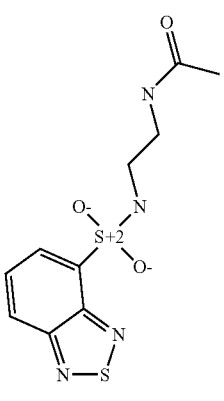 | chemdiv0254427 | K831-0255 | 2950 | 300 | 0.535 |
| 53 | 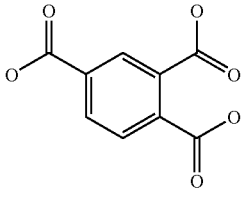 [SMILES: O=C(O)c1ccc(C(=O)O)c(C(=O)O)c1] | chemdiv0260892 | 0054-0264 | 2950 | 210 | 0.972 |

TABLE 2-continued

| ligase_1x9n_docking_233_compounds | COMP_NAME | IDNUMBER | stru | MolW | logP |
|---|---|---|---|---|---|
| 54 | chemdiv0262519 | 1725-0122 | 2335 | 129 | −0.903 |
| 55 | chemdiv0281075 | 4055-0046 | 2335 | 205 | −0.375 |
| 56 | chemdiv0283584 | 4114-0028 | 2950 | 305 | 2.15 |
| 57 | chemdiv0283734 | 4130-0051 | 2335 | 260 | 0.684 |
| 58 | chemdiv0297199 | 4596-0306 | 1x9n | 175 | 0.682 |
| 59 | chemdiv0297579 | 4676-0062 | 2950 | 252 | 2.22 |
| 60 | chemdiv0310162 | 8011-6595 | 2950 | 204 | 0.399 |
| 61 | chemdiv0311450 | 8012-0236 | 2335 | 340 | 3.58 |

TABLE 2-continued

| ligase_1x9n_docking_233_compounds | COMP_NAME | IDNUMBER | stru | MolW | logP |
| --- | --- | --- | --- | --- | --- |
| 62 | chemdiv0329374 | K831-0247 | 2950 | 287 | 0.226 |
| 63 | chemdiv0330961 | K906-0447 | 2950 | 369 | 1.03 |
| 64 | chemdiv0333435 | R052-1644 | 2950 | 290 | 2.03 |
| 65 | chemdiv071566 | 0814-0180 | 2950 | 321 | 3.1 |
| 66 | chemdiv093992 | 1535-0002 | 2335 | 224 | 0.103 |
| 67 | chemdiv102812 | 1761-0019 | 1x9n | 486 | 4.79 |

TABLE 2-continued

| | ligase_1x9n_docking_233_compounds | COMP_NAME | IDNUMBER | stru | MolW | logP |
|---|---|---|---|---|---|---|
| 68 | | chemdiv103836 | 1761-1961 | 1x9n | 370 | 0.978 |
| 69 | | chemdiv117392 | 2093-0008 | 2950 | 193 | 0.834 |
| 70 | | chemdiv137918 | 2595-1130 | 2335 | 219 | 0.647 |
| 71 | | chemdiv172782 | 8007-0302 | 2950 | 320 | 0.727 |
| 72 | | chemdiv189691 | 8010-4604 | 2335 | 356 | 4.22 |
| 73 | | chemdiv195033 | K061-1138 | 2950 | 220 | 0.575 |

TABLE 2-continued

| | ligase_1x9n_docking_233_compounds | COMP_NAME | IDNUMBER | stru | MolW | logP |
|---|---|---|---|---|---|---|
| 74 | | chemdiv201905 | K781-0461 | 2335 | 259 | 1.7 |
| 75 | | chemdiv202632 | R095-0016 | 2950 | 306 | 3.66 |
| 76 | | chemdiv4000099 | 000A-0435 | 2950 | 205 | 0.146 |
| 77 | | chemdiv4000752 | 0519-0362 | 2950 | 331 | 0.823 |
| 78 | | chemdiv4003854 | 2672-0239 | 2335 | 321 | 2.85 |
| 79 | | chemdiv4003904 | 2684-1487 | 2950 | 309 | 1.16 |

TABLE 2-continued

| | ligase_1x9n_docking_233_compounds | COMP_NAME | IDNUMBER | stru | MolW | logP |
|---|---|---|---|---|---|---|
| 80 | | chemdiv4004117 | 2764-0217 | 2950 | 259 | 0.825 |
| 81 | | chemdiv4006822 | 3350-0006 | 2950 | 266 | 1.75 |
| 82 | | chemdiv4014181 | 4300-0746 | 2335 | 310 | 4.72 |
| 83 | | chemdiv4016932 | 4469-0504 | 2950 | 375 | 4.66 |
| 84 | | chemdiv4016952 | 4470-0573 | 2950 | 310 | 0.754 |
| 85 | | chemdiv4017354 | 4483-2627 | 2950 | 321 | 3.86 |
| 86 | | chemdiv4030337 | 5167-1580 | 2335 | 328 | 2.46 |

TABLE 2-continued
| ligase_1x9n_docking_233_compounds | COMP_NAME | IDNUMBER | stru | MolW | logP |
|---|---|---|---|---|---|
| 87 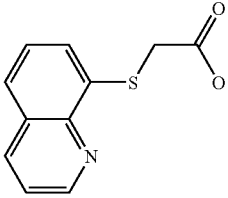 [SMILES: O=C(O)CSc1cccc2cccnc12] | chemdiv4032105 | 5227-2224 | 2335 | 219 | 2.2 |
| 88 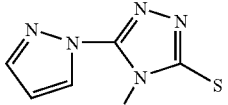 | chemdiv4047092 | 5720-0252 | 2335 | 1.82 | −0.203 |
| 89 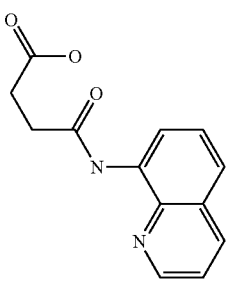 [SMILES: O=C(O)CCC(=O)Nc1cccc2cccnc12] | chemdiv4050365 | 5849-2464 | 2335 | 244 | 0.952 |
| 90 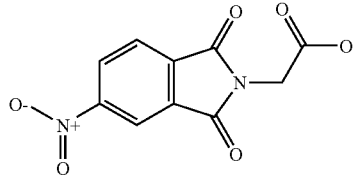 [SMILES: O=C(O)CN1C(=O)c2ccc([N+](=O)[O-])cc2C1=O] | chemdiv4059074 | 6144-0830 | 2335 | 250 | 0.548 |
| 91 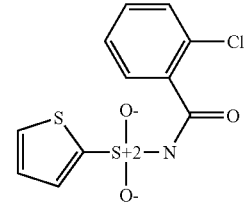 | chemdiv4064940 | 6296-0075 | 2335 | 302 | 2.87 |
| 92 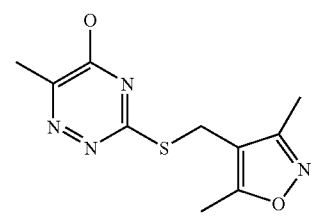 [SMILES: Cc1nnc(SCc2c(C)noc2C)nc1O] | chemdiv4097503 | 6404-0306 | 2950 | 252 | 1.83 |
| 93  | chemdiv4077013 | 7011-1829 | 2950 | 194 | 0.386 |

TABLE 2-continued
| ligase_1x9n_docking_233_compounds | COMP_NAME | IDNUMBER | stru | MolW | logP |
|---|---|---|---|---|---|
| 94 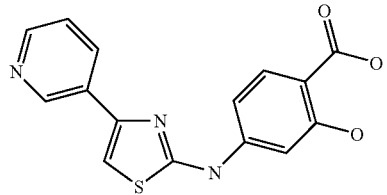 [SMILES: O=C(O)c1ccc(Nc2nc(-c3cccnc3)cs2)cc1O] | chemdiv4077303 | 7100-1148 | 2335 | 313 | 2.36 |
| 95 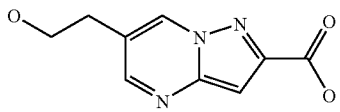 [SMILES: O=C(O)c1cc2ncc(CCO)cn2n1] | chemdiv4077895 | 7213-0775 | 2335 | 207 | −1.01 |
| 96 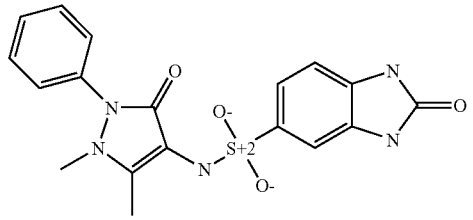 | chemdiv4078007 | 7287-0119 | 2335 | 399 | 0.835 |
| 97 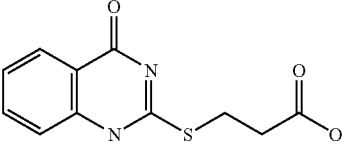 [SMILES: O=C(O)CCSc1nc(=O)c2ccccc2[nH]1] | chemdiv4080636 | 8010-0511 | 2950 | 250 | 2.1 |
| 98 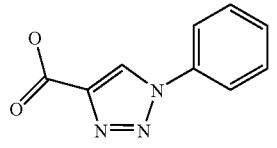 [SMILES: O=C(O)c1cn(-c2ccccc2)nn1] | chemdiv4080731 | 8010-5081 | 2335 | 189 | 0.518 |
| 99 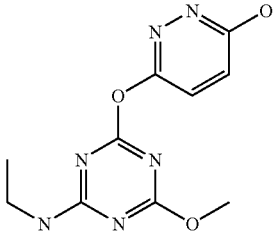 [SMILES: CCNc1nc(OC)nc(Oc2ccc(O)nn2)n1] | chemdiv4084070 | 8013-6158 | 2335 | 264 | 0.637 |
| 100 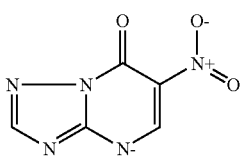 | chemdiv4088658 | 8015-2157 | 2335 | 180 | −1.17 |

| ligase_1x9n_docking_233_compounds | COMP_NAME | IDNUMBER | stru | MolW | logP |
|---|---|---|---|---|---|
| 101 | chemdiv4092369 | 0066-3475 | 2335 | 234 | 0.82 |
| 102 | chemdiv4113108 | C200-0872 | 2335 | 302 | 1.7 |
| 103 | chemdiv4114091 | C200-2517 | 2335 | 277 | 0.282 |
| 104 | chemdiv4115701 | C206-0131 | 2335 | 239 | 2.52 |
| 105 | chemdiv4115760 | C206-0886 | 2950 | 302 | 4.09 |

TABLE 2-continued

| ligase_1x9n_docking_233_compounds | COMP_NAME | IDNUMBER | stru | MolW | logP |
|---|---|---|---|---|---|
| 106 | chemdiv4136188 | C301-1637 | 2950 | 178 | 1.51 |
| 107 | chemdiv4155887 | C455-0040 | 2950 | 258 | 1.39 |
| 108 | chemdiv4178771 | C612-0733 | 2950 | 312 | 1.48 |
| 109 | chemdiv4200659 | C804-0249 | 2950 | 343 | 0.498 |
| 110 | chemdiv4212928 | E546-0207 | 2335 | 287 | 1.24 |
| 111 | chemdiv4226558 | K783-5936 | 2950 | 208 | 0.537 |

TABLE 2-continued

| ligase_1x9n_docking_233_compounds | COMP_NAME | IDNUMBER | stru | MolW | logP |
|---|---|---|---|---|---|
| 112 | chemdiv4247207 | K906-0577 | 2950 | 300 | 1.38 |
| 113 | chemdiv4249937 | K978-1019 | 2335 | 475 | 1.42 |
| 114 | chemdiv4250212 | R052-2665 | 2950 | 163 | −0.321 |
| 115 | chemdiv4250230 | R052-2693 | 2950 | 174 | 0.921 |
| 116 | chemdiv4256344 | C200-2775 | 2950 | 475 | 0.953 |
| 117 | chemdiv4257714 | C430-0780 | 2950 | 227 | 0.861 |

TABLE 2-continued

| | ligase_1x9n_docking_233_compounds | COMP_NAME | IDNUMBER | stru | MolW | logP |
|---|---|---|---|---|---|---|
| 118 | | chemdiv4262012 | C800-0149 | 2950 | 244 | 1.26 |
| 119 | | maybridge0404348 | BTB 06428 | 2950 | 247 | 3.81 |
| 120 | | maybridge0405401 | BTB 08297 | 2950 | 323 | 1.9 |
| 121 | | maybridge0407919 | BTB 13897 | 2335 | 207 | 2.38 |
| 122 | | maybridge0407972 | BTB 14052 | 2950 | 216 | 1.27 |
| 123 | | maybridge0409092 | CD 01419 | 2950 | 228 | 1.51 |
| 124 | | maybridge0414926 | GK 01940 | 2335 | 237 | 1.86 |
| 125 | | maybridge0418520 | HTS 03891 | 2950 | 314 | 2.34 |
| 126 | | maybridge0419334 | HTS 05121 | 2950 | 234 | 0.154 |

TABLE 2-continued

| ligase_1x9n_docking_233_compounds | COMP_NAME | IDNUMBER | stru | MolW | logP |
|---|---|---|---|---|---|
| 127 | maybridge0425599 | JFD 00838 | 2950 | 341 | 1.69 |
| 128 | maybridge0428829 | KM 02107 | 2950 | 250 | 0.522 |
| 129 | maybridge0430404 | KM 05117 | 2950 | 207 | 0.114 |
| 130 | maybridge0434449 | NWP 00580 | 2950 | 189 | 1.07 |
| 131 | maybridge0435308 | NRB 00719 | 2950 | 289 | 2.87 |
| 132 | maybridge0439282 | RF 00190 | 2950 | 215 | 0.428 |
| 133 | maybridge0439473 | RF 00770 | 2950 | 268 | 2.75 |
| 134 | maybridge0440186 | RF 03622 | 2335 | 190 | 1.67 |

TABLE 2-continued

| ligase_1x9n_docking_233_compounds | COMP_NAME | IDNUMBER | stru | MolW | logP |
|---|---|---|---|---|---|
| 135 | maybridge0441358 | RH 00871 | 2950 | 239 | 0.994 |
| 136 | maybridge0442630 | RJC 00691 | 2335 | 183 | 0.161 |
| 137 | maybridge0443763 | RJC 02884 | 2950 | 244 | 2.06 |
| 138 | maybridge0445673 | S 00903 | 2335 | 258 | 4.11 |
| 139 | maybridge0445675 | S 00982 | 2950 | 227 | 3:37 |
| 140 | maybridge0449798 | SCR 01207 | 2950 | 342 | 2.75 |
| 141 | maybridge0454605 | SPB 00315 | 2335 | 167 | 1.14 |
| 142 | maybridge0455528 | SPB 02143 | 2950 | 346 | 2.91 |
| 143 | maybridge0455775 | SPB 02523 | 2950 | 198 | 2.39 |

TABLE 2-continued

| ligase_1x9n_docking_233_compounds | COMP_NAME | IDNUMBER | stru | MolW | logP |
|---|---|---|---|---|---|
| 144 | mdd0506944 | APX000008174 | 2335 | 282 | 3.44 |
| 145 | mdd0507227 | APX000008527 | 2950 | 254 | 3.16 |
| 146 | mdd0507257 | APX000008566 | 2950 | 256 | 1.56 |
| 147 | mdd0525205 | APX000027192 | 2335 | 179 | 0.51 |
| 148 | mdd0528932 | APX000030930 | 2335 | 203 | 0.857 |
| 149 | mdd0531592 | APX000033591 | 2950 | 317 | 1.52 |
| 150 | nanosyn000678 | NS49351 | 2335 | 361 | 3.55 |
| 151 | nanosyn006272 | NS54884 | 2950 | 306 | 0.108 |

TABLE 2-continued

| ligase_1x9n_docking_233_compounds | COMP_NAME | IDNUMBER | stru | MolW | logP |
|---|---|---|---|---|---|
| 152 | nanosyn012438 | NS15117 | 1x9n | 304 | 4.26 |
| 153 | nanosyn019560 | NS0633 | 1x9n | 296 | 2.12 |
| 154 | nanosyn020035 | NS1965 | 2950 | 202 | 2.14 |
| 155 | nanosyn020419 | NS2538 | 2950 | 347 | 0.517 |
| 156 | nanosyn022218 | NS5033 | 2950 | 224 | −1.3 |
| 157 | nanosyn024054 | NS7425 | 2335 | 252 | 1.04 |
| 158 | nanosyn026199 | NS10673 | 2335 | 288 | −0.938 |

TABLE 2-continued

| ligase_1x9n_docking_233_compounds | COMP_NAME | IDNUMBER | stru | MolW | logP |
|---|---|---|---|---|---|
| 159 | nanosyn028817 | NS14410 | 2335 | 305 | 2.9 |
| 160 | nanosyn029397 | NS15310 | 2335 | 312 | 2.96 |
| 161 | nanosyn032970 | NS21015 | 2335 | 246 | 1.61 |
| 162 | nanosyno041421 | NS32415 | 2950 | 200 | −1.14 |
| 163 | nanosyn042848 | NS33842 | 2335 | 254 | 1.25 |
| 164 | nanosyn043053 | NS34047 | 2950 | 209 | 1.02 |
| 165 | nanosyn044719 | NS35713 | 1x9n | 334 | 4.05 |

TABLE 2-continued

| ligase_1x9n_docking_233_compounds | COMP_NAME | IDNUMBER | stru | MolW | logP |
|---|---|---|---|---|---|
| 166 | nanosyn047911 | NS38906 | 2950 | 195 | 0.555 |
| 167 | nanosyn052735 | NS44149 | 2335 | 224 | 0.92 |
| 168 | nanosyn061098 | NS63350 | 1x9n | 253 | 2.32 |
| 169 | nanosyn064176 | NS66483 | 2335 | 289 | 2.57 |
| 170 | nanosyn064661 | NS67013 | 2335 | 269 | 1.3 |
| 171 | specs0087646 | AG-205/12145002 | 2335 | 272 | 0.787 |
| 172 | specs0093768 | AP-845/40883774 | 2950 | 228 | 1.8 |

TABLE 2-continued
| ligase_1x9n_docking_233_compounds | | COMP_NAME | IDNUMBER | stru | MolW | logP |
|---|---|---|---|---|---|---|
| 173 | 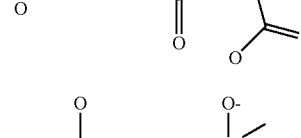 | specs0094412 | AE-641/40197985 | 2950 | 279 | 1.9 |
| 174 | 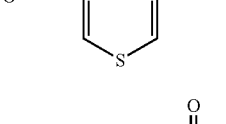 | specs0094816 | AI-942/25121085 | 2950 | 206 | 0.428 |
| 175 | 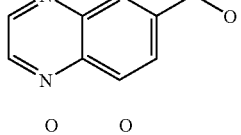 | specs0094999 | AM-807/25050007 | 2335 | 174 | 0.998 |
| 176 | 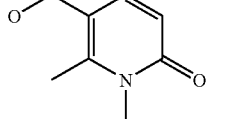 | specs0096856 | AE-406/41056556 | 2335 | 259 | 1.84 |
| 177 | 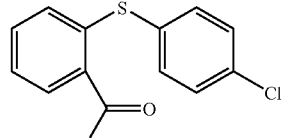 | specs0097907 | AE-641/30103046 | 2335 | 265 | 4.42 |
| 178 | 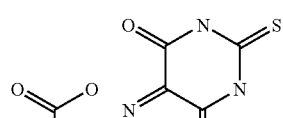 | specs0104444 | AF-399/15335020 | 2335 | 292 | 1.59 |
| 179 | 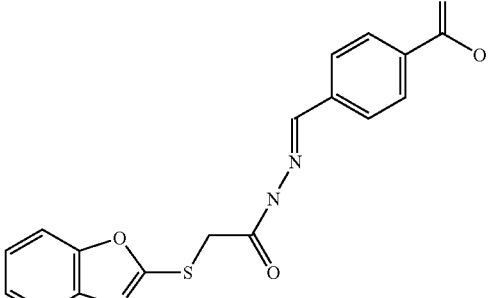 | specs0104985 | AF-399/15393031 | 1x9n | 355 | 3.6 |

TABLE 2-continued

| ligase_1x9n_docking_233_compounds | COMP_NAME | IDNUMBER | stru | MolW | logP |
|---|---|---|---|---|---|
| 180 | specs0112290 | AG-205/15425118 | 2950 | 301 | 2.44 |
| 181 | specs0123459 | AG-690/09793058 | 2335 | 200 | −1.54 |
| 182 | specs0126485 | AG-690/11384661 | 2950 | 291 | −0.44 |
| 183 | specs0129149 | AG-690/12002297 | 2335 | 302 | 2.65 |
| 184 | specs0133795 | AG-690/15436354 | 2950 | 272 | −0.45 |
| 185 | specs0140784 | AG-690/40697266 | 2335 | 345 | 2.84 |
| 186 | specs0142480 | AG-690/40700254 | 2335 | 324 | 2.14 |

TABLE 2-continued

| | ligase_1x9n_docking_233_compounds | COMP_NAME | IDNUMBER | stru | MolW | logP |
|---|---|---|---|---|---|---|
| 187 | | specs0142745 | AG-690/40700684 | 2335 | 354 | 0.846 |
| 188 | | specs0154616 | AI-204/31687014 | 2950 | 216 | 1.29 |
| 189 | | specs4002175 | AC-907/34129012 | 2950 | 246 | 1.84 |
| 190 | | specs4002201 | AC-907/34130009 | 2950 | 270 | 1.54 |
| 191 | | specs4003032 | AE-562/12222186 | 2950 | 344 | 0.148 |
| 192 | | specs4003077 | AE-562/12222297 | 2950 | 274 | 1.56 |

TABLE 2-continued

| ligase_1x9n_docking_233_compounds | COMP_NAME | IDNUMBER | stru | MolW | logP |
|---|---|---|---|---|---|
| 193 | specs4004319 | AE-641/06280018 | 2950 | 311 | 3.11 |
| 194 | specs4007749 | AE-848/30709022 | 2950 | 306 | 2.11 |
| 195 | specs4020536 | AG-205/08231019 | 2235 | 316 | 3.81 |
| 196 | specs4021096 | AG-205/08625012 | 2335 | 273 | 0.787 |
| 197 | specs4028351 | AG-205/32243059 | 2950 | 310 | 1.63 |
| 198 | specs4030921 | AG-205/33652013 | 2950 | 292 | 1.63 |
| 199 | specs4036585 | AG-205/40650755 | 2950 | 362 | 1.61 |
| 200 | specs4039932 | AG-207/37370001 | 2335 | 214 | 2.8 |

TABLE 2-continued
| ligase_1x9n_docking_233_compounds | | COMP_NAME | IDNUMBER | stru | MolW | logP |
|---|---|---|---|---|---|---|
| 201 | 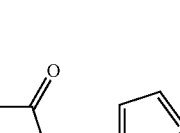 | specs4043054 | AG-670/31548028 | 2950 | 287 | 0.234 |
| 202 | 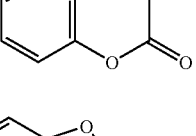 | specs4044861 | AG-690/08639033 | 1x9n | 390 | 4.49 |
| 203 | 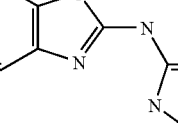 | specs4051894 | AG-690/12844905 | 2950 | 204 | 1.82 |
| 204 | 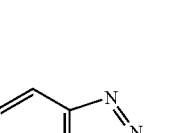 | specs4052603 | AG-690/12885209 | 2950 | 216 | 1.3 |
| 205 | 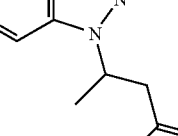 | specs4056295 | AG-690/15433670 | 2950 | 205 | 0.928 |
| 206 | 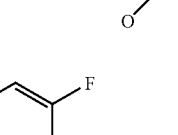 | specs4056597 | Ag-690/15438954 | 2950 | 247 | 0.308 |
| 207 | 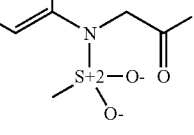 | specs4063372 | AG-690/37215010 | 2950 | 289 | 1.38 |

TABLE 2-continued

| | ligase_1x9n_docking_233_compounds | COMP_NAME | IDNUMBER | stru | MolW | logP |
|---|---|---|---|---|---|---|
| 208 | | specs4073894 | AI-237/31666029 | 2335 | 272 | 0.565 |
| 209 | | specs4074491 | AJ-030/12105064 | 2335 | 370 | −0.561 |
| 210 | | specs4074773 | AJ-087/41885602 | 2950 | 241 | 1.57 |
| 211 | | specs4076821 | AJ-292/41686278 | 1x9n | 366 | 2.78 |
| 212 | | specs4078664 | AJ-333/36115017 | 2950 | 212 | −0.117 |
| 213 | | specs4079101 | AK-087/42718317 | 2950 | 194 | 2.54 |

TABLE 2-continued

| ligase_1x9n_docking_233_compounds | COMP_NAME | IDNUMBER | stru | MolW | logP |
|---|---|---|---|---|---|
| 214 | specs4085187 | AK-918/42409851 | 2950 | 312 | 3.63 |
| 215 | specs4087862 | AK-968/11789151 | 2335 | 297 | 1.28 |
| 216 | specs4103227 | AK-968/41169454 | 2335 | 221 | 2.59. |
| 217 | specs4103395 | AK-968/41170109 | 2335 | 219 | 0.442 |
| 218 | specs4121778 | AN-465/41521127 | 2950 | 226 | 1.49 |
| 219 | specs4132753 | AN-829/13872035 | 2950 | 196 | −0.689 |
| 220 | specs4133908 | AN-979/15013141 | 2335 | 331 | 1.81 |

TABLE 2-continued
| ligase_1x9n_docking_233_compounds | | COMP_NAME | IDNUMBER | stru | MolW | logP |
|---|---|---|---|---|---|---|
| 221 | 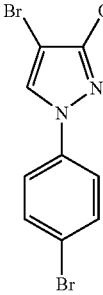 | specs4136100 | AO-080/42479361 | 2950 | 318 | 3.23 |
| 222 | 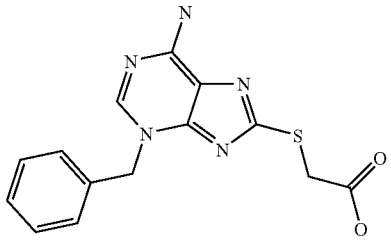 [SMILES: Nc1ncn(Cc2ccccc2)c2nc(SCC(=O)O)nc1-2] | specs4156297 | AR-422/41026969 | 2335 | 315 | 1.36 |
| 223 | 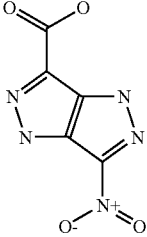 [SMILES: O=C(O)c1n[nH]c2c([N+](=O)[O-])n[nH]c12] | st007595 | st008467 | 2335 | 197 | 1.3 |
| 224 | 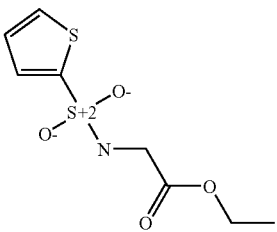 | tripos0034247 | 1525-00782 | 2950 | 249 | 0.974 |
| 225 | 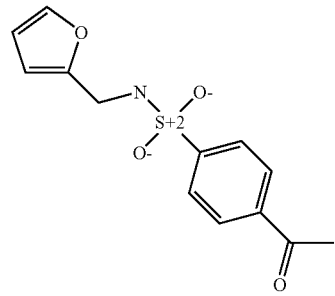 | tripos0034504 | 1525-01725 | 2335 | 279 | 1.36 |

TABLE 2-continued

| ligase_1x9n_docking_233_compounds | COMP_NAME | IDNUMBER | stru | MolW | logP |
|---|---|---|---|---|---|
| 226 | tripos0046768 | 1528-02292 | 2335 | 301 | 0.506 |
| 227 | tripos0047216 | 1528-03826 | 2950 | 342 | 3.44 |
| 228 | tripos0047548 | 1528-04508 | 2335 | 258 | 2.35 |
| 229 | tripos0049773 | 1528-10011 | 2950 | 336 | 2.6 |
| 230 | tripos0049952 | 1528-10605 | 2950 | 279 | 2.27 |
| 231 | tripos0052524 | 1533-00601 | 1x9n | 231 | 1.08 |

TABLE 2-continued
| ligase_1x9n_docking_233_compounds | COMP_NAME | IDNUMBER | stru | MolW | logP |
|---|---|---|---|---|---|
| 232 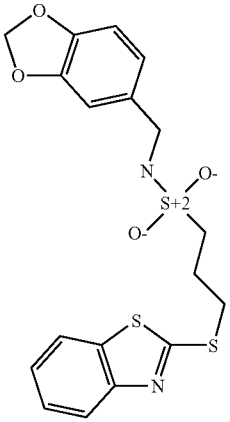 | tripos0053972 | 1533-06492 | 2335 | 423 | 4.12 |
| 233 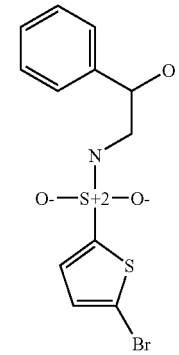 | tripos0074665 | 1554-07198 | 1x9n | 362 | 3.09 |
TABLE 8
| ligase64 chemdiv0333435 75 | COMP NAME | IDNUMBER | MW | a | d | logP |
|---|---|---|---|---|---|---|
| 1 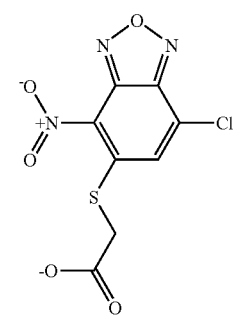 | chemdiv0333435 | R052-1644 | 286.6 | 2. | 0. | 2.15 |
| 2 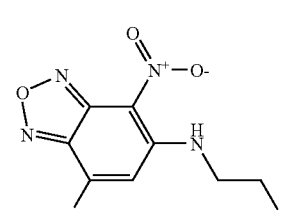 | chembridge0127433 | 5241477 | 258.6 | 3. | 2. | 0.88 |

TABLE 8-continued
| | ligase64 chemdiv0333435 75 | COMP NAME | IDNUMBER | MW | a | d | logP |
|---|---|---|---|---|---|---|---|
| 3 | 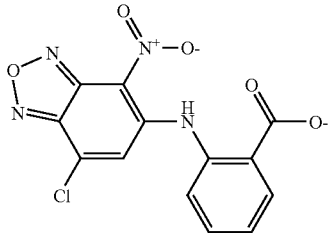 [SMILES: O=C([O-])c1ccccc1Nc1cc(Cl)c2nonc2c1[N+](=O)[O-]] | chembridge017871 | 5241438 | 333.6 | 2. | 1. | 3.11 |
| 4 | 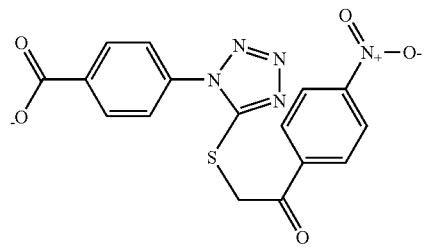 | chembridge0224352 | 6640684 | 384.3 | 4. | 0. | 2.35 |
| 5 | 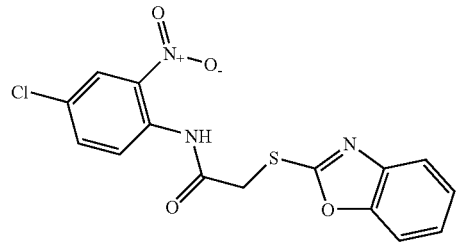 [SMILES: O=C(CSc1nc2ccccc2o1)Nc1ccc(Cl)cc1[N+](=O)[O-]] | chembridge0252784 | 6208029 | 363.7 | 2. | 1. | 3.65 |
| 6 | 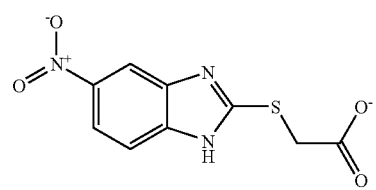 | chembridge0318761 | 7399643 | 252.2 | 2. | 2. | 1.85 |
| 7 | 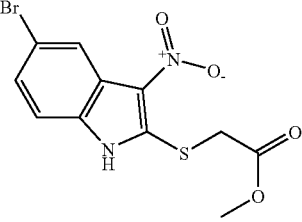 [SMILES: COC(=O)CSc1[nH]c2ccc(Br)cc2c1[N+](=O)[O-]] | chembridge0350072 | 7684126 | 345.1 | 1. | 1. | 3.81 |
| 8 | 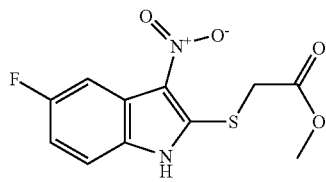 [SMILES: COC(=O)CSc1[nH]c2ccc(F)cc2c1[N+](=O)[O-]] | chembridge0353163 | 7703755 | 284.2 | 1. | 1. | 3.16 |

TABLE 8-continued

| | ligase64 chemdiv0333435 75 | COMP NAME | IDNUMBER | MW | a | d | logP |
|---|---|---|---|---|---|---|---|
| 9 | | chembridge0361286 | 7749202 | 295.2 | 3. | 2. | 2.81 |
| 10 | | chembridge0410035 | 7963899 | 441.3 | 5. | 0. | 2.20 |
| 11 | | chembridge057754 | 5556669 | 269.2 | 1. | 0. | 2.72 |
| 12 | | chemdiv0235647 | 8012-5585 | 418.8 | 4. | 2. | 3.62 |
| 13 | | chemdiv029346 | 8002-5557 | 216.2 | 1. | 0. | 0.99 |
| 14 | | chemdiv195033 | K061-1138 | 218.5 | 1. | 0. | 0.70 |

TABLE 8-continued

| ligase64 chemdiv0333435 75 | COMP NAME | IDNUMBER | MW | a | d | logP |
|---|---|---|---|---|---|---|
| 15 | chemdiv202374 | R052-0733 | 254.2 | 2. | 0. | 1.52 |
| 16 | chemdiv4039985 | 5555-0004 | 216.2 | 2. | 2. | 0.94 |
| 17 | chemdiv4228031 | K784-6223 | 364.3 | 3. | 2. | 3.13 |
| 18 | chemdiv4230965 | K786-1157 | 300.6 | 3. | 1. | 1.47 |
| 19 | chemdiv4231246 | K786-1552 | 408.8 | 3. | 1. | 3.72 |

TABLE 8-continued

| | ligase64 chemdiv0333435 75 | COMP NAME | IDNUMBER | MW | a | d | logP |
|---|---|---|---|---|---|---|---|
| 20 | | maybridge0431189 | KM = 06791 | 257.2 | 3. | 1. | 2.02 |
| 21 | | maybridge0431220 | KM = 06833 | 241.2 | 3. | 1. | 1.20 |
| 22 | | maybridge0431223 | KM = 06837 | 291.2 | 2. | 0. | 3.70 |
| 23 | | maybridge0431242 | KM = 06873 | 363.3 | 3. | 0. | 3.61 |
| 24 | | maybridge0431243 | KM = 06874 | 345.3 | 3. | 0. | 3.45 |
| 25 | | maybridge0431901 | KM = 08121 | 213.1 | 1. | 0. | 1.23 |

TABLE 8-continued
| | ligase64 chemdiv0333435 75 | COMP NAME | IDNUMBER | MW | a | d | logP |
|---|---|---|---|---|---|---|---|
| 26 | 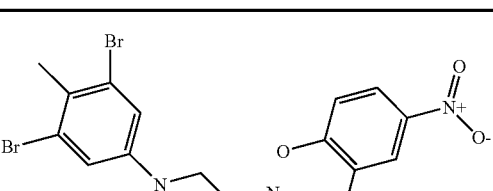 | specs0118592 | AG-227/40703560 | 347.7 | 3. | 1. | 3.59 |
| 27 | | specs4043497 | AG-670/36154046 | 359.3 | 2. | 2. | 3.64 |
| 28 | | specs4099247 | AK-968/37166230 | 294.6 | 1. | 0. | 2.66 |
TABLE 9
| | ligase-67-chemdiv102812-similar90 | COMP_NAME | IDNUMBER | Weight | logP(o/w) |
|---|---|---|---|---|---|
| 1 | 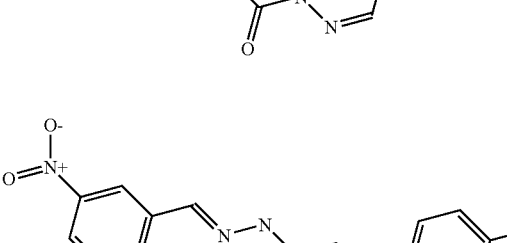 | chemdiv102812 | 1761-0019 | 486.12 | 4.794 |
| 2 | | chembridge0139405 | 5724812 | 423.22 | 3.619 |

TABLE 9-continued

| ligase-67-chemdiv102812-similar90 | COMP_NAME | IDNUMBER | Weight | logP(o/w) |
|---|---|---|---|---|
| 3 | chembridge0163789 | 6046146 | 516.15 | 4.785 |
| 4 | chembridge061292 | 5575463 | 407.22 | 3.959 |
| 5 | chembridge091422 | 5863488 | 414.42 | 5.27 |
| 6 | chemdiv0304474 | 8004-4208 | 547.36 | 6.79 |
| 7 | chemdiv030710 | 8002-9168 | 449.26 | 3.468 |
| 8 | chemdiv031476 | 8003-1205 | 405.3 | 2.642 |

TABLE 9-continued

| ligase-67-chemdiv102812-similar90 | COMP_NAME | IDNUMBER | Weight | logP(o/w) |
|---|---|---|---|---|
| 9 | chemdiv031594 | 8003-1363 | 542.3 | 5.168 |
| 10 | chemdiv032220 | 8003-2671 | 390.78 | 3.338 |
| 11 | chemdiv034545 | 8004-0876 | 407.22 | 3.961 |
| 12 | chemdiv036531 | 8004-5914 | 373.32 | 3.096 |
| 13 | chemdiv038132 | 8005-0790 | 421.21 | 3.278 |
| 14 | chemdiv042897 | 8006-1915 | 360.3 | 2.672 |

TABLE 9-continued

| | ligase-67-chemdiv102812-similar90 | COMP_NAME | IDNUMBER | Weight | logP(o/w) |
|---|---|---|---|---|---|
| 15 | | chemdiv042898 | 8006-1916 | 376.76 | 3.074 |
| 16 | | chemdiv042910 | 8006-1930 | 360.3 | 2.672 |
| 17 | | chemdiv043057 | 8006-2113 | 515.31 | 5.569 |
| 18 | | chemdiv088176 | 1359-0042 | 419.23 | 3.514 |
| 19 | | chemdiv102882 | 1761-0255 | 486.12 | 4.794 |
| 20 | | chemdiv103694 | 1761-1563 | 421.25 | 4.704 |

TABLE 9-continued
| | ligase-67-chemdiv102812-similar90 | COMP_NAME | IDNUMBER | Weight | logP(o/w) |
|---|---|---|---|---|---|
| 21 | 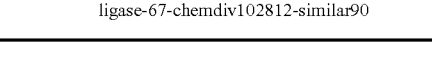 | chemdiv159407 | 3284-0676 | 378.77 | 3.45 |
TABLE 10
| | ligase 78 chemdiv4003854 83 | COMP NAME | IDNUMBER | cl... | MW | loqP |
|---|---|---|---|---|---|---|
| 1 | 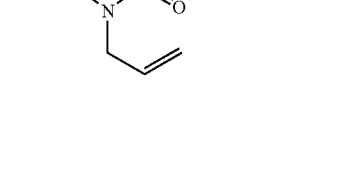 | chemdiv4003854 | 2672-0239 | 1.00 | 320. | 2.97 |
| 2 | 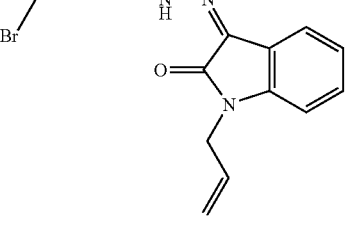 | chembridge066517 | 5635200 | 12.0 | 399. | 3.81 |
| 3 | 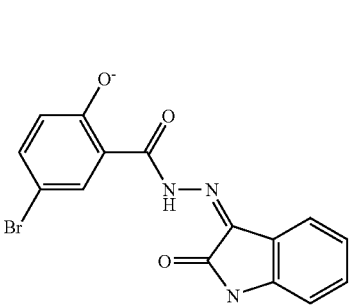 | chembridge066825 | 5637177 | 13.0 | 449. | 4.93 |

TABLE 10-continued

| | ligase 78 chemdiv4003854 83 | COMP NAME | IDNUMBER | cl... | MW | loqP |
|---|---|---|---|---|---|---|
| 4 | | chembridge081742 | 5756943 | 15.0 | 384. | 4.19 |
| 5 | | chembridge084110 | 5785385 | 17.0 | 308. | 2.65 |
| 6 | | chemdiv030495 | 8002-8328 | 19.0 | 385. | 4.24 |
| 7 | | chemdiv049350 | 8010-0528 | 16.0 | 358. | 3.87 |
| 8 | | chemdiv049352 | 8010-0530 | 21.0 | 337. | 1.94 |

TABLE 10-continued

| | ligase 78 chemdiv4003854 83 | COMP NAME | IDNUMBER | cl... | MW | loqP |
|---|---|---|---|---|---|---|
| 9 | | chemdiv070385 | 0784-0310 | 22.0 | 413. | 3.09 |
| 10 | | chemdiv070399 | 0784-0352 | 10.0 | 370. | 4.10 |
| 11 | | chemdiv080501 | 1094-0055 | 30.0 | 319. | 3.50 |
| 12 | | chemdiv080519 | 1094-0096 | 31.0 | 305. | 3.16 |

TABLE 10-continued

| | ligase 78 chemdiv4003854 83 | COMP NAME | IDNUMBER | cl... | MW | loqP |
|---|---|---|---|---|---|---|
| 13 | | chemdiv080520 | 1094-0097 | 30.0 | 319. | 3.46 |
| 14 | | chemdiv080523 | 1094-0100 | 35.0 | 320. | 2.49 |
| 15 | | chemdiv080527 | 1094-0104 | 1.00 | 320. | 2.97 |
| 16 | | chemdiv080533 | 1094-0112 | 1.00 | 370. | 4.27 |

TABLE 10-continued
| | ligase 78 chemdiv4003854 83 | COMP NAME | IDNUMBER | cl... | MW | loqP |
|---|---|---|---|---|---|---|
| 17 | 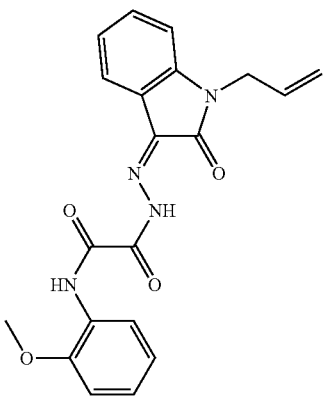 [SMILES: C=CCN1C(=O)/C(=N\NC(=O)C(=O)Nc2ccccc2OC)c2ccccc21] | chemdiv080539 | 1094-0122 | 41.0 | 378. | 2.11 |
| 18 | 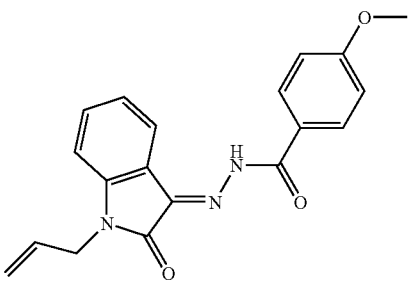 [SMILES: C=CCN1C(=O)/C(=N/NC(=O)c2ccc(OC)cc2)c2ccccc21] | chemdiv085129 | 1270-0044 | 46.0 | 335. | 3.12 |
| 19 | 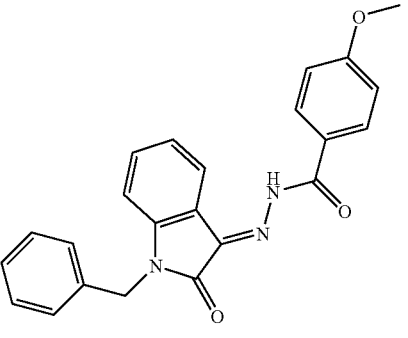 [SMILES: COc1ccc(C(=O)N/N=C2/C(=O)N(Cc3ccccc3)c3ccccc32)cc1] | chemdiv085130 | 1270-0045 | 47.0 | 385. | 4.24 |
| 20 | 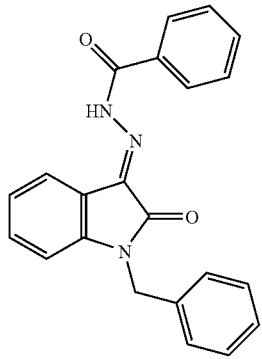 [SMILES: O=C(N/N=C1/C(=O)N(Cc2ccccc2)c2ccccc21)c1ccccc1] | chemdiv105653 | 1783-0201 | 52.0 | 355. | 4.29 |

TABLE 10-continued
| | ligase 78 chemdiv4003854 83 | COMP NAME | IDNUMBER | cl... | MW | loqP |
|---|---|---|---|---|---|---|
| 21 | 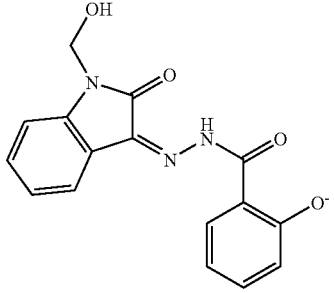 [SMILES: O=C(N/N=C1\C(=O)N(CO)c2ccccc21)c1ccccc1[O-]] | chemdiv133102 | 2395-0012 | 57.0 | 310. | 1.73 |
| 22 | 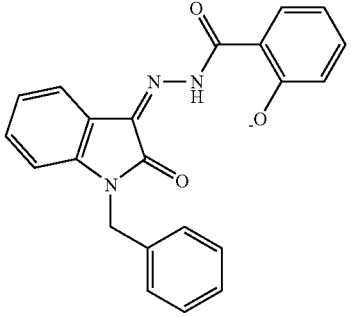 | chemdiv4003850 | 2672-0163 | 10.0 | 370. | 4.10 |
| 23 | 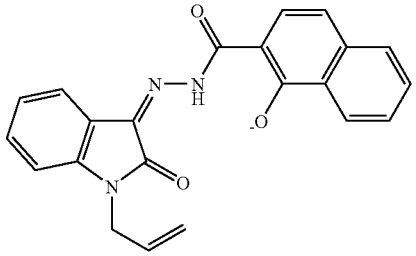 | chemdiv4003855 | 2672-0240 | 1.00 | 370. | 4.19 |
| 24 | 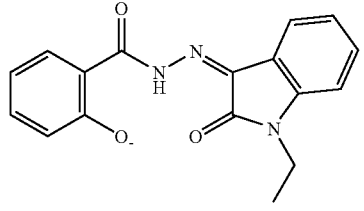 [SMILES: CCN1C(=O)/C(=N\NC(=O)c2ccccc2[O-])c2ccccc21] | chemdiv4019950 | 455S-4523 | 16.0 | 308. | 2.65 |
| 25 | 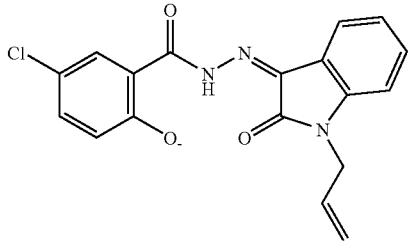 [SMILES: C=CCN1C(=O)/C(=N\NC(=O)c2cc(Cl)ccc2[O-])c2ccccc21] | chemdiv4021425 | 4632-6961 | 70.0 | 354. | 3.60 |
| 26 | 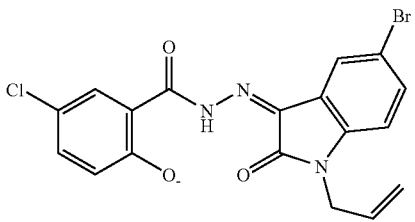 [SMILES: C=CCN1C(=O)/C(=N\NC(=O)c2cc(Cl)ccc2[O-])c2cc(Br)ccc21] | chemdiv4021435 | 4632-6987 | 72.0 | 433. | 4.44 |

TABLE 10-continued

| | ligase 78 chemdiv4003854 83 | COMP NAME | IDNUMBER | cl . . . | MW | loqP |
|---|---|---|---|---|---|---|
| 27 | | chemdiv4021439 | 4632-7005 | 75.0 | 404. | 4.73 |
| 28 | | specs0122994 | AG-690/09504058 | 117. | 414. | 2.97 |

TABLE 11

| | Ligase_active#113_chemdiv4249937 | COMP_NAME | IDNUMBER | MW | logP | 8585 |
|---|---|---|---|---|---|---|
| 1 | | 113_chemdiv4249937 | K978-1019 | 475 | 1.42 | 1 |

TABLE 11-continued

| | Ligase_active#113_chemdiv4249937 | COMP_NAME | IDNUMBER | MW | logP | 8585 |
|---|---|---|---|---|---|---|
| 2 | (structure) | amb_c0025720 | A2357/0099549 | 393 | 3.31 | 1 |
| 3 | (structure) | amb_c0045243 | AmblieP-559829 | 321 | 0.481 | 3 |
| 4 | (structure) | amb_d022599 | A2357/0099549 | 393 | 3.31 | 1 |
| 5 | (structure) | amb_e0017501 | ASKBASE/24046 | 321 | 0.481 | 3 |
| 6 | (structure) | amb_e0021248 | ASKBASE/28478 | 383 | 2.31 | 6 |
| 7 | (structure) | amb_e0021385 | ASKBASE/28630 | 318 | 1.6 | 7 |
| 8 | (structure) | amb_e0023055 | ASKBASE/30341 | 383 | 2.31 | 8 |

TABLE 11-continued

| Ligase_active#113_chemdiv4249937 | COMP_NAME | IDNUMBER | MW | logP | 8585 |
| --- | --- | --- | --- | --- | --- |
| 9 | amb_e0023957 | ASKBASE/31261 | 383 | 2.34 | 8 |
| 10 | amb_e0025034 | ASKBASK/32342 | 335 | 0.569 | 10 |
| 11 | amb_e0025080 | ASKBASE/32388 | 353 | 2.19 | 1 |
| 12 | amb_e0025103 | ASKBASE/32411 | 397 | 2.39 | 1 |
| 13 | amb_e0025149 | ASKBASE/32457 | 332 | 1.68 | 13 |
| 14 | asinex59633 | BAS=0138030 | 638 | 7.73 | 14 |
| 15 | chembridge0216275 | 6584322 | 383 | 2.34 | 8 |

TABLE 11-continued

| Ligase_active#113_chemdiv4249937 | COMP_NAME | IDNUMBER | MW | logP | 8585 |
|---|---|---|---|---|---|
| 16 | chembridge0216484 | 6585646 | 383 | 2.31 | 8 |
| 17 | chembridge0218325 | 6599029 | 332 | 1.68 | 13 |
| 18 | chembridge0258673 | 6620392 | 353 | 2.19 | 1 |
| 19 | chembridge0266367 | 6831135 | 350 | 1.93 | 7 |
| 20 | chembridge0318078 | 7390552 | 338 | 2.4 | 20 |
| 21 | chembridge0368775 | 7788404 | 443 | 4.64 | 1 |

TABLE 11-continued

| Ligase_active#113_chemdiv4249937 | COMP_NAME | IDNUMBER | MW | logP | 8585 |
|---|---|---|---|---|---|
| 22 | chembridge0372356 | 7802552 | 423 | 4.14 | 1 |
| 23 | chembridge0408597 | 7957540 | 421 | 4.19 | 1 |
| 24 | chemdiv0315353 | 8012-8697 | 421 | 4.19 | 1 |
| 25 | chemdiv0324687 | K781-2046 | 367 | 2.68 | 1 |
| 26 | chemdiv0324691 | K781-2050 | 401 | 3.28 | 1 |
| 27 | chemdiv0325214 | K781-4155 | 415 | 2.95 | 27 |
| 28 | chemdiv0325222 | K781-4171 | 397 | 2.8 | 1 |

TABLE 11-continued

| | Ligase_active#113_chemdiv4249937 | COMP_NAME | IDNUMBER | MW | logP | 8585 |
|---|---|---|---|---|---|---|
| 29 | (4-bromophenyl)sulfonyl-N-propanamide with 3-chlorobenzyl | chemdiv0325224 | K781-4177 | 446 | 3.48 | 29 |
| 30 | (4-bromophenyl)sulfonyl-N-propanamide with 4-methylbenzyl | chemdiv0325227 | K781-4185 | 411 | 3.1 | 27 |
| 31 | (4-fluorophenyl)sulfonyl-N-propanamide with phenethyl | chemdiv0325238 | K781-4295 | 350 | 2.24 | 1 |
| 32 | (4-bromophenyl)sulfonyl-N-hexanamide with cyclohexenylethyl | chemdiv0325309 | K781-4963 | 457 | 3.7 | 32 |

TABLE 11-continued

| | Ligase_active#113_chemdiv4249937 | COMP_NAME | IDNUMBER | MW | logP | 8585 |
|---|---|---|---|---|---|---|
| 33 | (structure) | chemdiv0325311 | K781-4969 | 457 | 4.28 | 1 |
| 34 | (structure) | chemdiv0325312 | K781-4973 | 488 | 4.81 | 1 |
| 35 | (structure) | chemdiv0325313 | K781-4974 | 389 | 3 | 32 |

TABLE 11-continued
| Ligase_active#113_chemdiv4249937 | | COMP_NAME | IDNUMBER | MW | logP | 8585 |
|---|---|---|---|---|---|---|
| 36 | 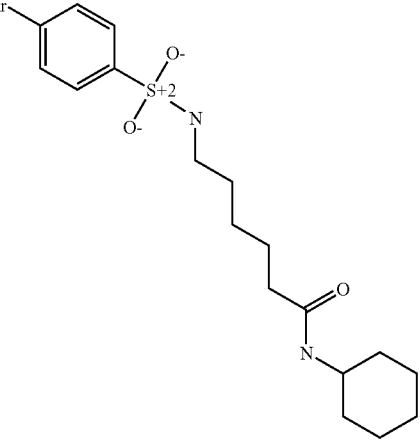 | chemdiv0325316 | K781-4979 | 431 | 4.32 | 1 |
| 37 | 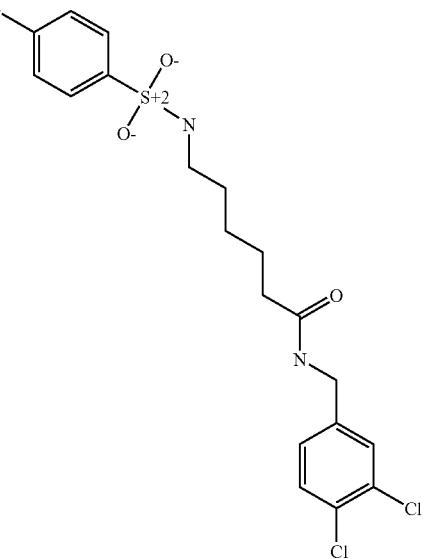 | chemdiv0325317 | K781-4981 | 508 | 5.35 | 1 |
| 38 | 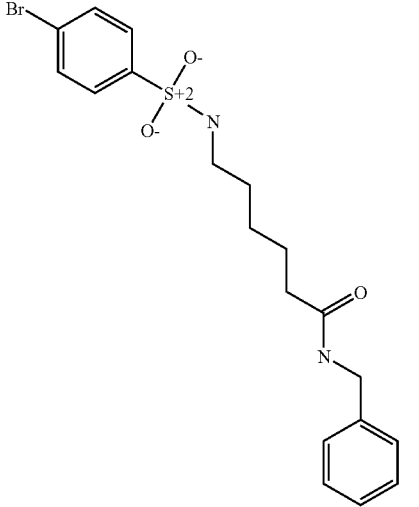 | chemdiv0325318 | K781-4982 | 439 | 4.13 | 1 |

TABLE 11-continued
| Ligase_active#113_chemdiv4249937 | | COMP_NAME | IDNUMBER | MW | logP | 8585 |
|---|---|---|---|---|---|---|
| 39 | 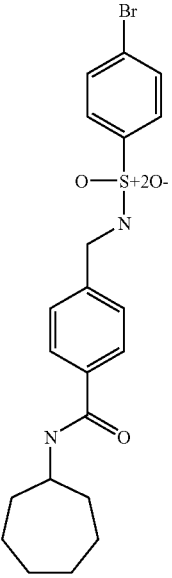 | chemdiv0326079 | K783-0131 | 465 | 5.31 | 39 |
| 40 | 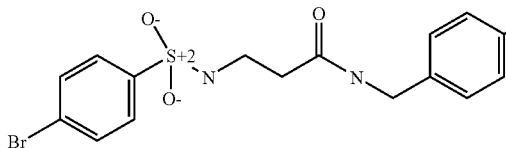 | chemdiv0328145 | K784-4328 | 432 | 3.39 | 27 |
| 41 | 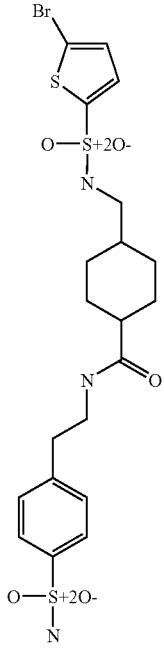 | chemdiv4130154 | C274-3672 | 565 | 2.95 | 41 |

TABLE 11-continued

| Ligase_active#113_chemdiv4249937 | COMP_NAME | IDNUMBER | MW | logP | 8585 |
|---|---|---|---|---|---|
| 42 | chemdiv4148442 | C382-0316 | 479 | 5.75 | 39 |
| 43 | chemdiv4148450 | C382-0342 | 451 | 4.86 | 1 |
| 44 | chemdiv4225320 | K781-4165 | 411 | 2.89 | 1 |
| 45 | chemdiv4225426 | K783-0142 | 437 | 4.42 | 39 |

… 
TABLE 11-continued
| Ligase_active#113_chemdiv4249937 | | COMP_NAME | IDNUMBER | MW | logP | 8585 |
|---|---|---|---|---|---|---|
| 46 | 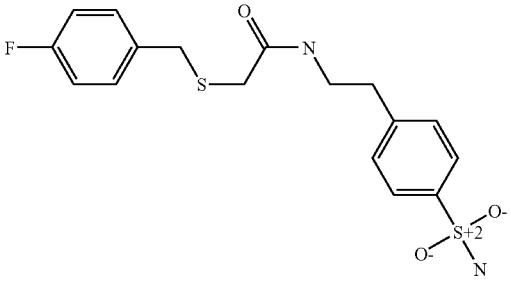 | chemdiv4234898 | K786-6828 | 382 | 2.22 | 46 |
| 47 | 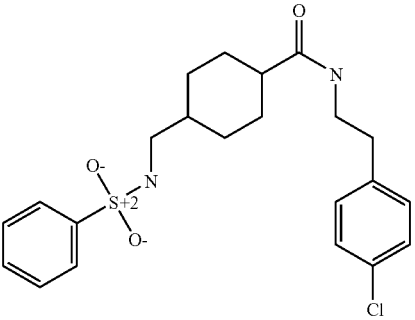 [SMILES: O=C(NCCc1ccc(Cl)cc1)C1CCC(CN[S+2]([O-])([O-])c2ccccc2)CC1] | chemdiv4238958 | K788-2181 | 435 | 4.24 | 1 |
| 48 | 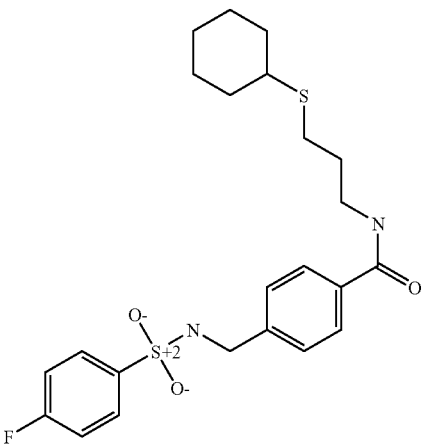 [SMILES: O=C(NCCCSC1CCCCC1)c1ccc(CN[S+2]([O-])([O-])c2ccc(F)cc2)cc1] | chemdiv4239059 | K788-2347 | 465 | 5.22 | 1 |
| 49 | 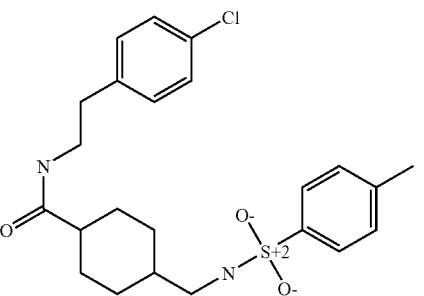 | chemdiv4239292 | K788-2747 | 449 | 4.54 | 1 |
| 50 | 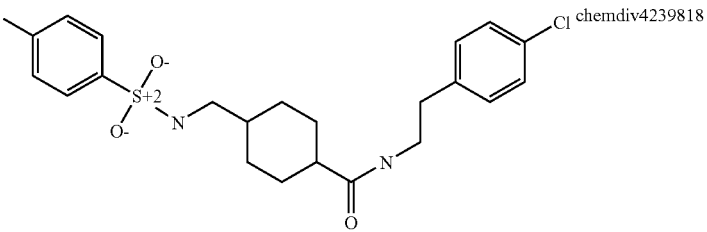 | chemdiv4239818 | K788-3519 | 469 | 4.84 | 1 |

TABLE 11-continued

| Ligase_active#113_chemdiv4249937 | COMP_NAME | IDNUMBER | MW | logP | 8585 |
|---|---|---|---|---|---|
| 51 | chemdiv4239820 | K788-3521 | 487 | 5.34 | 1 |
| 52 | chemdiv4248907 | K938-0642 | 419 | 3.81 | 1 |
| 53 | chemdiv4248970 | K938-0786 | 435 | 4.24 | 1 |

TABLE 11-continued

| Ligase_active#113_chemdiv4249937 | COMP_NAME | IDNUMBER | MW | logP | 8585 |
|---|---|---|---|---|---|
| 54 | comgenex029401 | CGX-0399491 | 441 | 4.33 | 1 |
| 55 | specs0087828 | AG-205/41005779 | 421 | 4.19 | 1 |
| 56 | specs4072254 | AH-487/42307105 | 435 | 4.84 | 1 |
| 57 | specs4072408 | AH-487/42483123 | 457 | 5.11 | 1 |
| 58 | specs4072415 | AH-487/42483920 | 457 | 4.73 | 1 |
| 59 | specs4072424 | AH-487/42485536 | 457 | 4.73 | 1 |

TABLE 11-continued
| Ligase_active#113_chemdiv4249937 | COMP_NAME | IDNUMBER | MW | logP | 8585 |
|---|---|---|---|---|---|
| 60 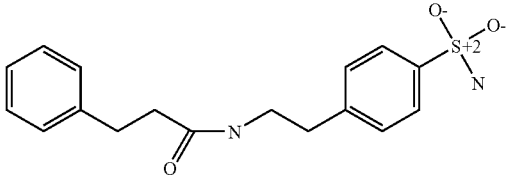 [SMILES: N[S+2]([O-])([O-])c1ccc(CCNC(=O)CCc2ccccc2)cc1] | specs4077937 | AJ-292/42062402 | 332 | 1.68 | 13 |
| 61 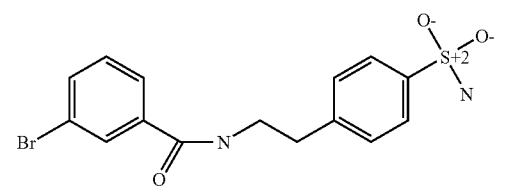 [SMILES: N[S+2]([O-])([O-])c1ccc(CCNC(=O)c2cccc(Br)c2)cc1] | specs4077961 | AJ-292/42062682 | 383 | 2.34 | 8 |
| 62 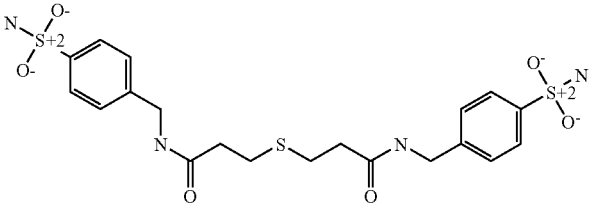 [SMILES: N[S+2]([O-])([O-])c1ccc(CNC(=O)CCSCCC(=O)NCc2ccc([S+2](N)([O-])[O-])cc2)cc1] | specs4108021 | AK-968/41927486 | 515 | -0.294 | 62 |
| 63 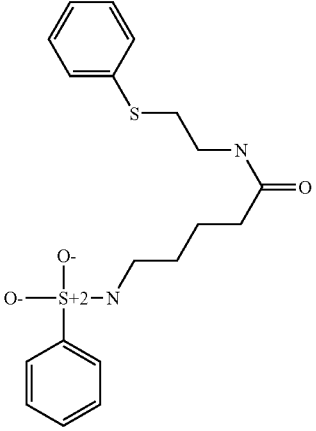 | specs4135786 | AO-080/41280680 | 393 | 3.31 | 1 |
| 64 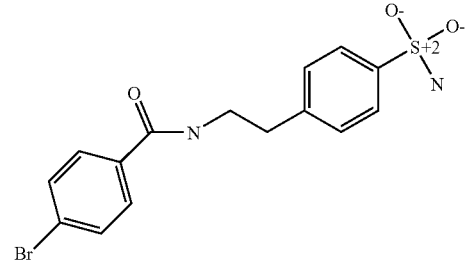 [SMILES: N[S+2]([O-])([O-])c1ccc(CCNC(=O)c2ccc(Br)cc2)cc1] | timtt031879 | ST031879 | 383 | 2.31 | 8 |
| 65 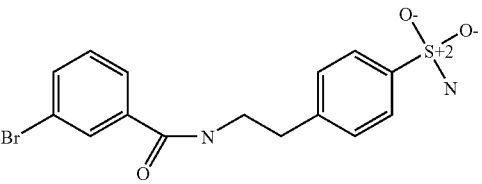 [SMILES: N[S+2]([O-])([O-])c1ccc(CCNC(=O)c2cccc(Br)c2)cc1] | timtt044045 | ST044045 | 383 | 2.34 | 8 |

TABLE 11-continued
| Ligase_active#113_chemdiv4249937 | COMP_NAME | IDNUMBER | MW | logP | 8585 |
|---|---|---|---|---|---|
| 66 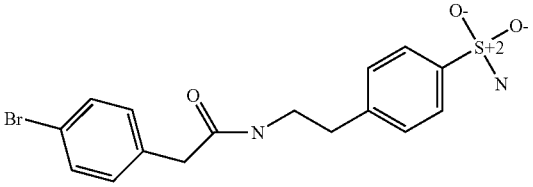 | timtt044162 | ST044162 | 397 | 2.39 | 1 |
| 67 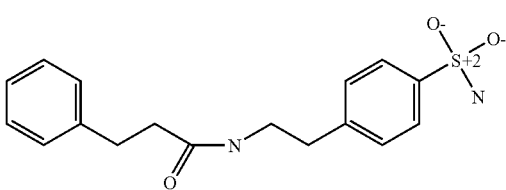 [SMILES: N[S+2]([O-])([O-])c1ccc(CCNC(=O)CCc2ccccc2)cc1] | timtt044167 | ST044167 | 332 | 1.68 | 13 |
| 68 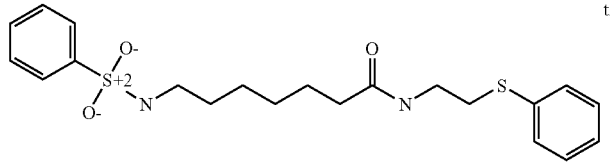 | timtt045785 | ST045785 | 421 | 4.19 | 1 |
| 69 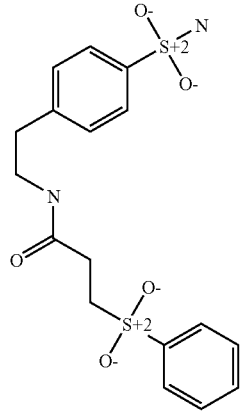 [SMILES: N[S+2]([O-])([O-])c1ccc(CCNC(=O)CC[S+2]([O-])([O-])c2ccccc2)cc1] | tripos0051110 | 1532-03029 | 396 | 0.623 | 13 |
| 70 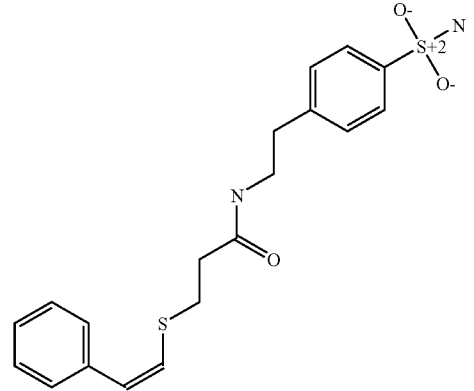 [SMILES: N[S+2]([O-])([O-])c1ccc(CCNC(=O)CCS/C=C\c2ccccc2)cc1] | tripos0051115 | 1532-03050 | 391 | 2.38 | 13 |

TABLE 12

| | ligase 151 nanosyn006272 s85 | COMP NAME | IDNUMBER | logP | MW |
|---|---|---|---|---|---|
| 1 | | nanosyn006272 | NS54884 | 0.11 | 306. |
| 2 | | chembridge-0136013 | 5648015 | -0.42 | 263. |
| 3 | | chembridge-0139327 | 5722560 | 2.90 | 373. |
| 4 | | chembridge-065828 | 5630267 | 0.46 | 304. |
| 5 | | chembridge-070734 | 5663902 | 0.45 | 386. |
| 6 | | chembridge-073257 | 5677048 | -0.20 | 307. |

TABLE 12-continued

| | ligase 151 nanosyn006272 s85 | COMP NAME | IDNUMBER | logP | MW |
|---|---|---|---|---|---|
| 7 | | chembridge-074051 | 5681228 | 0.92 | 321. |
| 8 | | chemdiv-0227504 | 4487-0452 | -0.19 | 277. |
| 9 | | chemdiv-023628 | 8001-0622 | 0.31 | 304. |
| 10 | | chemdiv-0308002 | 8008-5425 | 2.16 | 366. |
| 11 | | chemdiv-037566 | 8004-9459 | 0.31 | 320. |
| 12 | | chemdiv-085124 | 1270-0021 | 3.07 | 458. |
| 13 | | chemdiv-103764 | 1761-1799 | 2.34 | 366. |
| 14 | | chemdiv-103782 | 1761-1819 | 0.11 | 306. |

TABLE 12-continued

| | ligase 151 nanosyn006272 s85 | COMP NAME | IDNUMBER | logP | MW |
|---|---|---|---|---|---|
| 15 | | chemdiv-103828 | 1761-1952 | 1.01 | 324. |
| 16 | | chemdiv-103830 | 1761-1954 | 0.64 | 304. |
| 17 | | chemdiv-103836 | 1761-1961 | 1.10 | 368. |

TABLE 12-continued
| | ligase 151 nanosyn006272 s85 | COMP NAME | IDNUMBER | logP | MW |
|---|---|---|---|---|---|
| 18 | 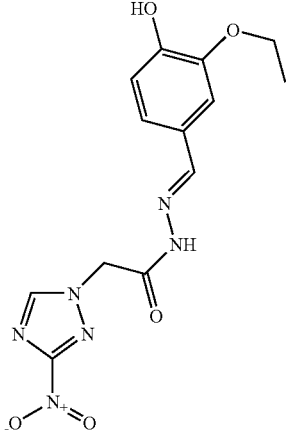 | chemdiv-103848 | 1761-1976 | 0.71 | 334. |
| 19 | 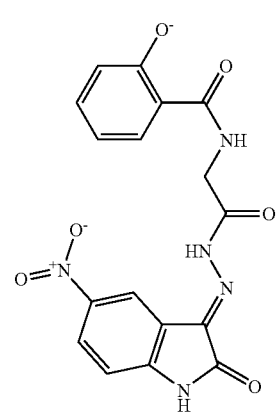 [SMILES: O=C(CNC(=O)c1ccccc1[O-])N/N=C1/C(=O)Nc2ccc([N+](=O)[O-])cc21] | chemdiv-106079 | 1805-1308 | 1.21 | 382. |
| 20 | 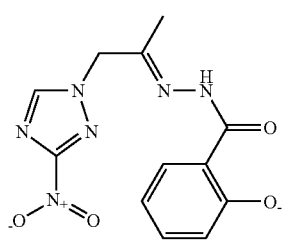 | chemdiv-108507 | 1897-1408 | 0.43 | 303. |
| 21 | 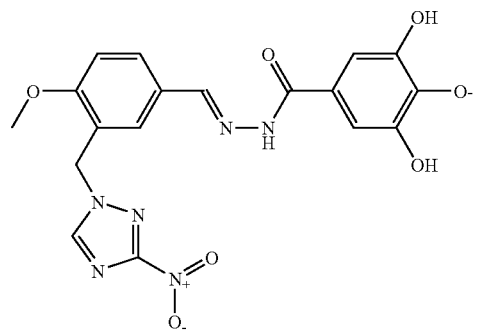 [SMILES: COc1ccc(/C=N/NC(=O)c2cc(O)c([O-])c(O)c2)cc1Cn1cnc([N+](=O)[O-])n1] | chemdiv-110779 | 1981-1490 | 1.91 | 427. |

TABLE 12-continued

| | ligase 151 nanosyn006272 s85 | COMP NAME | IDNUMBER | logP | MW |
|---|---|---|---|---|---|
| 22 | | chemdiv-119094 | 2144-0787 | -0.45 | 336. |
| 23 | | chemdiv-133064 | 2391-2374 | 2.45 | 395. |
| 24 | | chemdiv-159730 | 3284-1651 | 1.84 | 316. |
| 25 | | chemdiv-197874 | K089-0087 | 3.19 | 394. |

TABLE 12-continued

| | ligase 151 nanosyn006272 s85 | COMP NAME | IDNUMBER | logP | MW |
|---|---|---|---|---|---|
| 26 | | chemdiv-4107645 | C163-0462 | 0.11 | 291. |
| 27 | | chemdiv-4107646 | C163-0463 | 0.41 | 305. |
| 28 | | mdd022784 | st016688 | 3.25 | 409. |
| 29 | | nanosyn013594 | NS18706 | 3.40 | 472. |

TABLE 12-continued
| | ligase 151 nanosyn006272 s85 | COMP NAME | IDNUMBER | logP | MW |
|---|---|---|---|---|---|
| 30 | 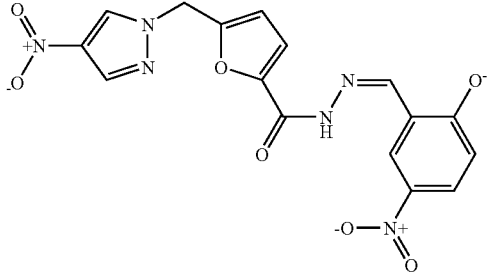 | specs0169427 | AK-968/15605425 | 1.77 | 399. |
| 31 | 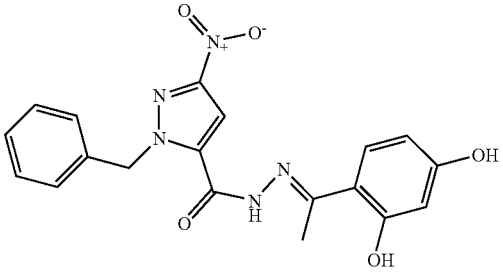 [SMILES: C/C(=N\NC(=O)c1cc([N+](=O)[O-])nn1Cc1ccccc1)c1ccc(O)cc1O] | specs0171739 | AK-968/40707401 | 3.14 | 395. |
| 32 | 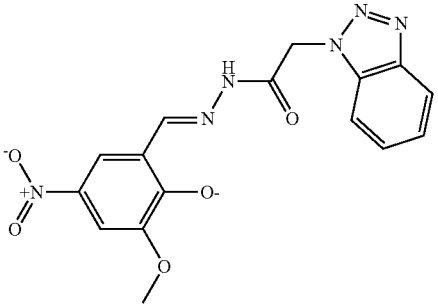 | specs4086774 | AK-968/11367247 | 2.26 | 369. |
| 33 | 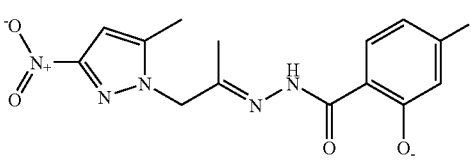 | specs4087434 | AK-968/11566598 | 1.72 | 331. |
| 34 | 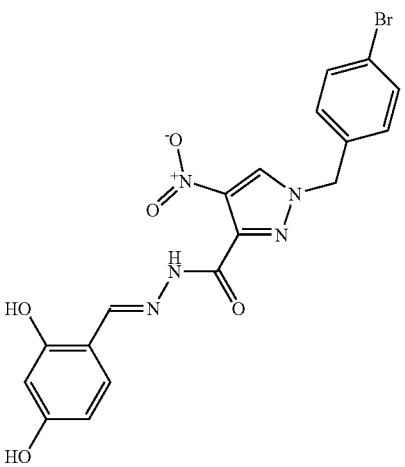 | timtt017652 | ST017652 | 3.57 | 460. |

TABLE 12-continued
| | ligase 151 nanosyn006272 s85 | COMP NAME | IDNUMBER | logP | MW |
|---|---|---|---|---|---|
| 35 | 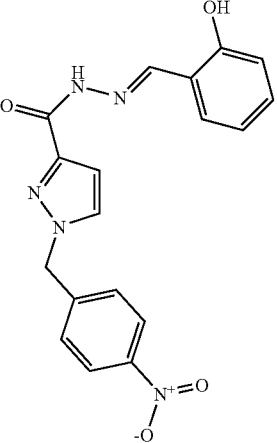 | timtt017715 | ST017715 | 3.04 | 365. |
| 36 | 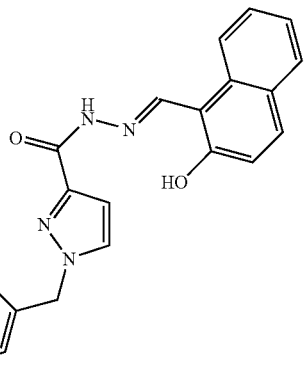 | timtt017987 | ST017987 | 4.26 | 415. |
| 37 | 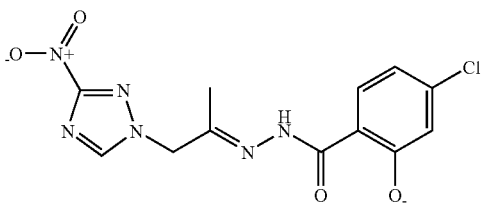 | timtt025827 | ST025827 | 1.05 | 337. |
| 38 | 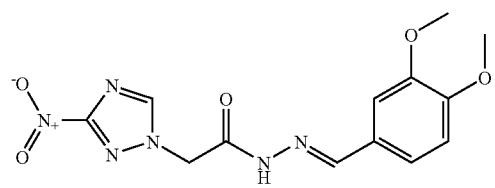 | timtt4016474 | ST4016474 | 0.39 | 334. |

TABLE 13

| | ligase 180 specs0112290 85% | COMP NAME | ID NUMBER | MW | loop | c... |
|---|---|---|---|---|---|---|
| 1 | | specs0112290 | AG-205/15425118 | 301. | 2.44 | 1.0 |
| 2 | | chemdiv0310191 | 8011-6630 | 362. | 4.41 | 25. |
| 3 | | chemdiv0310192 | 8011-6631 | 362. | 4.45 | 26. |
| 4 | | chemdiv0310201 | 8011-6652 | 300. | 2.80 | 85. |
| 5 | | chemdiv0310393 | 8011-7163 | 286. | 2.46 | 12. |
| 6 | | chemdiv0310717 | 8011-7952 | 270. | 2.80 | 9.0 |

TABLE 13-continued

| | ligase 180 specs0112290 85% | COMP NAME | ID NUMBER | MW | loop | c... |
|---|---|---|---|---|---|---|
| 7 | | chemdiv0310830 | 8011-8313 | 348. | 3.82 | 79. |
| 8 | | chemdiv0310998 | 8011-9000 | 362. | 4.25 | 10. |
| 9 | | chemdiv0311207 | 8011-9694 | 348. | 4.11 | 11. |
| 10 | | chemdiv0311221 | 8011-9716 | 378. | 4.07 | 12. |
| 11 | | chemdiv0311222 | 8011-9717 | 427. | 4.91 | 80. |

TABLE 13-continued

| ligase 180 specs0112290 85% | COMP NAME | ID NUMBER | MW | loop | c... |
|---|---|---|---|---|---|
| 12 | chemdiv0311440 | 8012-0207 | 405. | 3.40 | 13. |
| 13 | chemdiv0311639 | 8012-0573 | 378. | 4.11 | 12. |
| 14 | chemdiv0312704 | 8012-3473 | 405. | 3.44 | 13. |
| 15 | chemdiv0313234 | 8012-4572 | 378. | 3.82 | 81. |
| 16 | chemdiv0313235 | 8012-4573 | 427. | 4.91 | 82. |

TABLE 13-continued

| ligase 180 specs0112290 85% | COMP NAME | ID NUMBER | MW | loop | c... |
|---|---|---|---|---|---|
| 17 | chemdiv0314847 | 8012-7734 | 362. | 4.45 | 35. |
| 18 | chemdiv0314848 | 8012-7735 | 315. | 2.77 | 36. |
| 19 | chemdiv0315436 | 8012-8805 | 335. | 3.07 | 37. |
| 20 | chemdiv0315593 | 8012-9041 | 392. | 4.41 | 38. |
| 21 | chemdiv0315842 | 8012-9471 | 382. | 4.71 | 90. |
| 22 | chemdiv0315970 | 8012-9712 | 376. | 4.74 | 39. |

TABLE 13-continued

| | ligase 180 specs0112290 85% | COMP NAME | ID NUMBER | MW | loop | c... |
|---|---|---|---|---|---|---|
| 23 | | chemdiv166863 | 8004-3116 | 359. | 4.10 | 3.0 |
| 24 | | chemdiv167327 | 8004-6065 | 391. | 4.12 | 91. |
| 25 | | chemdiv4081327 | 8013-0295 | 382. | 4.70 | 92. |
| 26 | | chemdiv4081378 | 8013-0379 | 382. | 4.74 | 90. |
| 27 | | chemdiv4081817 | 8013-1129 | 382. | 4.74 | 90. |

TABLE 13-continued
| ligase 180 specs0112290 85% | | COMP NAME | ID NUMBER | MW | loop | c... |
|---|---|---|---|---|---|---|
| 28 | 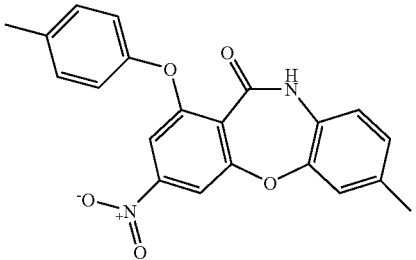 | chemdiv4082010 | 8013-1437 | 376. | 4.75 | 42. |
| 29 | 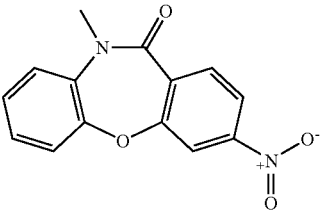 [SMILES: CN1C(=O)c2ccc([N+](=O)[O-])cc2Oc2ccccc21] | chemdiv4082586 | 8013-2547 | 270. | 2.67 | 95. |
| 30 | 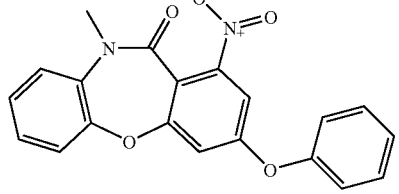 | chemdiv4082587 | 8013-2548 | 362. | 4.31 | 96. |
| 31 | 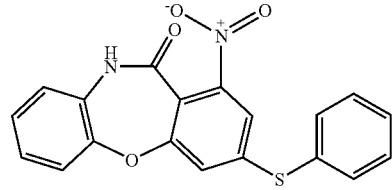 | chemdiv4082589 | 8013-2550 | 364. | 4.75 | 43. |
| 32 | 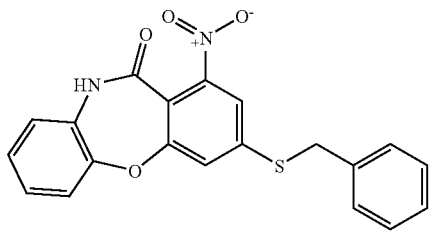 [SMILES: O=C1Nc2ccccc2Oc2cc(SCc3ccccc3)cc([N+](=O)[O-])c21] | chemdiv4082929 | 8013-3105 | 378. | 4.88 | 44. |
| 33 | 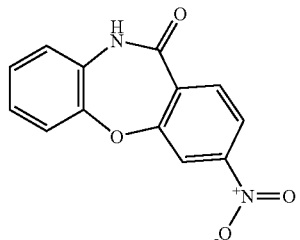 | chemdiv4085402 | 8014-2098 | 256. | 2.47 | 2.0 |
| 34 | 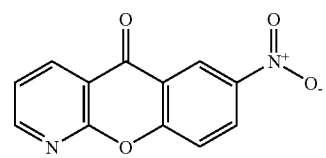 [SMILES: O=c1c2cc([N+](=O)[O-])ccc2oc2ncccc12] | maybridge0403444 | BTB = 04948 | 242. | 1.81 | 76. |

TABLE 13-continued

| | ligase 180 specs0112290 85% | COMP NAME | ID NUMBER | MW | loop | c... |
|---|---|---|---|---|---|---|
| 35 | | maybridge0403698 | BTB = 05308 | 361. | 2.76 | 5.0 |
| 36 | | specs0113723 | AG-205/33687036 | 393. | 4.73 | 77. |
| 37 | | specs0137866 | AG-690/36533026 | 419. | 3.92 | 21. |
| 38 | | specs4047979 | AG-690/11629040 | 270. | 2.77 | 24. |
| 39 | | timtt049828 | ST049828 | 362. | 4.41 | 60. |

TABLE 13-continued
| | ligase 180 specs0112290 85% | COMP NAME | ID NUMBER | MW | loop | c... |
|---|---|---|---|---|---|---|
| 40 | 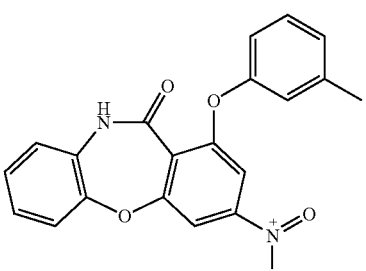 | timtt049829 | ST049829 | 362. | 4.45 | 61. |
| 41 | 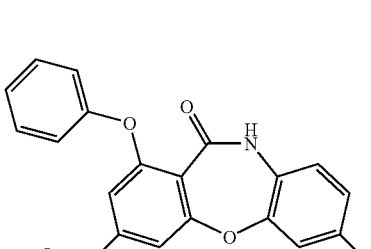 | timtt050161 | ST050161 | 362. | 4.45 | 68. |
TABLE 14
| | mol | COMP_NAME | ID NUMBER | MW | logP |
|---|---|---|---|---|---|
| 1 | 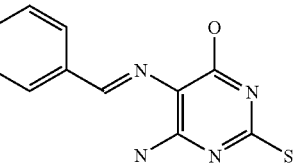 | specs4002175 | AC-907/34129012 | 246.29 | 1.84 |
| 2 | 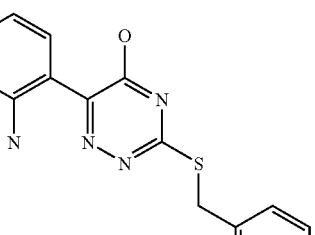 | chembridge0120016 | 6636907 | 310.38 | 4.05 |
| 3 |  | chembridge0245406 | 5808234 | 233.29 | 2.14 |

TABLE 14-continued

| | mol | COMP_NAME | ID NUMBER | MW | logP |
|---|---|---|---|---|---|
| 4 | | chembridge0273454 | 6955471 | 275.38 | 3.11 |
| 5 | | chembridge0277001 | 6988183 | 297.38 | 3.66 |
| 6 | | chembridge0401734 | 7934912 | 258.3 | 1.8 |
| 7 | | chembridge096171 | 5940801 | 302.18 | 3.36 |
| 8 | | chemdiv0281324 | 4065-0116 | 233.29 | 2.14 |
| 9 | | chemdiv178113 | 8008-5795 | 281.77 | 3.37 |
| 10 | | maybridge0415961 | GK = 03672 | 302.18 | 3.32 |

TABLE 14-continued
| | mol | COMP_NAME | ID NUMBER | MW | logP |
|---|---|---|---|---|---|
| 11 | 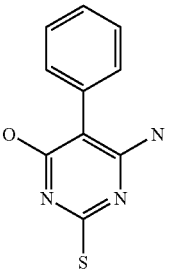 [SMILES: Nc1nc(S)nc(O)c1-c1ccccc1] | maybridge0438482 | RDR = 01717 | 219.27 | 2.17 |
| 12 | 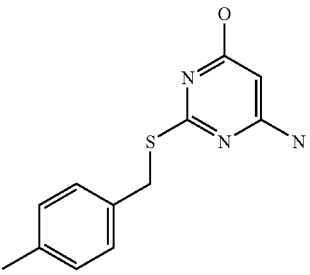 [SMILES: Cc1ccc(CSc2nc(N)cc(O)n2)cc1] | specs0142965 | AG-690/40701022 | 247.32 | 2.44 |
| 13 | 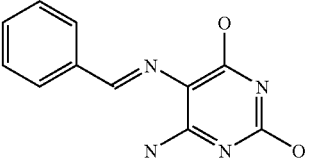 [SMILES: Nc1nc(O)nc(O)c1/N=C/c1ccccc1] | specs4001624 | AB-323/13887140 | 230.23 | 1.05 |
| 14 | 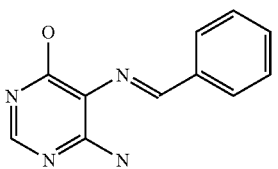 [SMILES: Nc1ncnc(O)c1/N=C/c1ccccc1] | specs4002174 | AC-907/34129010 | 214.23 | 0.988 |
| 15 | 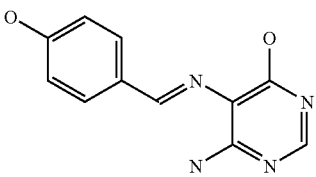 [SMILES: Nc1ncnc(O)c1/N=C/c1ccc(O)cc1] | specs4002176 | AC-907/34129013 | 230.23 | 0.68 |
| 16 | 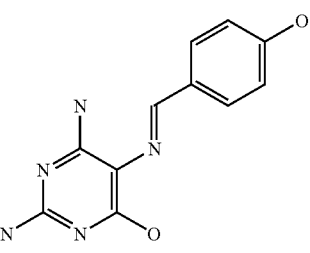 [SMILES: Nc1nc(N)c(/N=C/c2ccc(O)cc2)c(O)n1] | specs4018988 | AG-205/07664054 | 245.24 | 0.375 |

TABLE 14-continued
| | mol | COMP_NAME | ID NUMBER | MW | logP |
|---|---|---|---|---|---|
| 17 | 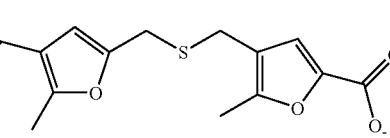 | specs4037037 | AG-205/41280558 | 297.38 | 3.66 |
| 18 | 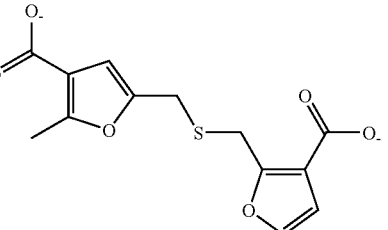 | specs4064355 | AG-690/40700626 | 258.3 | 1.8 |
TABLE 15
| | ligase_197_specs4028351_similar80 | COMP_NAME | ID NUMBER | MW | logP | clus |
|---|---|---|---|---|---|---|
| 1 | 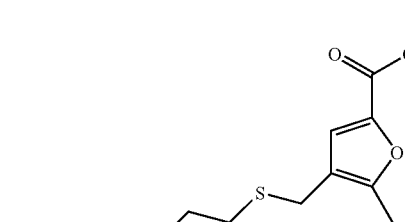 | 197_specs4028351 | AG-205/32243059 | 308 | 1.87 | 1 |
| 2 | | amb_a005908 | 5908 | 308 | 1.87 | 17 |
| 3 | | amb_a0034227 | 34248 | 368 | 2.42 | 23 |

TABLE 15-continued

| ligase_197_specs4028351_similar80 | COMP_NAME | ID NUMBER | MW | logP | clus |
|---|---|---|---|---|---|
| 4 | amb_a0041542 | 6653 | 308 | 1.87 | 26 |
| 5 | amb_b0092949 | 844 | 321 | 2.18 | 2 |
| 6 | amb_c0086983 | BAS = 1172053 | 368 | 2.42 | 29 |
| 7 | amb_c0104748 | A2485/0105630 | 307 | 1.85 | 3 |
| 8 | amb_c0112456 | 3380 | 321 | 2.18 | 2 |

TABLE 15-continued

| ligase_197_specs4028351_similar80 | COMP_NAME | ID NUMBER | MW | logP | clus |
|---|---|---|---|---|---|
| 9 | amb_d002779 | BAS = 1172053 | 368 | 2.42 | 29 |
| 10 | amb_d030490 | A2485/0105630 | 307 | 1.85 | 3 |
| 11 | amb_e0047907 | 6653 | 308 | 1.87 | 26 |
| 12 | chembridge0153135 | 5928213 | 308 | 1.87 | 26 |
| 13 | chembridge0153147 | 5928363 | 294 | 1.66 | 32 |

TABLE 15-continued

| | ligase__197__specs4028351__similar80 | COMP_NAME | ID NUMBER | MW | logP | clus |
|---|---|---|---|---|---|---|
| 14 | (structure) | chembridge0165304 | 6057299 | 370 | 3.53 | 33 |
| 15 | (structure) | chembridge0165868 | 6062534 | 368 | 2.42 | 23 |
| 16 | (structure) | chembridge0211898 | 6534037 | 280 | 1.44 | 34 |
| 17 | (structure) | chembridge0255068 | 6423354 | 307 | 1.85 | 3 |
| 18 | (structure) | chembridge0256700 | 6515124 | 308 | 1.87 | 1 |
| 19 | (structure) | chembridge0257432 | 6558640 | 308 | 1.87 | 17 |

TABLE 15-continued
| ligase_197_specs4028351_similar80 | | COMP_NAME | ID NUMBER | MW | logP | clus |
|---|---|---|---|---|---|---|
| 20 | 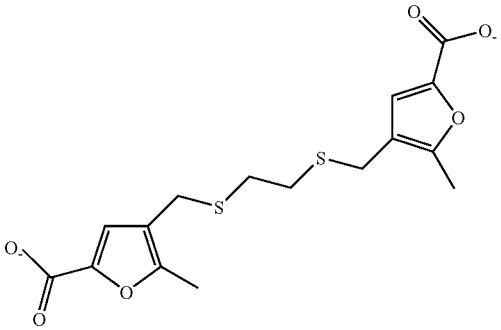 [SMILES: Cc1oc(C(=O)[O-])cc1CSCCSCc1cc(C(=O)[O-])oc1C] | chemdiv030171 | 8002-7527 | 368 | 2.42 | 23 |
| 21 | 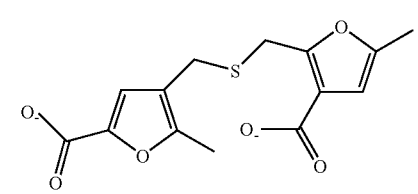 [SMILES: Cc1cc(C(=O)[O-])c(CSCc2cc(C(=O)[O-])oc2C)o1] | chemdiv033499 | 8003-7465 | 308 | 1.87 | 1 |
| 22 | 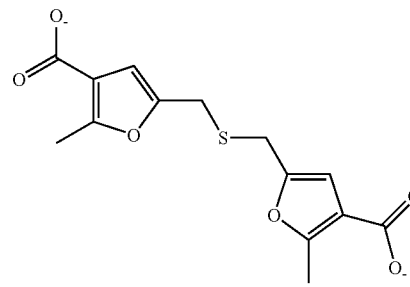 | chemdiv033518 | 8003-7503 | 308 | 1.87 | 17 |
| 23 | 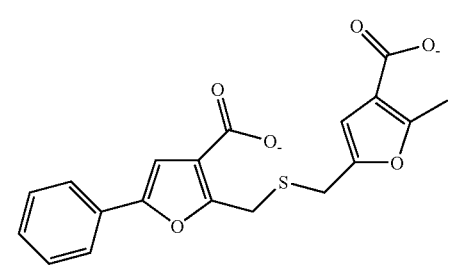 [SMILES: Cc1oc(CSCc2oc(-c3ccccc3)cc2C(=O)[O-])cc1C(=O)[O-]] | chemdiv037027 | 8004-7581 | 370 | 3.53 | 35 |
| 24 | 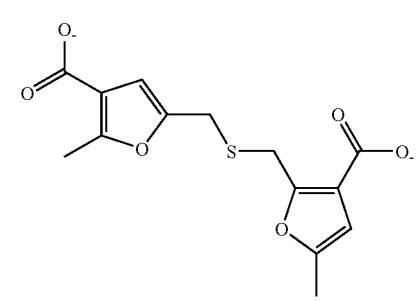 [SMILES: Cc1cc(C(=O)[O-])c(CSCc2cc(C(=O)[O-])c(C)o2)o1] | chemdiv042175 | 8005-9535 | 308 | 1.87 | 17 |
| 25 | 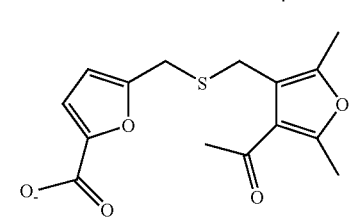 | chemdiv4080846 | 8011-5630 | 307 | 1.85 | 3 |

TABLE 15-continued

| ligase_197_specs4028351_similar80 | COMP_NAME | ID NUMBER | MW | logP | clus |
|---|---|---|---|---|---|
| 26 | specs4027891 | AG-205/14552050 | 307 | 1.85 | 3 |
| 27 | timtt045056 | ST045056 | 307 | 1.85 | 3 |
| 28 | timtt057325 | ST057325 | 308 | 1.87 | 1 |
| 29 | timtt057327 | ST057327 | 308 | 1.87 | 17 |
| 30 | timtt204715 | ST204715 | 308 | 1.87 | 17 |
| 31 | timtt207481 | ST207481 | 368 | 2.42 | 29 |

1. Ding, J., Miao, Z. H., Meng, L. H., and Geng, M. Y. (2006) *Trends Pharmacol Sci* 27(6), 338-344
2. Madhusudan, S., and Hickson, I. D. (2005) *Trends Mol Med* 11(11), 503-511
3. Madhusudan, S., and Middleton, M. R. (2005) *Cancer Treat Rev* 31(8), 603-617
4. Bryant, H. E., Schultz, N., Thomas, H. D., Parker, K. M., Flower, D., Lopez, E., Kyle, S., Meuth, M., Curtin, N. J., and Helleday, T. (2005) *Nature* 434(7035), 913-917
5. Farmer, H., McCabe, N., Lord, C. J., Tutt, A. N., Johnson, D. A., Richardson, T. B., Santarosa, M., Dillon, K. J., Hickson, I., Knights, C., Martin, N. M., Jackson, S. P., Smith, G. C., and Ashworth, A. (2005) *Nature* 434(7035), 917-921
6. Tomkinson, A. E., Vijayakumar, S., Pascal, J. M., and Ellenberger, T. (2006) *Chem Rev* 106(2), 687-699
7. Barnes, D. E., Tomkinson, A. E., Lehmann, A. R., Webster, A. D., and Lindahl, T. (1992) *Cell* 69(3), 495-503
8. Lehmann, A. R., Willis, A. E., Broughton, B. C., James, M. R., Steingrimsdottir, H., Harcourt, S. A., Arlett, C. F., and Lindahl, T. (1988) *Cancer Res* 48(22), 6343-6347
9. Teo, I. A., Broughton, B. C., Day, R. S., James, M. R., Karran, P., Mayne, L. V., and Lehmann, A. R. (1983) *Carcinogenesis* 4(5), 559-564
10. Sun, D., Urrabaz, R., Nguyen, M., Marty, J., Stringer, S., Cruz, E., Medina-Gundrum, L., and Weitman, S. (2001) *Clin Cancer Res* 7(12), 4143-4148
11. Caldecott, K. W., McKeown, C. K., Tucker, J. D., Ljungquist, S., and Thompson, L. H. (1994) *Mol Cell Biol* 14(1), 68-76
12. Caldecott, K. W., Tucker, J. D., Stanker, L. H., and Thompson, L. H. (1995) *Nucleic Acids Res* 23(23), 4836-4843
13. Lakshmipathy, U., and Campbell, C. (1999) *Mol Cell Biol* 19(5), 3869-3876
14. Lakshmipathy, U., and Campbell, C. (2001) *Nucleic Acids Res* 29(3), 668-676
15. Frosina, G., Fortini, P., Rossi, O., Carrozzino, F., Raspaglio, G., Cox, L. S., Lane, D. P., Abbondandolo, A., and Dogliotti, E. (1996) *J Biol Chem* 271(16), 9573-9578
16. Levin, D. S., McKenna, A. E., Motycka, T. A., Matsumoto, Y., and Tomkinson, A. E. (2000) *Curr Biol* 10(15), 919-922
17. Adachi, N., Ishino, T., Ishii, Y., Takeda, S., and Koyama, H. (2001) *Proc Natl Acad Sci USA* 98(21), 12109-12113
18. Pascal, J. M., O'Brien, P. J., Tomkinson, A. E., and Ellenberger, T. (2004) *Nature* 432(7016), 473-478
19. Sun, D., and Urrabaz, R. (2004) *J Biochem Biophys Methods* 59(1), 49-59
20. Tan, G. T., Lee, S., Lee, I. S., Chen, J., Leitner, P., Besterman, J. M., Kinghorn, A. D., and Pezzuto, J. M. (1996) *Biochem J* 314 (Pt 3), 993-1000
21. Hancock, C. N., Macias, A., Lee, E. K., Yu, S. Y., Mackerell, A. D., Jr., and Shapiro, P. (2005) *J Med Chem* 48(14), 4586-4595
22. Chen, X., Pascal, J., Vijayakumar, S., Wilson, G. M., Ellenberger, T., and Tomkinson, A. E. (2006) *Methods Enzymol* 409, 39-52
23. Gallmeier, E., Hucl, T., Brody, J. R., Dezentje, D. A., Tahir, K., Kasparkova, J., Brabec, V., Bachman, K. E., and Kern, S. E. (2007) *Cancer Res* 67(5), 2169-2177
24. Chen, L., Trujillo, K., Sung, P., and Tomkinson, A. E. (2000) *J Biol Chem* 275(34), 26196-26205
25. Ahel, I., Rass, U., El-Khamisy, S. F., Katyal, S., Clements, P. M., McKinnon, P. J., Caldecott, K. W., and West, S. C. (2006) *Nature* 443(7112), 713-716
26. Tomkinson, A. E., Tappe, N. J., and Friedberg, E. C. (1992) *Biochemistry* 31(47), 11762-11771
27. Baumann, P., and West, S. C. (1998) *Proc Natl Acad Sci USA* 95(24), 14066-14070
28. Zheng, L., Dai, H., Qiu, J., Huang, Q., and Shen, B. (2007) *Mol Cell Biol* 27(8), 3176-3186
29. Mackey, Z. B.; Niedergang, C.; Murcia, J. M.; Leppard, J.; Au, K.; Chen, J.; de Murcia, G.; Tomkinson, A. E., DNA ligase III is recruited to DNA strand breaks by a zinc finger motif homologous to that of poly(ADP-ribose) polymerase. Identification of two functionally distinct DNA binding regions within DNA ligase III. *J. Biol. Chem.* 1999, 274, (31), 21679-87.
30. Srivastava, S. K.; Dube, D.; Tewari, N.; Dwivedi, N.; Tripathi, R. P.; Ramachandran, R., Mycobacterium tuberculosis NAD+-dependent DNA ligase is selectively inhibited by glycosylamines compared with human DNA ligase I. *Nucleic Acids Res.* 2005, 33, (22), 7090-101.
31. Wang W, Bambara R A. Human Bloom protein stimulates flap endonuclease 1 activity by resolving DNA secondary structure. *J Biol Chem* 2005; 280:5391-9.
32. Di Virgilio M, Gautier J. Repair of double-strand breaks by non-homologous end joining in the absence of Mre11. J Cell Biol 2005; 171:765-71.
33. Chen L, Trujillo K, Ramos W, Sung P, Tomkinson A E. Promotion of Dnl4-catalyzed DNA end-joining by the Rad50/Mre11/Xrs2 and Hdf1/Hdf2 complexes. Mol Cell 2001; 8:1105-15.
34. Ewing T J, Makino S, Skillman A G, Kuntz I D. DOCK 4.0: search strategies for automated molecular docking of flexible molecule databases. J Comput Aided Mol Des 2001; 15:411-28.
35. Huang N, Nagarsekar A, Xia G, Hayashi J, MacKerell A D, Jr. Identification of non-phosphate-containing small molecular weight inhibitors of the tyrosine kinase p56 Lck SH2 domain via in silico screening against the pY+3 binding site. J Med Chem 2004; 47:3502-11.
36. Kuntz I D, Blaney J M, Oatley S J, Langridge R, Ferrin T E. A geometric approach to macromolecule-ligand interactions. J Mol Biol 1982; 161:269-88.
37. Markowitz J, Chen I, Gitti R, et al. Identification and characterization of small molecule inhibitors of the calcium-dependent S100B-p53 tumor suppressor interaction. J Med Chem 2004; 47:5085-93.
38. Berman, H. M.; Westbrook, J.; Feng, Z.; Gilliland, G.; Bhat, T. N.; Weissig, H.; Shindyalov, I. N.; Bourne, P. E., The Protein Data Bank. Nucleic Acids Res. 2000, 28, (1), 235-42.
39. Brooks, B. R.; Bruccoleri, R. E.; Olafson, B. D.; States, D. J.; Swaminathan, S.; Karplus, M., CHARMM: A program for macromolecular energy, minimization, and dynamics calculations. J. Comput. Chem. 1983, 4, (2), 187-217.
40. MacKerell, A. D., Jr.; Bashford, D.; Bellott, M.; Dunbrack, R. L.; Evanseck, J. D.; Field, M. J.; Fischer, S.; Gao, J.; Guo, H.; Ha, S.; Joseph-McCarthy, D.; Kuchnir, L.; Kuczera, K.; Lau, F. T. K.; Mattos, C.; Michnick, S.; Ngo, T.; Nguyen, D. T.; Prodhom, B.; Reiher, W. E.; Roux, B.; Schlenkrich, M.; Smith, J. C.; Stote, R.; Straub, J.; Watanabe, M.; Wiorkiewicz-Kuczera, J.; Yin, D.; Karplus, M., All-atom empirical potential for molecular modeling and dynamics studies of proteins. J. Phys. Chem. B 1998, 102, (18), 3586-3616.
41. Mackerell, A. D., Jr., Empirical force fields for biological macromolecules: overview and issues. J. Comput. Chem. 2004, 25, (13), 1584-604.

42. Brooks, C. L., III; Karplus, M., Deformable Stochastic Boundaries in Molecular Dynamics. J. Chem. Phys. 1983, 79, (12), 6312-6325.
43. Snyman, J. A., *Practical Mathematical Optimization: An Introduction to Basic Optimization Theory and Classical and New Gradient-Based Algorithms*. Springer-Verlag: New York, 2005; p 257.
44. Beglov, D.; Roux, B., Dominant Salvation Effects from the Primary Shell of Hydration—Approximation for Molecular-Dynamics Simulations. Biopolymers 1995, 35, (2), 171-178.
45. Beglov, D.; Roux, B., Finite Representation of an Infinite Bulk System—Solvent Boundary Potential for Computer-Simulations. J. Chem. Phys. 1994, 100, (12), 9050-9063.
46. Steinbach, P. J.; Brooks, B. R., New Spherical-Cutoff Methods of Long-Range Forces in Macromolecular Simulations. J. Comp. Chem. 1994, 15, 667-683.
47. Swope, W. C.; Andersen, H. C.; Berens, P. H.; Wilson, K. R., A computer simulation method for the calculation of equilibrium constants for the formation of physical clusters of molecules: Application to small water clusters. J. Chem. Phys. 1982, 76, (1), 637-649.
48. Ryckaert, J. P.; Ciccotti, G.; Berendsen, H. J. C., Numerical Integration of the Cartesian Equations of Motion of a System with Constraints: Molecular Dynamics of n-alkanes. J. Comp. Phys. 1977, 23, 327-341.
49. Kelley, L. A.; Gardner, S. P.; Sutcliffe, M. J., An automated approach for clustering an ensemble of NMR-derived protein structures into conformationally related subfamilies. Protein Eng. 1996, 9, (11), 1063-5.
50. Connolly, M., Analytical molecular surface calculation. J. Appl. Cryst. 1983, 16, 548-558.
51. Connolly, M. L., Solvent-accessible surfaces of proteins and nucleic acids. Science 1983, 221, (4612), 709-13.
52. Ferrin, T. E.; Huang, C. C.; Jarvis, L. E.; Langridge, R., The MIDAS display system. J. Mol. Graphics 1988, 6, 13-27.
53. Pettersen, E. F.; Goddard, T. D.; Huang, C. C.; Couch, G. S.; Greenblatt, D. M.; Meng, E. C.; Ferrin, T. E., UCSF Chimera—a visualization system for exploratory research and analysis. J. Comput. Chem. 2004, 25, (13), 1605-12.
54. Halgren, T. A., MMFF VI. MMFF94s option for energy minimization studies. J. Comp. Chem. 1999, 20, (7), 720-729.
55. Halgren, T. A., MMFF VII. Characterization of MMFF94, MMFF94s, and other widely available force fields for conformational energies and for intermolecular-interaction energies and geometries. J. Comp. Chem. 1999, 20, (7), 730-748.
56. Chambers, C. C.; Hawkins, G. D.; Cramer, C. J.; Truhlar, D. G., Model for aqueous solvation based on class IV atomic charges and first solvation shell effects. J. Phys. Chem. 1996, 100, 16385-16398.
57. Li, J.; Zhu, T.; Cramer, C. J.; Truhlar, D. G., New class IV charges model for extracting accurate partial charges from wave functions. J. Phys. Chem. A 1998, 102, 1820-1831.
58. Sirois, S.; Hatzakis, G.; Wei, D.; Du, Q.; Chou, K.-C., Assessment of chemical libraries for their druggability. Comp. Biol. Chem. 2005, 29, 55-67.
59. Hancock, C. N.; Macias, A.; Lee, E. K.; Yu, S. Y.; MacKerell, A. D., Jr.; Shapiro, P., Identification of novel extracellular signal-regulated kinase docking domain inhibitors. J. Med. Chem. 2005, 48, (14), 4586-4595.
60. Huang, N.; Nagarsekar, A.; Xia, G.; Hayashi, J.; MacKerell, A. D., Jr., Identification of non-phosphate-containing small molecular weight inhibitors of the tyrosine kinase p56 Lck SH2 domain via in silico screening against the pY+3 binding site. J. Med. Chem. 2004, 47, (14), 3502-11.
61. Leach, A. R.; Kuntz, I. D., Conformational analysis of flexible ligands in macromolecular receptor sites. J. Comput. Chem. 1992, 13, 730-748.
62. Tanimoto, T., *IBM Internal Report, November* 1957.
63. Godden, J. W.; Xue, L.; Bajorath, J., Combinatorial preferences affect molecular similarity/diversity calculations using binary fingerprints and Tanimoto coefficients. J. Chem. Inf. Comput. Sci. 2000, 40, (1), 163-6.
64. Durant, J. L.; Leland, B. A.; Henry, D. R.; Nourse, J. G., Reoptimization of MDL keys for use in drug discovery. J. Chem. Inf. Comput. Sci. 2002, 42, (6), 1273-80.
65. Willett, P.; Barnard, J. M.; Downs, G. M., Chemical similarity searching. J. Chem. Inf. Comput. Sci. 1998, 38, (6), 983-996.
66. Pan, Y.; Huang, N.; Cho, S.; MacKerell, A. D., Jr., Consideration of Molecular Weight During Compound Selection in Virtual Target-Based Database Screening. J. Chem. Inf. Comp. Sci. 2003, 43, 267-272.
67. Carlson, H. A., Protein flexibility and drug design: how to hit a moving target. Curr. Opin. Chem. Biol. 2002, 6, 447-452.
68. Carlson, H. A.; McCammon, J. A., Accommodating Protein Flexibility in Computational Drug Design. Mol. Pharmacol. 2000, 57, 213-218.
69. Oprea, T. I.; Davis, A. M.; Teague, S. J.; Leeson, P. D., Is There a Difference between Leads and Drugs? A Historical Perspective. J. Chem. Inf. Comput. Sci. 2001, 41, 1308-1315.
70. Lipinski, C. A., Drug-like properties and the causes of poor solubility and poor permeability. J. Pharmacol. Toxicol. Methods 2000, 44, 235-249.
71. Lipinski, C. A.; Lombardo, F.; Dominy, B. W.; Feeney, P. J., Experimental and computational approaches to estimate solubility and permeability in drug discovery and development settings. Adv. Drug Deliv. Rev. 2001, 46, (1-3), 3-26.
72. Brown, R. D.; Martin, Y. C., An evaluation of structural descriptors and clustering methods for use in diversity selection. SAR QSAR Environ. Res. 1998, 8, (1-2), 23-39.
73. Chen, X.; Zhong, S.; Zhu, X.; Dziegielewska, B.; Ellenberger, E.; Wilson, G. M.; MacKerell, A. D., Jr.; Tomkinson, A. E., Rational Design of Human DNA Ligase Inhibitors that Target Cellular DNA Replication and Repair. Cancer Res. (Submitted, December 2007).

All of the cited references are hereby specifically incorporated by reference in their entirety.

While the invention has been described with reference to certain particular embodiments thereof, the invention is not to be limited to the specific embodiments described and those skilled in the art will appreciate that various modifications may be made without departing from the spirit and scope of the invention.

TABLE 3

192 Compounds Tested
List of 192 compounds that have been assayed

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| 21 | 22 | 23 | 24 | 25 | 26 | 27 | 28 | 29 | 30 | 32 | 33 | 34 | 35 | 36 | 37 | 38 | 39 | 40 | 41 |

TABLE 3-continued

192 Compounds Tested
List of 192 compounds that have been assayed

| | | | | | | | | | | | | | | | | | | | |
|---|---|---|---|---|---|---|---|---|---|---|---|---|---|---|---|---|---|---|---|
| 42 | 43 | 45 | 46 | 47 | 48 | 49 | 51 | 53 | 54 | 55 | 56 | 57 | 58 | 59 | 60 | 61 | 62 | 63 | 64 |
| 65 | 66 | 67 | 68 | 69 | 70 | 71 | 72 | 73 | 75 | 76 | 77 | 78 | 79 | 80 | 81 | 82 | 83 | 84 | 85 |
| 86 | 88 | 89 | 90 | 92 | 93 | 94 | 95 | 96 | 97 | 99 | 100 | 101 | 102 | 103 | 104 | 105 | 106 | 107 | 108 |
| 109 | 111 | 112 | 113 | 114 | 115 | 116 | 117 | 118 | 119 | 120 | 121 | 122 | 123 | 124 | 125 | 126 | 127 | 128 | 129 |
| 130 | 132 | 135 | 136 | 137 | 138 | 139 | 140 | 141 | 142 | 143 | 150 | 151 | 153 | 159 | 161 | 162 | 165 | 16 | |
| 170 | 172 | 173 | 175 | 176 | 177 | 178 | 179 | 180 | 181 | 182 | 183 | 184 | 185 | 186 | 188 | 189 | 190 | 191 | 192 |
| 193 | 194 | 195 | 196 | 197 | 198 | 199 | 200 | 201 | 202 | 203 | 204 | 205 | 206 | 207 | 208 | 209 | 210 | 211 | 212 |
| 213 | 214 | 215 | 216 | 217 | 218 | 219 | 220 | 221 | 222 | 223 | 234 | | | | | | | | |

TABLE 4

Molecular properties of the 15 active compounds, their experimental inhibition rate targeting Lig1 and the growth inhibition.

| Cmpd | Rot | Ring | MW | Ha | Hd | LogP | hLig1_Inh % (100 μM) | Growth_Inh % (50 μM) MCF10A | HCT116 |
|---|---|---|---|---|---|---|---|---|---|
| 25 | 1 | 2 | 190.13 | 2 | 1 | 0.24 | 59.3 ± 7.5 | | |
| 32* | 6 | 3 | 385.38 | 6 | 1 | 2.10 | 83.4 ± 3.1 | | |
| 64 | 4 | 2 | 288.65 | 2 | 0 | 2.15 | 60.6 ± 0.54 | 40 | |
| 67 | 6 | 2 | 485.11 | 2 | 2 | 4.91 | 78.3 ± 8.5 | 70 | 70 |
| 82 | 4 | 2 | 308.66 | 3 | 2 | 4.84 | 59.8 ± 1.7 | 70 | 40 |
| 113 | 8 | 2 | 475.38 | 5 | 2 | 1.42 | 53.4 ± 7.6 | | |
| 123 | 4 | 1 | 228.32 | 4 | 0 | 1.51 | 66.9 ± 3.5 | | |
| 175* | 1 | 2 | 173.15 | 2 | 0 | 1.12 | 54.2 * 16.5 | | |
| 180* | 2 | 3 | 301.21 | 2 | 1 | 2.44 | 58.3 * 6.0 | 70 | 70 |
| 189 | 2 | 2 | 244.28 | 3 | 1 | 1.96 | 68.8 ± 4.9 | 70 | 70 |
| 190 | 2 | 3 | 268.23 | 5 | 0 | 1.78 | 52.5 * 6.6 | 70 | 40 |
| 192* | 2 | 3 | 274.28 | 2 | 1 | 1.56 | 68.2 * 1.5 | | 70 |
| 197 | 6 | 2 | 308.31 | 0 | 0 | 1.87 | 91.0 * 6.9 | | |
| 200 | 2 | 2 | 212.2 | 1 | 0 | 3.04 | 50.7 * 10.9 | | |
| 202* | 4 | 4 | 390.42 | 1 | 0 | 5.08 | 95.0 * 6.0 | 50 | |

*= compounds are those that also inhibit T4 DNA ligase by >50%
Rot is the number of rotatable bonds,
Ring is the number of rings,
MW is the molecular weight;
Ha is the number of H-bond acceptors,
Hd is the number of H-bond donors,
LogP is the octanol/water partition coefficient.
DNA joining and cell culture assays were performed as described.
Inhibition of joining and proliferartion is expressed as a percentage of values obtained with DMSO alone.

TABLE 5

| | % activity Inhibition | | | | | | | | % growth inhibition | |
|---|---|---|---|---|---|---|---|---|---|---|
| | hLigI | | hLigIII | | hLigIV | | LigT4 | MCF10A | HCT116 | MCF10A | HCT116 |
| Drug # | 100 uM | gel | 100 uM | gel | 100 uM | gel | 100 uM | 50 uM [2 Gy] | | 5-15 uM | |
| A# Drug that inhibit human DNA Ligases but not T4 DNA ligase or more than T4 | | | | | | | | | | | |
| A1# Common inhibitors for hLig1, hLigIII, and hLigIV | | | | | | | | | | | |
| 64 | 60.6 ± 0.54 | 50 | 48.5 ± 0.1 | +++ | 51.9 ± 1.2 | 66 | 18.4 ± 8.4 | 40 | 70 | | |
| 189 | 68.8 ± 4.9 | 75 | 52.6 ± 4.8 | ++ | >50 | 80 | 3.2 ± 1.9 | 70 | 70 | | |
| 197 | 91.0 ± 6.9 | 98 | 96.5 ± 3.5 | +++ | >60 | 100 | 24.4 ± 5.8 | | | | |
| A2# Common inhibitors for hLig1 and hLigIII | | | | | | | | | | | |
| 67 | 78.3 ± 8.5 | 73 | 88.2 ± 11.6 | ++ | Ø | | 0 ± 10.5 | 70 | 70 | ✓ | |
| 200 | 50.7 ± 10.9 | 53 | 59.5 ± 5.2 | ++ | Ø | | 0 | 70 | 70 | | ✓ |
| 82 | 59.8 ± 1.7 | 76 | 29.24 ± 7.30 | + | Ø | | 13.9 ± 11.4 | 70 | 40 | | |
| 25 | 59.3 ± 7.5 | +++ | 72.8 ± 4.8 | ++ | Ø | | 12.9 ± 6.3 | | | | |
| 213 | 36.4 ± 8.6 | + | 25.2 ± 0.46 | ± | Ø | | | 70 | 70 | | |
| 207 | 20.7 ± 19.0 | + | 25.8 ± 10.7 | ± | Ø | | 10.0 ± 2.0 | | | | |
| A3# Common inhibitors for hLig1 and hLigIV | | | | | | | | | | | |
| 113 | 53.4 ± 7.6 | +++ | Ø | | Ø | | >50 | 83 | 5.4 ± 4.5 | | |

TABLE 5-continued

| | % activity Inhibition | | | | | | | % growth inhibition | | |
|---|---|---|---|---|---|---|---|---|---|---|
| | hLigI | | hLigIII | | hLigIV | | LigT4 | MCF10A | HCT116 | MCF10A | HCT116 |
| Drug # | 100 uM | gel | 100 uM | gel | 100 uM | gel | 100 uM | 50 uM [2 Gy] | | 5-15 uM | |
| A4# Inhibitors unique to hLig1 | | | | | | | | | | | |
| 184 | 37.7 ± 12.4 | ND | Ø | | Ø | | 0.42 ± 1.4 | 70 | 40 | | ✓ |
| 190 | 52.5 ± 6.6 | +++ | Ø | | Ø | | 5.4 ± 0.74 | 40 | 40 | | |
| 1 | 40.3 ± 8.6 | +++ | Ø | | Ø | | 0 ± 3.8 | | | | |
| 43 | 29.2 ± 3.5 | + | Ø | | Ø | | 0 | 70 | 70 | | |
| 151 | 25.9 ± 1.2 | + | Ø | | Ø | | | 70 | 70 | ✓ | ✓ |
| 35 | 38.7 | + | Ø | ND | Ø | | 3.7 ± 2.3 | | | | |
| 37 | 25.2 ± 14.1 | + | Ø | ND | Ø | | 3.7 ± 0 | | | | |
| 47 | 24.2 ± 4.3 | + | Ø | ND | Ø | | 2.2 ± 0.7 | | | | |
| 51 | 24.3 ± 13.5 | + | Ø | ND | Ø | | 0 ± 2.6 | | | | |
| 53 | 36.4 ± 4.7 | + | Ø | ND | Ø | | 3.7 ± 4.8 | | | | |
| 54 | 32.2 ± 10.5 | + | Ø | ND | Ø | | 6.9 ± 0.45 | | | | |
| 55 | 7.5 ± 9.3 | + | Ø | ND | Ø | | 0.58 ± 3.1 | | | | |
| 90 | 20.7 ± 4.8 | + | Ø | ND | Ø | | 1.6 ± 3.1 | | | | |
| 103 | 23.1 ± 1.8 | + | Ø | ND | Ø | | 6.2 ± 4.3 | | | | |
| 193 | 28.2 ± 34.4 | + | Ø | ND | Ø | | 0.44 ± 2.1 | | | | |
| A5# Inhibitors unique to hLigIII | | | | | | | | | | | |
| 209 | Ø | ND | 70.5 ± 2.6 | ++ | Ø | | | | | | |
| 46 | Ø | ND | 21.57 ± 8.56 | + | Ø | | | | | | |
| A6# Inhibitors unique to hLigIV | | | | | | | | | | | |
| 215 | Ø | ND | Ø | ND | 60.7 ± 1.3 | 53 | Ø | | | | |
| 93 | Ø | ND | Ø | ND | 37.6 ± 6.1 | Ø | Ø | | | | |
| 122 | Ø | ND | Ø | ND | 16.1 ± 19.1 | 50 | Ø | | | | |

TABLE 5A

In Vitro and In Vivo properties of identified human DNA ligase inhibitors.

| | In vitro | | | | | | In vivo | | |
|---|---|---|---|---|---|---|---|---|---|
| | % inhib | | | | | | growth Inhb | | |
| | hLigI | hLigIII | hLigIV | T4 | | Cell Extract | MCF10A | HCT116 | cell survival |
| Cmpd | | 100 (μM) | | | Mechanism | 100 (μM) | % Inhb at 50 (μM) | | EC50 (μM) |
| Inhibit I, III, IV | | | | | | | | | |
| 64 | 61 ± 1 | 49 ± 1 | 52 ± 1 | 18 ± 8 | 1st step | | 40 | | IR sensitive, EC50~50 |
| 189 | 69 ± 5 | 53 ± 5 | 41 ± 6 | 3 ± 2 | 2nd, 3rd step | BER/NHEJ | 70 | 70 | IR sensitive, EC50~50 |
| 197 | 91 ± 7 | 96 ± 4 | 57 ± 3 | 24 ± 6 | 3rd step | | | | no activity |
| Inhibit I, III | | | | | | | | | |
| 67 | 78 ± 8 | 88 ± 12 | 0 | 0 ± 11 | 3rd step | BER | 70 | 70 | IR, MMS sensitive, EC50~10 |
| 200 | 51 ± 11 | 60 ± 5 | 0 | 0 | | | | | metabolite active |
| 25 | 59 ± 8 | 73 ± 5 | 0 | 13 ± 6 | | | | | |
| 213 | 36 ± 9 | 25 ± 1 | 0 | 0 | | | 70 | 70 | |
| Inhibit I, IV | | | | | | | | | |
| 113 | 53 ± 8 | 0 | 83 ± 5 | 5 ± 5 | | | | | |
| I specific | | | | | | | | | |
| 82 | 60 ± 2 | 29 ± 7 | 0 | 14 ± 11 | 3rd step | BER | 70 | 40 | cytostatic, G1, EC50~50 |
| 151 | 26 ± 1 | 0 | 0 | 0 | | BER | 70 | 70 | MMS sensitive, EC50~10 |
| 184 | 38 ± 12 | 0 | 0 | 1 ± 1 | | | 70 | 40 | EC50~10 |
| 190 | 53 ± 7 | 0 | 0 | 5 ± 1 | | | 40 | 40 | |
| 1 | 40 ± 9 | 0 | 0 | 0 ± 4 | | | | | |
| 43 | 29 ± 4 | 0 | 0 | 0 | | | 70 | 70 | |
| III specific | | | | | | | | | |
| 209 | 0 | 71 ± 3 | 0 | 0 | | | | | EC50 >100 |
| IV specific | | | | | | | | | |
| 215 | 0 | 0 | 61 ± 1 | 0 | | | | | EC50 >100 |
| 122 | 0 | 0 | 50 ± 5 | 0 | | | | | EC50 >100 |
| 93 | 0 | 0 | 37 ± 6 | 0 | | | | | |

TABLE 6

Compounds that decreased cell growth at low concentrations:

| Compound | IC$_{50}$ (μM) | | % of inhibition @100 μM (Helen's data) | | |
|---|---|---|---|---|---|
| | MCF10A | HCT116 | hLigI | hLigIII | hLigIV |
| 16$^r$ | 6 | NI | NI | NI | NI |
| 67 | 4 | 8 | 78 | 88 | NI |
| 78 | 7.5 | 10 | ND | >20 | <20 |
| 151 | 6 | 22 | 25 | NI | NI |
| 165 | 3 | NI | NI | NI | 37.2 |
| 180 | 3 | 12 | 58 | >40 | NI |
| 195* | 3 | NI | 26 | 24 | NI |
| 200 | ID (5) | ID (10) | 51 | 60 | NI |

Radiosensitizers:

| Compound | IC$_{50}$ ratios | | % of inhibition @100 μM (Helen's data) | | |
|---|---|---|---|---|---|
| | MCF10A | HCT116 | hLigI | hLigIII | hLigIV |
| 64 | 1.2 | NI | 61 | 49 | 52 |
| 151 | 1 | 2 | 26 | NI | NI |
| 105$^r$ | 1 | 1.3 | NI | NI | NI |

For 159 no IC$_{50}$ was achieved, but only slight sensitization to IR was observed. 159 did not inhibit human ligases in vitro.

Compounds that sensitized cells to MMS:

| Compound | Ratios of IC$_{50}$ | | % of inhibition @100 μM (Helen's data) | | |
|---|---|---|---|---|---|
| | MCF10A | HCT116 | hLigI | hLigIII | hLigIV |
| 16$^r$ | 1 | NI | NI | NI | NI |
| 67 | 1.2 | 1.4 | 78 | 88 | NI |
| 78 | 1.5 | 1 | ND | >20 | <20 |
| 151 | 1.8 | 1.7 | 25 | NI | NI |
| 159$^r$ | ND | 2** | NI | NI | NI |
| 165 | 1 | NI | NI | NI | 37.2 |
| 180 | 1 | ND | 58 | >40 | NI |
| 195* | 1.2 | NI | 26 | 24 | NI |
| 198$^r$ | NI | 2** | NI | NI | NI |
| 200 | ID (1) | ID (1) | 51 | 60 | NI |
| 214* | NI | ID (2) | ND | 42 | 40 |

IC$_{50}$ ratio: IC$_{50}$ value derived from growth curve of cells treated with compound alone compared to the IC$_{50}$ derived from growth curve of cells treated in combination with MMS (100 μM). Growth curves were normalized to either untreated control or control treated with MMS alone. The ratio of IC$_{50}$ of compounds that do not sensitize cells to MMS is equal to 1.

Compounds that sensitize cells to the PARP inhibitor 3-amino benzamide (3-AB):

| Compound | IC$_{50}$ ratios of non- and 3-AB treated cells | | % of inhibition @100 μM (Helen's data) | | |
|---|---|---|---|---|---|
| | MCF10A | HCT116 | hLigI | hLigIII | hLigIV |
| 64 | 2 | 1.6** | 61 | 49 | 52 |
| 67 | 1.7 | 1 | 78 | 88 | NI |
| 78 | 1 | ND | ND | >20 | <20 |
| 198$^r$ | 2** | 1 | NI | NI | NI |
| 200 | ID (1.2) | ID (1) | 51 | 60 | NI |
| 214* | ID (2) | ID (1.3) | ND | 42 | 40 |

IC50 ratio: ratio of IC$_{50}$ value derived from growth curve of cells treated with compound alone and IC$_{50}$ derived from growth curve of cells treated with compounds in combination with 3-AB (2 mM). Growth curves were normalized to either DMSO control or to DMSO and 3-AB. The ratio of IC$_{50}$ of compounds that do not sensitize cells to 3-AB is equal to 1.

Compounds that inhibit cell growth at high concentrations (~50 μM)

| Compound | IC$_{50}$ | | % of inhibition @100 μM (Helen's data) | | |
|---|---|---|---|---|---|
| | MCF10A | HCT116 | hLigI | hLigIII | hLigIV |
| 64 | 50 | NI | 61 | 49 | 52 |
| 105$^r$ | NI | ~50 | NI | NI | NI |
| 159$^r$ | NI | ~50 | NI | NI | NI |
| 177 | ND | 45 | 48 | 46 | NI |
| 198$^r$ | NI | NI | NI | NI | NI |
| 208 | 40 | ND | 21 | 24 | NI |

TABLE 6-continued

| | | | | | |
|---|---|---|---|---|---|
| 212[t] | ND | NI | NI | NI | NI |
| 214* | ID | ID | ND | 42 | 40 |

Compounds tested in the MTT assay that at 50 μM did not or only slightly inhibit cell proliferation of either MCF10A or HCT116:

| Cell line | | % of inhibition @100 μM (Helen's data) | | |
|---|---|---|---|---|
| MCF10A | HCT116 | hLigI | hLigIII | hLigIV |
| — | 16[t] | NI | NI | NI |
| — | 64 | 61 | 49 | 52 |
| 79[t] | ND | NI | NI | NI |
| 124[t] | 124 | NI | NI | NI |
| 130[t] | 130 | NI | NI | NI |
| — | 165 | NI | NI | 37 |
| ND | 184 (30%) | 38 | NI | NI |
| 193[t] | ND | NI | NI | NI |
| — | 195 | 26 | 24 | NI |
| 197 | 197 | 91 | 97 | 57 |
| 198**[t] | 198**[t] | NI | NI | NI |
| 199[t] (30%) | ND | NI | NI | NI |
| ND | 212[t] | NI | NI | NI |
| *214** | — | NI | 42 | 40 |
| 221[t] | ND | >20 | NI | NI |

Compounds that inhibit growth of both cell lines: MCF10A and HCT116

| | IC$_{50}$ (μM) | | % of inhibition @100 μM (Helen's data) | | |
|---|---|---|---|---|---|
| Compound | MCF10A | HCT116 | hLigI | hLigIII | hLigIV |
| 67 | 4 | 8 | 78 | 88 | NI |
| 78 | 7.5 | 10 | ND | >20 | <20 |
| 151 | 6 | 22 | 25 | NI | NI |
| 180 | 3 | 12 | 58 | >40 | NI |
| 200 | ID (5) | ID (10) | 51 | 60 | NI |

Compounds active on MCF10A cell line only:

| | IC$_{50}$ (μM) | % of inhibition @100 μM (Helen's data) | | |
|---|---|---|---|---|
| Compound | MCF10A | hLigI | hLigIII | hLigIV |
| 16[t] | 6 | NI | NI | NI |
| 64 | 50 | 61 | 49 | 52 |
| 165 | 3 | NI | NI | 37 |
| 195 | 3 | 26 | 24 | NI |
| 208 | 40 | 21 | 24 | NI |

Compounds active on HCT116 cells more than on MCF10A:

| | IC$_{50}$ (μM) | % of inhibition @100 μM (Helen's data) | | |
|---|---|---|---|---|
| Compound | HCT116 | hLigI | hLigIII | hLigIV |
| 105[t] | ~50 | NI | NI | NI |
| 159[t] | 50 | NI | NI | NI |
| 198[t] | ** | NI | NI | NI |
| 214* | 10 (10-50) | NI | 42 | 40 |

Compounds active in vitro that decreased cell growth of either MCF10A or HCT116 cell line:

| | IC$_{50}$ | | % of inhibition @ 100 μM (Helen's data) | | |
|---|---|---|---|---|---|
| Compound | MCF10A | HCT116 | hLigI | hLigIII | hLigIV |
| 64 | 50 | NI | 61 | 49 | 52 |
| 67 | 4 | 8 | 78 | 88 | NI |
| 78 | 7.5 | 10 | ND | >20 | <20 |
| 151 | 6 | 22 | 25 | NI | NI |
| 177 | ND | 45 | 48 | 46 | NI |
| 165 | 3 | NI | NI | NI | 37.2 |
| 180 | 3 | 3 | 58 | >40 | NI |
| 195* | 3 | NI | 26 | 24 | NI |
| 200 | ID (10-150) | ID (10-150) | 51 | 60 | NI |
| 208 | 40 | ND | 21 | 24 | NI |
| 214* | NI | ID (10-50) | ND | 42 | 40 |

TABLE 6-continued

Sensitizers to MMS and 3-AB

| Compound | MMS IC$_{50}$ ratios | | 3-AB IC$_{50}$ ratios | | % of inhibition @100 μM (Helen's data) | | |
|---|---|---|---|---|---|---|---|
| | MCF10A | HCT116 | MCF10A | HCT116 | hLigI | hLigIII | hLigIV |
| 64 | — | 2** | 2 | 1.6 | 61 | 49 | 52 |
| 67$^{tt}$ | 1.2 | 1.4 | 1.7 | 1 | 78 | 88 | NI |
| 78$^{tt}$ | 1.5 | 1 | 1 | ND | ND | >20 | <20 |
| 151$^{tt}$ | 1.8 | 1.7 | ND | ND | 25 | NI | NI |
| 159$^{t}$ | Ni | 2* | ND | ND | NI | Nit | NI |
| 195* | 1.2 | NI (1) | ND | ND | 26 | 24 | NI |
| 198$^{t}$ | NI (1)t | 2** | 2** | 1 | NI | Nit | NI |
| 214* | NI (1) | ID (2) | 2 | 1 | ND | 42 | 40 |

Total # of compounds tested on either cell line: 24 out of 192
$^{t}$indicates compounds that are inhibit cell growth but did not show any activity to inhibit ligases under cell-free conditions.
$^{tt}$indicates are the most active agents as tested on MCF10A and HCT116 cell lines
*compounds that are insoluble, form crystals in media
**compounds that alone at 50 μM did not inhibit cell growth by 50%, however sensitized cells to MMS or 3-AB
198 active at high concentrations (50 μM) sensitized MCF10A cells to 3-AB, and HCT116 cells to MMS; #214 sensitized MCF10A cells to 3-AB, and HCT116 to MMS. 214 is highly insoluble and undergoes self degradation in DMSO (MS data, BD).
ND—no data; ID—inconsistent data; NI—no inhibition

TABLE 7

Similarity between 10 active compounds (bold numbers) based on the Tanimoto Index (Tc %)

| | 25 | 64 | 67 | 82 | 113 | 123 | 189 | 190 | 197 | 200 |
|---|---|---|---|---|---|---|---|---|---|---|
| 25 | 100 | | | | | | | | | |
| 64 | 39 | 100 | | | | | | | | |
| 67 | 38 | 53 | 100 | | | | | | | |
| 82 | 42 | 53 | 69 | 100 | | | | | | |
| 113 | 22 | 34 | 45 | 30 | 100 | | | | | |
| 123 | 15 | 32 | 16 | 16 | 22 | 100 | | | | |
| 189 | 40 | 40 | 37 | 43 | 24 | 30 | 100 | | | |
| 190 | 43 | 28 | 32 | 39 | 18 | 19 | 52 | 100 | | |
| 197 | 40 | 35 | 24 | 21 | 18 | 20 | 18 | 22 | 100 | |
| 200 | 40 | 19 | 25 | 27 | 13 | 4 | 25 | 35 | 35 | 100 |

We claim:

1. A method of treating chronic leukemia, breast cancer or colon cancer exhibiting an altered DNA damage response in a patient in need comprising administering to said patient an effective amount of at least one anti-cancer compound according to the chemical structures as set forth below:

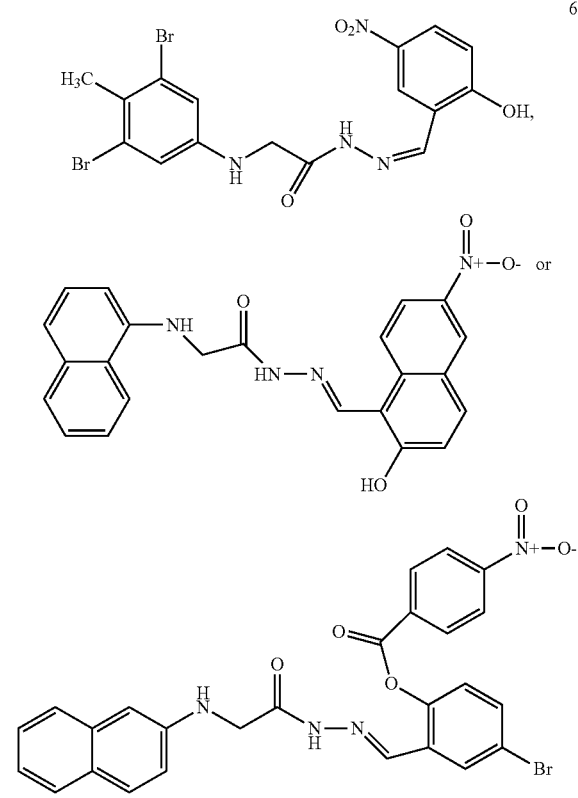

in combination with a second cancer treatment comprising a DNA damaging agent.

2. The method according to claim 1 wherein said anti-cancer compound is

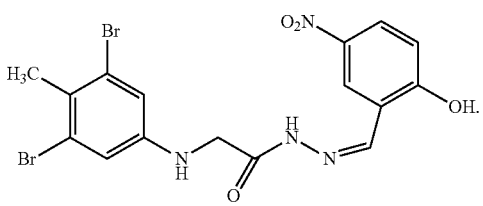

3. The method according to claim 1 wherein said DNA damaging agent is ionizing radiation, a PARP inhibitor or a DNA alkylating agent.

4. The method according to claim 3 wherein said DNA damaging agent is a PARP inhibitor.

5. The method according to claim 4 wherein said PARP inhibitor is 3-aminobenzamide.

6. The method according to claim 3 wherein said DNA damaging agent is ionizing radiation.

7. The method according to claim 3 wherein said DNA damaging agent is a DNA alkylating agent.

8. The method according to claim 7 wherein said DNA alkylating agent is methyl methanesulfonate (MMS).

9. The method according to claim 1 wherein said cancer is breast cancer.

10. The method according to claim 1 wherein said cancer is chronic leukemia.

11. The method according to claim 1 wherein said compound is

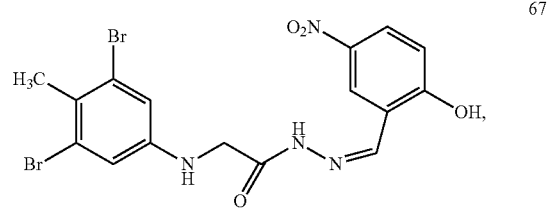 [SMILES: Cc1c(Br)cc(NCC(=O)N/N=C\c2cc([N+](=O)[O-])ccc2O)cc1Br]

and said cancer is chronic leukemia.

12. The method according to 1 wherein said compound is

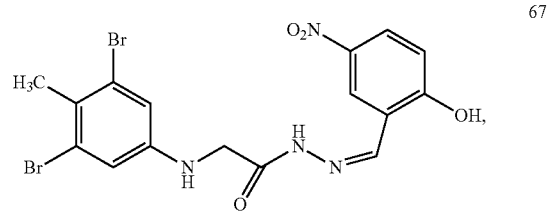 [SMILES: Cc1c(Br)cc(NCC(=O)N/N=C\c2cc([N+](=O)[O-])ccc2O)cc1Br]

and said cancer is breast cancer.

13. The method according to claim 1 wherein said compound is

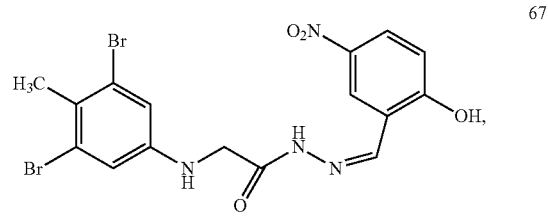 [SMILES: Cc1c(Br)cc(NCC(=O)N/N=C\c2cc([N+](=O)[O-])ccc2O)cc1Br]

and said cancer is colon cancer.

14. The method of claim 1, wherein said DNA damaging agent is administered at the same time with administering said at least one compound.

15. The method of claim 1, wherein said DNA damaging agent is administered prior to administering said at least one compound.

16. The method of claim 1, wherein said DNA damaging agent is administered after administering said at least one compound.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: 25-mer (Synthetic Construct)

<400> SEQUENCE: 1
cgccagggtt ttcccagtca cgacc                                          25

<210> SEQ ID NO 2
<211> LENGTH: 18
<212> TYPE: DNA
<213> ORGANISM: Artificial Sequence
<220> FEATURE:
<223> OTHER INFORMATION: 18-mer (Synthetic Construct)

<400> SEQUENCE: 2
gtaaaacgac ggccagtg                                                  18